(12) United States Patent
Huang et al.

(10) Patent No.: US 11,186,556 B1
(45) Date of Patent: Nov. 30, 2021

(54) SALTS OF A THIAZOLIDINONE COMPOUND, SOLID FORMS, COMPOSITIONS AND METHODS OF USE THEREOF

(71) Applicant: Celgene Corporation, Summit, NJ (US)

(72) Inventors: Lianfeng Huang, Basking Ridge, NJ (US); Daozhong Zou, Raritan, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/653,629

(22) Filed: Oct. 15, 2019

Related U.S. Application Data

(60) Provisional application No. 62/746,384, filed on Oct. 16, 2018.

(51) Int. Cl.

| | |
|---|---|
| *C07D 277/54* | (2006.01) |
| *A61P 25/28* | (2006.01) |
| *A61P 17/06* | (2006.01) |
| *A61P 29/00* | (2006.01) |
| *A61K 9/48* | (2006.01) |
| *A61K 9/20* | (2006.01) |

(52) U.S. Cl.
CPC ............ *C07D 277/54* (2013.01); *A61P 17/06* (2018.01); *A61P 25/28* (2018.01); *A61P 29/00* (2018.01); *A61K 9/20* (2013.01); *A61K 9/48* (2013.01); *C07B 2200/13* (2013.01)

(58) Field of Classification Search
CPC .................................................. C07D 277/54
See application file for complete search history.

(56) References Cited

U.S. PATENT DOCUMENTS

| | | | | |
|---|---|---|---|---|
| 4,432,987 | A * | 2/1984 | Barth ................... | C07D 499/00 514/193 |
| 5,721,359 | A * | 2/1998 | Dunn ..................... | A61P 31/04 540/227 |
| 7,145,002 | B2 * | 12/2006 | Brands ................. | C07D 477/20 540/350 |
| 7,435,828 | B2 | 10/2008 | Binkert et al. | |
| 8,263,780 | B2 | 9/2012 | Abele et al. | |
| 8,273,779 | B2 * | 9/2012 | Binkert ................... | A61P 25/00 514/370 |
| RE43,728 | E | 10/2012 | Binkert et al. | |
| 8,399,514 | B2 | 3/2013 | Lukashev et al. | |
| 8,524,752 | B2 * | 9/2013 | Binkert .................... | A61P 3/04 514/369 |

(Continued)

FOREIGN PATENT DOCUMENTS

| | | |
|---|---|---|
| EP | 2 316 430 B1 | 6/2012 |
| GB | WO 2010/046835 * | 4/2010 |

(Continued)

OTHER PUBLICATIONS

Swarbrick et al. (Encyclopedia of Pharmaceutical Technology 13 (Marcel Dekker, NY 1996) pp. 453-499).*

(Continued)

*Primary Examiner* — Valerie Rodriguez-Garcia
(74) *Attorney, Agent, or Firm* — Jones Day

(57) ABSTRACT

Provided herein are formulations, processes, solid forms and methods of use relating to salts of (Z)-5-((Z)-3-chloro-4-((R)-2,3-dihydroxypropoxy)benzylidene)-2-(propylimino)-3-(o-tolyl)thiazolidin-4-one.

24 Claims, 44 Drawing Sheets

Figure 1:
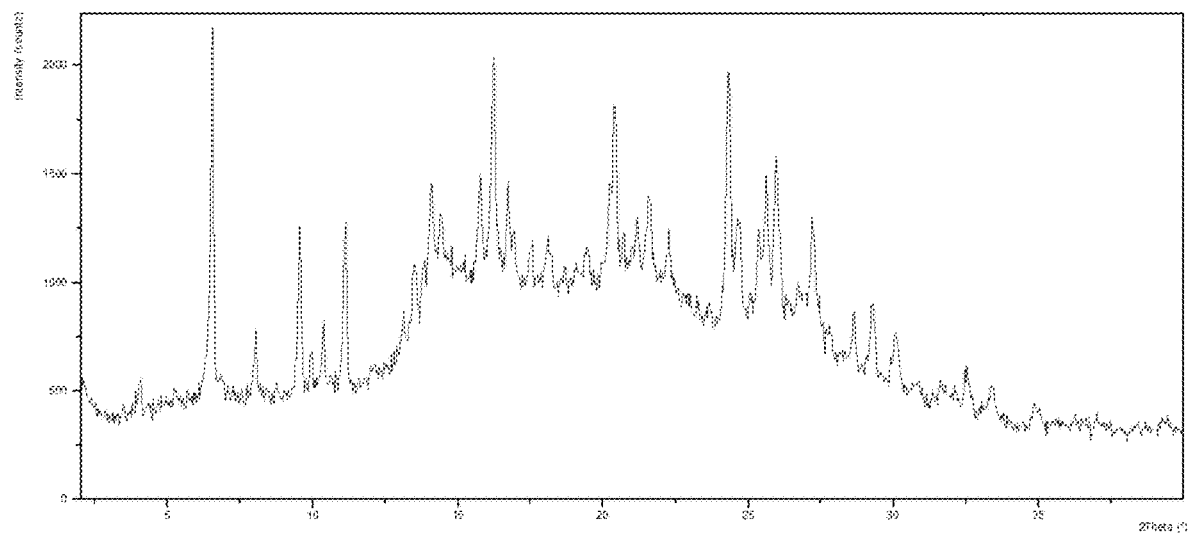

XRPD of Form A of an HCl Salt of Compound 1

(56) References Cited

U.S. PATENT DOCUMENTS

| | | | |
|---|---|---|---|
| 8,785,484 | B2 | 7/2014 | Brossard et al. |
| 8,912,340 | B2 | 12/2014 | Abele et al. |
| 9,000,018 | B2 | 4/2015 | Binkert et al. |
| 9,062,014 | B2 | 6/2015 | Bonham et al. |
| 9,340,518 | B2 | 5/2016 | Herse |
| 2014/0303217 | A1 | 10/2014 | Brossard et al. |
| 2014/0316140 | A1 | 10/2014 | Brossard et al. |

FOREIGN PATENT DOCUMENTS

| | | |
|---|---|---|
| WO | WO 2005/054215 A1 | 6/2005 |
| WO | WO 2005/123677 A1 | 12/2005 |
| WO | WO 2006/010379 A1 | 2/2006 |
| WO | WO 2006/010544 A2 | 2/2006 |
| WO | WO 2006/100633 A1 | 9/2006 |
| WO | WO 2006/100635 A2 | 9/2006 |
| WO | WO 2007/080542 A1 | 7/2007 |
| WO | WO 2008/029306 A2 | 3/2008 |
| WO | WO 2008/062376 A2 | 5/2008 |
| WO | WO 2008/097596 A2 | 8/2008 |
| WO | WO 2008/114157 A1 | 9/2008 |
| WO | WO 2009/024905 A1 | 2/2009 |
| WO | WO 2009/074950 A2 | 6/2009 |
| WO | WO 2009/115954 A1 | 9/2009 |
| WO | WO 2010/046835 A1 | 4/2010 |
| WO | WO 2011/007324 A1 | 1/2011 |
| WO | WO 2013/184888 A1 | 12/2013 |
| WO | WO 2014/027330 A1 | 2/2014 |
| WO | WO 2016/091996 A1 | 6/2016 |
| WO | WO 2016/092042 A1 | 6/2016 |
| WO | WO 2017/107972 A1 | 6/2017 |
| WO | WO 2018/167030 A1 | 9/2018 |
| WO | WO 2019/060147 A1 | 3/2019 |

OTHER PUBLICATIONS

Morissette et al. (Advanced Drug Delivery Reviews, 56, (2004) p. 275-300).*

Pharma's Almanac "The People's Choice: Premeasured Single Dosage Forms" published online on June 5, 2017—https://www.pharmasalmanac.com/articles/the-peoples-choice-premeasured-single-dosage-forms.*

Chaudhry et al. (Neurotherapeutics (2017) 14:859-873).*

Boehler et al., "Absolute Bioavailability of Ponesimod, a Selective S1P 1 Receptor Modulator, in Healthy Male Subjects," *Eur J Drug Metab Pharmacokinet.*, 42(1):129-134 (2017).

Bolli et al., "2-imino-thiazolidin-4-one Derivatives as Potent, Orally Active S1P1 Receptor Agonists," J Med Chem.;53(10):4198-4211 (2010).

Brossard et al., "Multiple-dose Tolerability, Pharmacokinetics, and Pharmacodynamics of Ponesimod, an S1P1 Receptor Modulator: Favorable Impact of Dose Up-Titration," *J. Clin. Pharmacol.*, 54(2):179-188 (2014).

D'Ambrosio et al., *Immunopharmacol Immunotoxicol.* 37(1):103-109. (2015).

D'Ambrosio et al., "Ponesimod, a Selective S1P1 Receptor Modulator: A Potential Treatment for Multiple Sclerosis and Other Immune-Mediated Diseases," *Ther. Adv. Chronic. Dis.*, 7(1):18-33 (2016).

Guerard et al., "Effect of Hepatic or Renal Impairment on the Pharmacokinetics, Safety, and Tolerability of Ponesimod, a Selective S1P1 Receptor Modulator," *Basic Clin. Pharmacol. Toxicol.*, 118(5):356-368 (2016).

Hoch et al., "Effect of Ponesimod, a Selective S1P1 Receptor Modulator, on the QT Interval in Healthy Individuals," *Basic Clin. Pharmacol. Toxicol.*, 116(5): 429-437 (2015).

Hoch et al., "Clinical Pharmacology of Ponesimod, a Selective S1P$_1$ Receptor Modulator, After Uptitration to Supratherapeutic Doses in Healthy Subjects," *Eur. J. Pharm. Sci.*, 63:147-153 (2014).

Juif et al., "Biocomparisonof three formulations of the SIP receptor modulator ponesimod in healthy subjects," *Drugs R D.* 15(2):203-210 (2015).

Juif et al., "Clinical Pharmacology, Efficacy, and Safety Aspects of sphingosine-1-phosphate Receptor Modulators," *Expert Opin Drug Metab Toxicol.* 12(8):879-895 (2016).

Juif et al., "Mitigation of Initial Cardiodynamic Effects of the S1P 1 Receptor Modulator Ponesimod Using a Novel Up-Titration Regimen," *J. Clin. Pharmacol.*, 57(3):401-410 (2017).

Jurcevic et al., "Effects of Multiple-Dose Ponesimod, a Selective S1P 1 Receptor Modulator, on Lymphocyte Subsets in Healthy Humans," *Drug Des. Devel Ther.*, 11:123-131 (2016).

Krause et al., "Population Pharmacokinetics and Pharmacodynamics of Ponesimod, a Selective S1P1 Receptor Modulator," *J Pharmacokinet Pharmacodyn.*, 41(3):261-278 (2014).

Lott et al., "Impact of Demographics, Organ Impairment, Disease, Formulation, and Food on the Pharmacokinetics of the Selective S1P 1 Receptor Modulator Ponesimod Based on 13 Clinical Studies," *Clin. Pharmacokinet.*, 56(4):395-408 (2017).

Lott et al., "Population Pharmacokinetics of Ponesimod and Its Primary Metabolites in Healthy and Organ-Impaired Subjects," *Eur J Pharm Sci.*,89:83-93 (2016).

Lott et al., Pharm Res.;34(3):599-609 (2017).

NCT01006265: Clinical Study to Evaluate the Efficacy, Safety, and Tolerability of ACT-128800 in Patients With Relapsing-remitting Multiple Sclerosis. https://clinicaltrials.gov/ct2/show/NCT01006265. First posted Nov. 1, 2009; last update posted Apr. 4, 2017; downloaded May 28, 2020.

NCT01093326: Clinical Study to Investigate the Long-term Safety, Tolerability, and Efficacy of Ponesimod in Patients With Relapsing-remitting Multiple Sclerosis. https://clinicaltrials.gov/ct2/show/NCT01093326?term=NCT01093326&draw=2&rank=1. Fist posted Mar. 25, 2010; last updated posted May 21, 2020; downloaded May 28, 2020.

NCT01755871: Long-term Effect of Fingolimod on Circulating Immunocompetent Mononuclear Cells in Patients With Multiple Sclerosis (terminated). https://clinicaltrials.gov/ct2/show/NCT01755871?term=NCT01755871&draw=2&rank=1. First posted Dec. 24, 2012; Last Update Posted Jun. 9, 2016; downloaded May 28, 2020.

NCT02029482: Study to Investigate the Safety, Tolerability, Pharmacokinetics, and Pharmacodynamics of ACT-128800 in Healthy Subjects. https://clinicaltrials.gov/ct2/show/NCT02029482?term=NCT02029482&draw=2&rank=1. First Posted Jan. 8, 2014; Last Update Posted Jan. 8, 2014; downloaded May 28, 2020.

NCT02068235: Study to Investigate the Absolute Bioavailability of a Single Oral Dose of Ponesimod in Healthy Male Subjects. https://clinicaltrials.gov/ct2/show/NCT02068235?term=NCT02068235&draw=2&rank=1. First Posted Feb. 21, 2014; Last Update Posted May 21, 2015; downloaded May 28, 2020.

NCT02126956: Mass Balance, Pharmacokinetics, and Metabolism of 14C-labeled ACT-128800 Administered to Healthy Male Subjects. https://clinicaltrials.gov/ct2/show/NCT02126956?term=NCT02126956&draw=2&rank=1. First Posted Apr. 30, 2014; Late Update Posted Apr. 30, 2014; downloaded May 28, 2020.

NCT02136888: Study of the Electrocardiographic Effects of Ponesimod in Healthy Male and Female Subjects. https://clinicaltrials.gov/ct2/show/NCT02136888?term=NCT02136888&draw=2&rank=1. First Posted May 13, 2014; Last Update Posted May 13, 2014; downloaded May 28, 2020.

NCT02223832: Study to Evaluate the Pharmacokinetics, Tolerability, and Safety of ACT-128800 in Japanese and Caucasian Healthy Male and Female Subjects. https://clinicaltrials.gov/ct2/show/NCT02223832?term=NCT02223832&draw=2&rank=1. First Posted Aug. 22, 2014; Last Update Posted Aug. 22, 2014; downloaded May 22, 2020.

NCT02425644: Oral Ponesimod Versus Teriflunomide In Relapsing MUltiple Sclerosis (OPTIMUM). https://clinicaltrials.gov/ct2/show/NCT02425644?term=NCT02425644&draw=2&rank=1. First Posted Apr. 24, 2015; Last Update Posted May 27, 2020; downloaded May 28, 2020.

NCT02461134: Clinical Study to Investigate the Biological Activity, Safety, Tolerability, and Pharmacokinetics of Ponesimod in Subjects With Symptomatic Chronic GVHD (terminated). https://clinicaltrials.gov/ct2/show/NCT02461134?term=NCT02461134&draw=2&rank=1. First Posted Jun. 3, 2015; Last Update Posted May 9, 2018; downloaded May 28, 2020.

(56) References Cited

OTHER PUBLICATIONS

NCT02907177: Clinical Study to Compare the Efficacy and Safety of Ponesimod to Placebo in Subjects With Active Relapsing Multiple Sclerosis Who Are Treated With Dimethyl Fumarate (Tecfidera®). https://clinicaltrials.gov/ct2/show/NCT02907177?term=NCT02907177 &draw=2&rank=1. First Posted Sep. 20, 2016; Last Update Posted Apr. 6, 2020; downloaded May 28, 2020.

Olsson et al., "Oral Ponesimod in Relapsing-Remitting Multiple Sclerosis: A Randomised Phase II Trial," *Neuro.l Neurosurg. Psychiatry.*, 85(11):1198-1208 (2014).

Piali et al., "The Selective Sphingosine 1-phosphate Receptor 1 Agonist Ponesimod Protects Against Lymphocyte-Mediated Tissue Inflammation," *J. Pharmacol. Exp. Ther.*, 337(2):547-556 (2011).

Rey et al., "Desensitization by Progressive Up-Titration Prevents First-Dose Effects on the Heart: Guinea Pig Study With Ponesimod, a Selective S1P1 Receptor Modulator," *PLoS One.*, 8(9):e74285 (2013).

Reyes et al., "Effects of Ethnicity and Sex on the Pharmacokinetics and Pharmacodynamics of the Selective sphingosine-1-phosphate Receptor 1 Modulator Ponesimod: A Clinical Study in Japanese and Caucasian Subjects," *Pharmacology*, 94(5-6): 223-229 (2014).

Reyes et al., "Mass Balance, Pharmacokinetics and Metabolism of the Selective S1P1 Receptor Modulator Ponesimod in Humans," *Xenobiotica.*, 45(2):139-149 (2015).

Scherz et al. "Three Different Up-Titration Regimens of Ponesimod, an S1P1 Receptor Modulator, in Healthy Subjects," *J. Clin. Pharmacol.*, 55(6):688-697 (2015).

\* cited by examiner

PLM Image of Form A of an HCl Salt of Compound 1

PLM Image of Form C of an HCl Salt of Compound 1

PLM Image of Form B of an HBr Salt of Compound 1

PLM Image of Form A of a Napadisylate Salt of Compound 1

PLM Image of Form B of a Napadisylate Salt of Compound 1

PLM Image of Form C of a Napadisylate Salt of Compound 1

DSC and TGA of Form A of a 2-Naphthalenesulfonate Salt of Compound 1

PLM Image of Form A of a 2-Naphthalenesulfonate Salt of Compound 1

PLM Image of Form A of an Edisylate Salt of Compound 1

PLM Image of Form B of an Edisylate Salt of Compound 1

SALTS OF A THIAZOLIDINONE COMPOUND, SOLID FORMS, COMPOSITIONS AND METHODS OF USE THEREOF

This application claims priority to U.S. Provisional Application No. 62/746,384, filed Oct. 16, 2018, the entirety of which is incorporated herein by reference.

1. FIELD

Provided herein are salts of and solid forms comprising salts of (Z)-5-((Z)-3-chloro-4-((R)-2,3-dihydroxypropoxy) benzylidene)-2-(propylimino)-3-(o-tolyl)thiazolidin-4-one. Pharmaceutical compositions comprising such salts and solid forms and methods of use of such salts and solid forms for treating, preventing, and managing various disorders are also provided herein.

2. BACKGROUND

When the immune system functions normally, it produces a response intended to protect against harmful or foreign substances such as bacteria, parasites, and cancerous cells. Autoimmune diseases arise when the immune system attacks one or more of the body's normal constituents as if they were a foreign substance. These attacks cause inflammation and tissue damage that may lead to autoimmune disorders. There are more than 80 diseases that occur as a result of the body's autoimmune response to various harmful or foreign substances, affecting more than 23.5 million people in the United States. Some of the most common types of autoimmune or chronic inflammatory diseases include Graves' disease, Type 1 diabetes, multiple sclerosis, inflammatory bowel disease, systemic lupus, polymyositis, dermatomyositis, lupus nephritis, rheumatoid arthritis, and psoriasis.

Multiple Sclerosis ("MS") is an autoimmune disease of the central nervous system, characterized by degeneration of the protective sheath ("myelin") that covers nerve fibers in the brain and spinal cord. More than 2.5 million people in the world suffer from MS, and it is the most common neurologic, disabling disease in young adults. Diagnosis is generally made between 15 and 50 years of age, with symptoms either occurring in recurring, isolated attacks (i.e., relapsing forms) or symptoms increasing over time (i.e., progressive forms). Permanent neurological dysfunction can result from incomplete recovery from acute relapses or as a consequence of slow progression of disability.

There is a need in the art for novel drug products for the treatment of MS and other autoimmune diseases of the central nervous systems. Alternative solid forms of pharmaceutical compounds have emerged as a possible approach to modulate or enhance the physical and chemical properties of drug products. The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solid forms include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Notably, it is not possible to predict apriori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

The type of salt form of a particular active pharmaceutical ingredient may affect certain properties of the active pharmaceutical ingredient. These properties include solubility, stability, and bioavailability.

3. SUMMARY

Provided herein are salts of Compound 1:

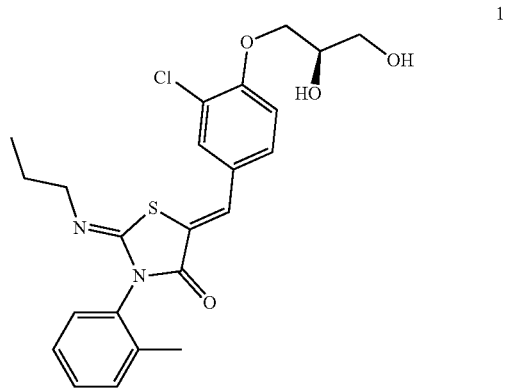 [SMILES: CCC/N=C1\S/C(=C\c2ccc(OC[C@H](O)CO)c(Cl)c2)C(=O)N1c1ccccc1C]

having the chemical name (Z)-5-((Z)-3-chloro-4-((R)-2,3-dihydroxypropoxy)benzylidene)-2-(propylimino)-3-(o-tolyl)thiazolidin-4-one (also known as ponesimod). In one embodiment, the salt is an HCl salt, an HBr salt, a napadisylate salt, a sulfuric acid salt, an edisylate salt, a camphor-O-sulfonic acid salt, an ethanesulfonic acid salt, a p-toluenesulfonic acid salt, a trifluoroacetic acid salt, a methanesulfonic acid salt, a naphthalene-2-sulfonic acid salt, or a benzenesulfonic acid salt.

Also Provided herein are solid forms comprising salts of Compound 1 (e.g., crystalline forms, amorphous forms, polymorphs or mixtures thereof). The solid forms also include solid forms comprising salts of a tautomer of Compound 1. Also provided herein are methods of preparing, isolating, and characterizing the solid forms.

In one embodiment, the solid form is Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, or Form C of an edisylate salt of Compound 1, as described herein.

In another embodiment, provided herein are pharmaceutical compositions comprising one or more of the salts described herein. In another embodiment, provided herein are pharmaceutical compositions comprising one or more of the solid forms described herein. In certain embodiments, the solid form is no less than 95% pure. In certain embodiments, the pharmaceutical composition further comprises a second solid form described herein. In certain embodiments, the pharmaceutical composition further comprises an amorphous form of a salt of Compound 1. In certain embodiments, the pharmaceutical composition further comprises a free base form of Compound 1. In certain embodiments, the pharmaceutical composition further comprises a pharmaceutically acceptable excipient or carrier. In certain embodiments, the pharmaceutical composition is a single unit dosage form. In certain embodiments, the pharmaceutical composition is a tablet. In certain embodiments, the pharmaceutical composition is a capsule.

In another embodiment, provided herein is a method of treating multiple sclerosis, wherein the method comprises administering to a patient in need thereof a therapeutically effective amount of a salt described herein. In another embodiment, provided herein is a method of treating multiple sclerosis, wherein the method comprises administering to a patient in need thereof a therapeutically effective amount of a solid form described herein. In another embodiment, provided herein is a method of treating multiple sclerosis, wherein the method comprises administering to a patient in need thereof a therapeutically effective amount of a pharmaceutical composition described herein. In one embodiment, the multiple sclerosis is relapsing multiple sclerosis. In one embodiment, the multiple sclerosis is relapsing-remitting multiple sclerosis.

In another embodiment, provided herein is a method of treating psoriasis, wherein the method comprises administering to a patient in need thereof a therapeutically effective amount of a salt described herein. In another embodiment, provided herein is a method of treating psoriasis, wherein the method comprises administering to a patient in need thereof a therapeutically effective amount of a solid form described herein. In another embodiment, provided herein is a method of treating psoriasis, wherein the method comprises administering to a patient in need thereof a therapeutically effective amount of a pharmaceutical formulation described herein. In one embodiment, the psoriasis is moderate to severe chronic plaque psoriasis.

In another embodiment, provided herein is a method of treating polymyositis, wherein the method comprises administering to a patient in need thereof a therapeutically effective amount of a salt described herein. In another embodiment, provided herein is a method of treating polymyositis, wherein the method comprises administering to a patient in need thereof a therapeutically effective amount of a solid form described herein. In another embodiment, provided herein is a method of treating polymyositis, wherein the method comprises administering to a patient in need thereof a therapeutically effective amount of a pharmaceutical formulation described herein.

4. BRIEF DESCRIPTION OF THE DRAWINGS

FIG. 1 provides a representative X-ray powder diffraction (XRPD) pattern of Form A of an HCl salt of Compound 1.

Figure 2:
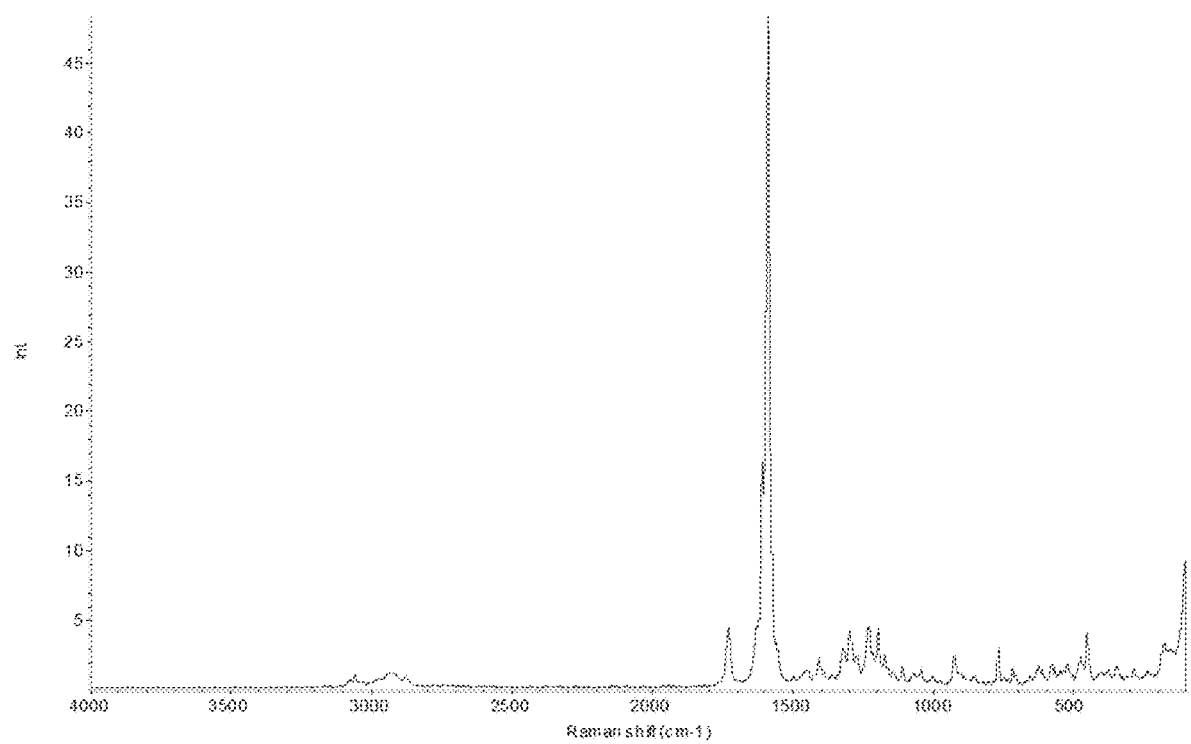

FIG. 2 provides a representative FT-Raman spectrum of Form A of an HCl salt of Compound 1.

Figure 3:
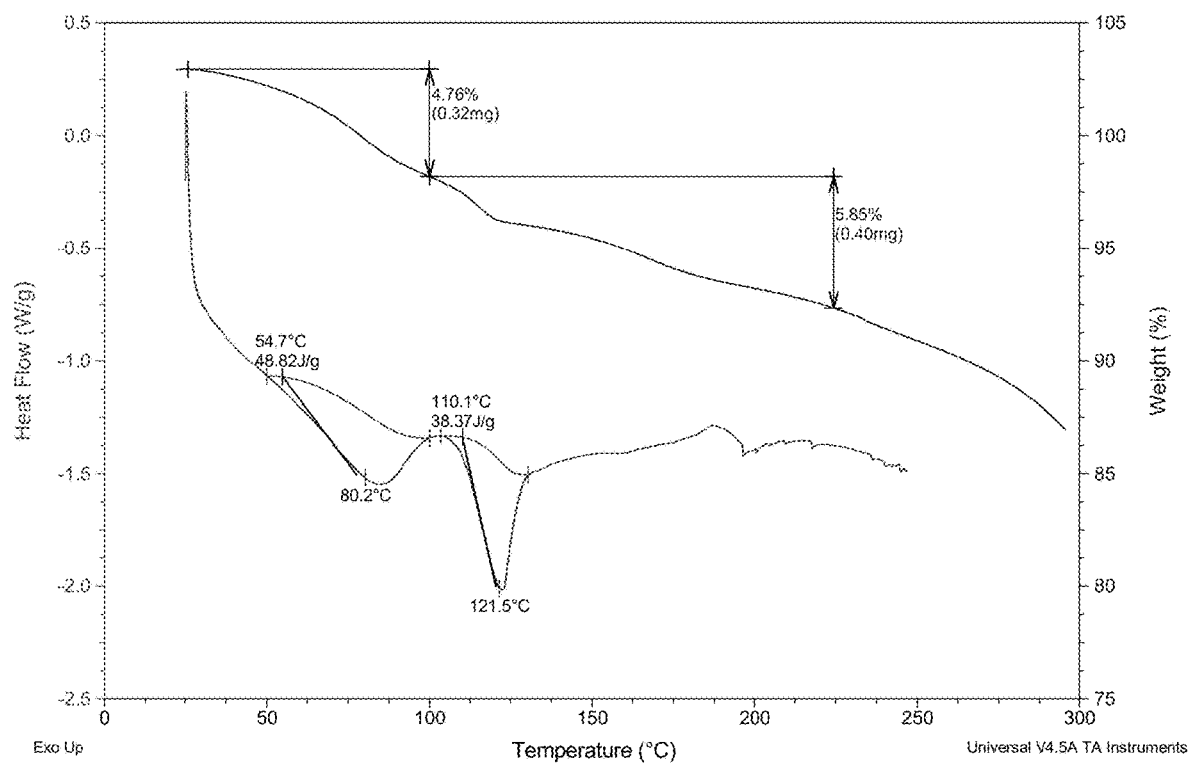

FIG. 3 provides representative differential scanning calorimetry (DSC) and thermal gravimetric analysis (TGA) thermograms of Form A of an HCl salt of Compound 1.

Figure 4:
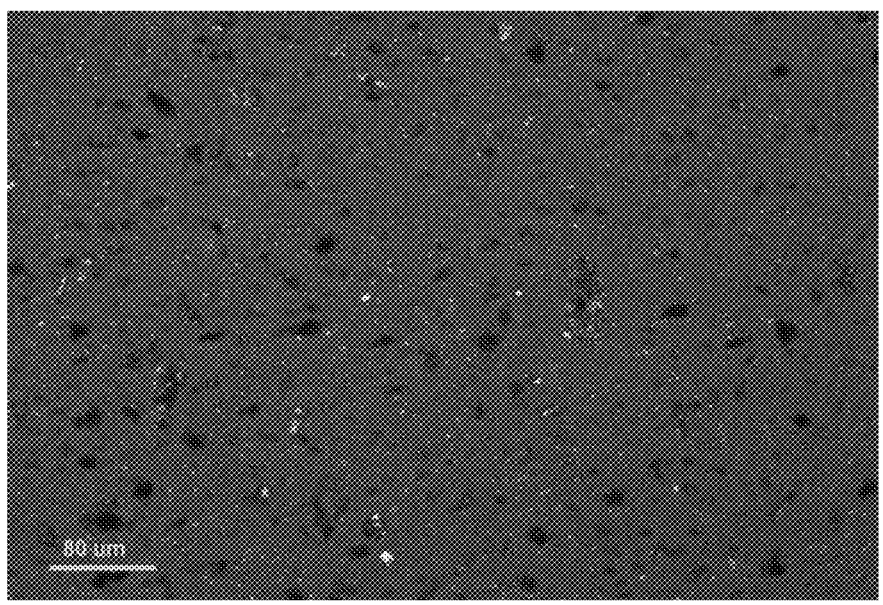

FIG. 4 provides a representative polarized light microscopy (PLM) image of Form A of an HCl salt of Compound 1.

Figure 5:
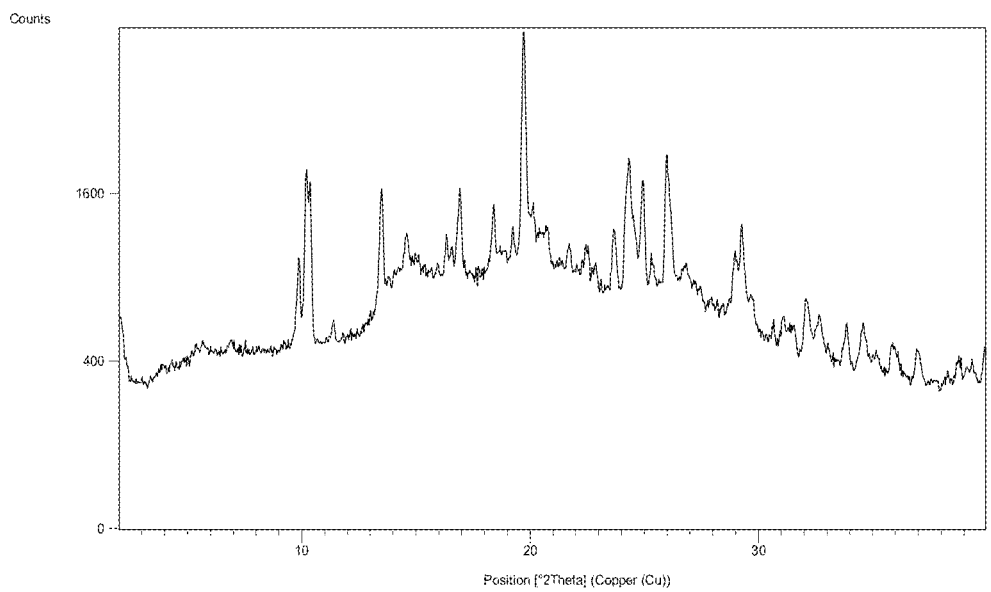

FIG. 5 provides a representative XRPD pattern of Form B of an HCl salt of Compound 1.

Figure 6:
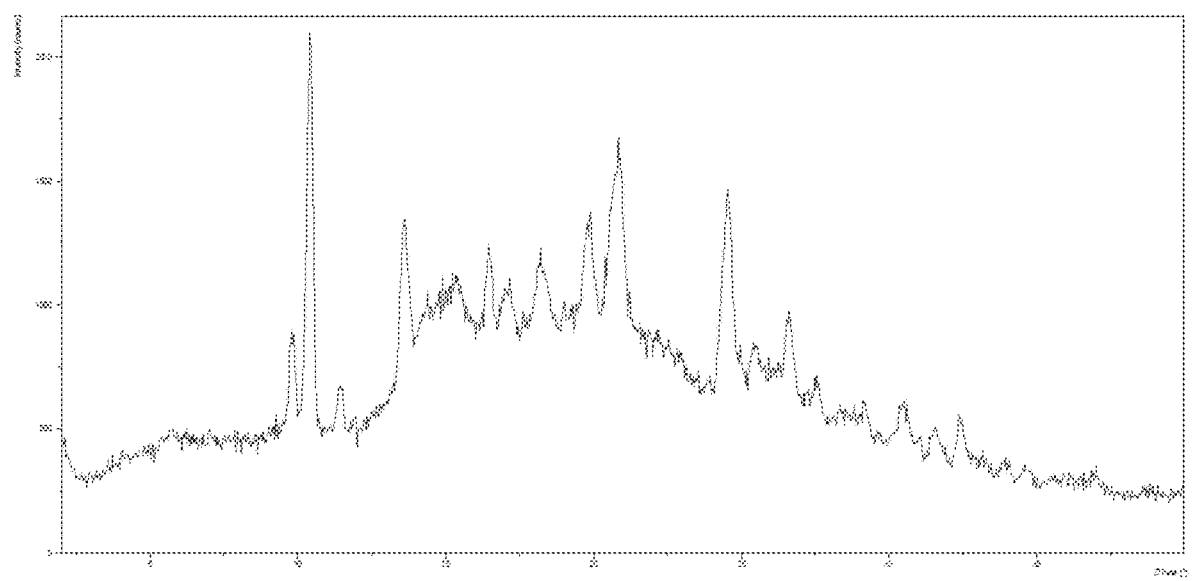

FIG. 6 provides a representative XRPD pattern of Form C of an HCl salt of Compound 1.

Figure 7:
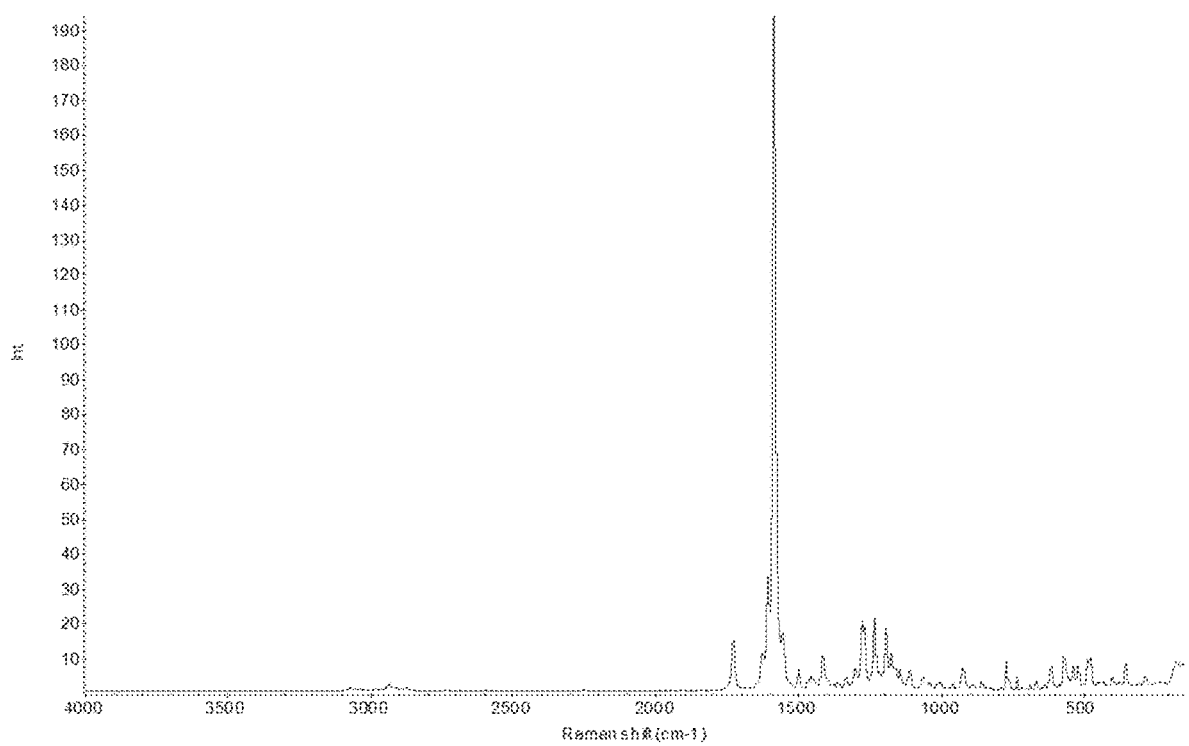

FIG. 7 provides a representative FT-Raman spectrum of Form C of an HCl salt of Compound 1.

Figure 8:
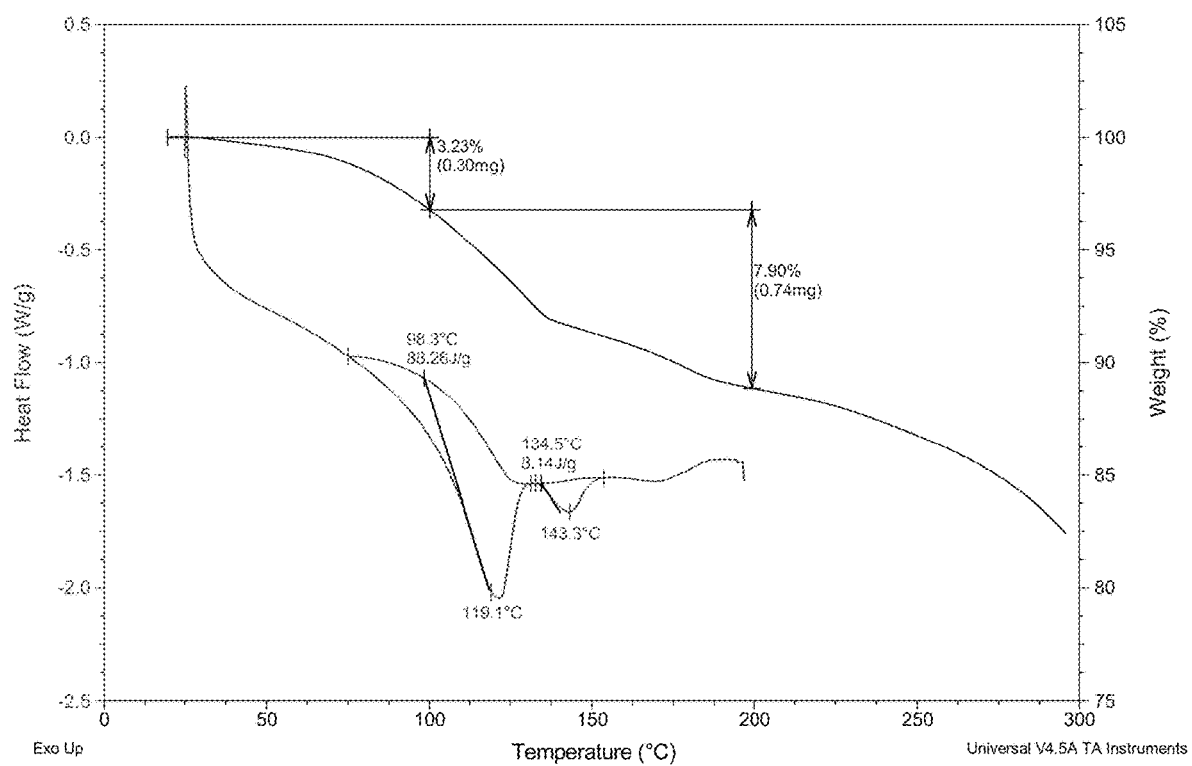

FIG. 8 provides representative DSC and TGA thermograms of Form C of an HCl salt of Compound 1.

Figure 9:
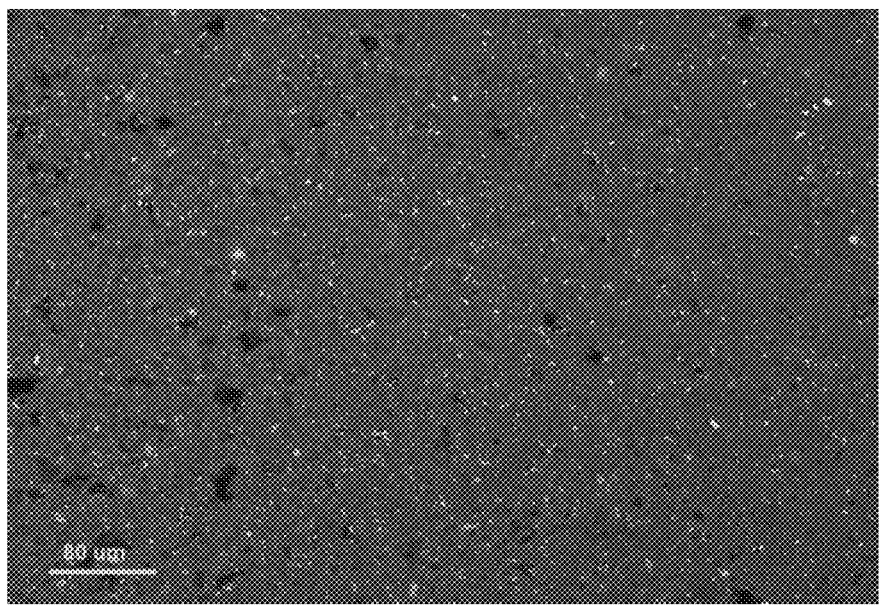

FIG. 9 provides a representative PLM image of Form C of an HCl salt of Compound 1.

Figure 10:
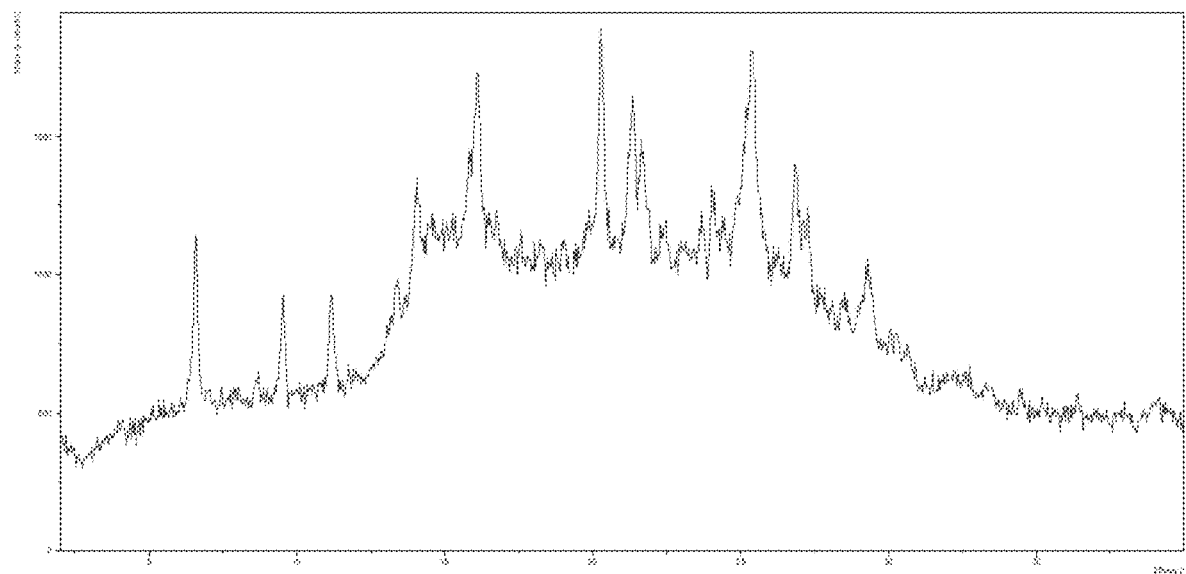

FIG. 10 provides a representative XRPD pattern of Form A of an HBr salt of Compound 1.

Figure 11:
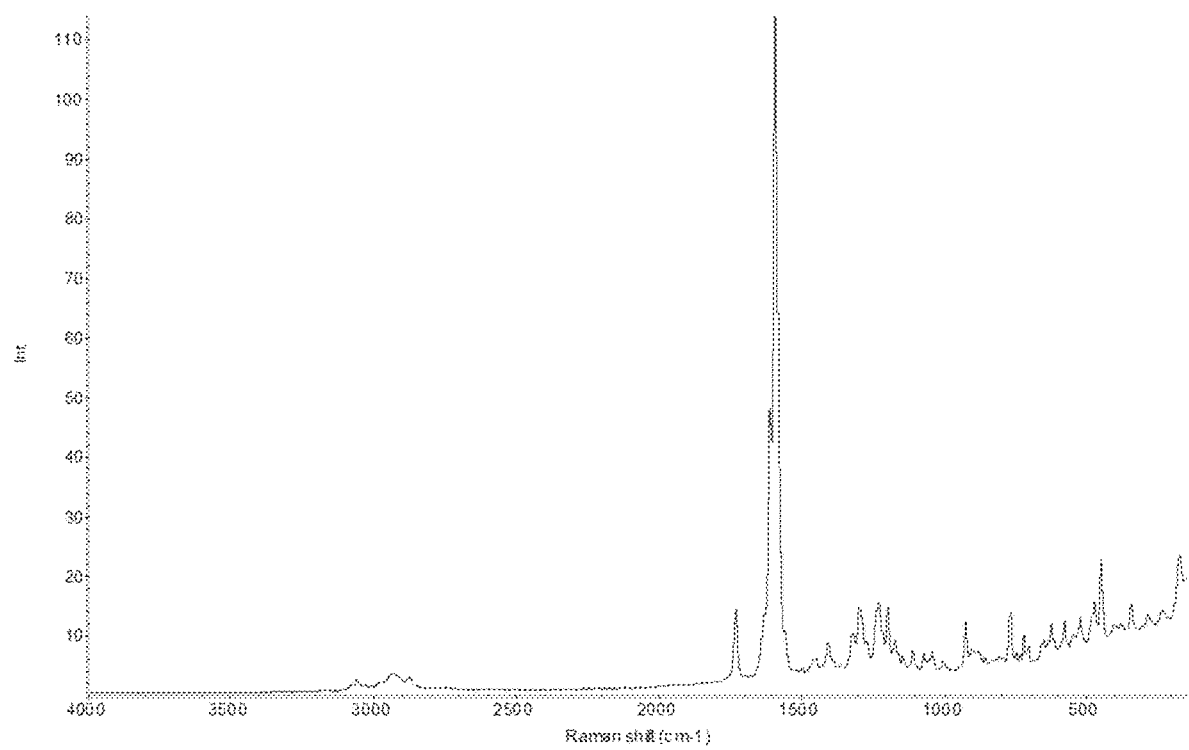

FIG. 11 provides a representative FT-Raman spectrum of Form A of an HBr salt of Compound 1.

Figure 12:
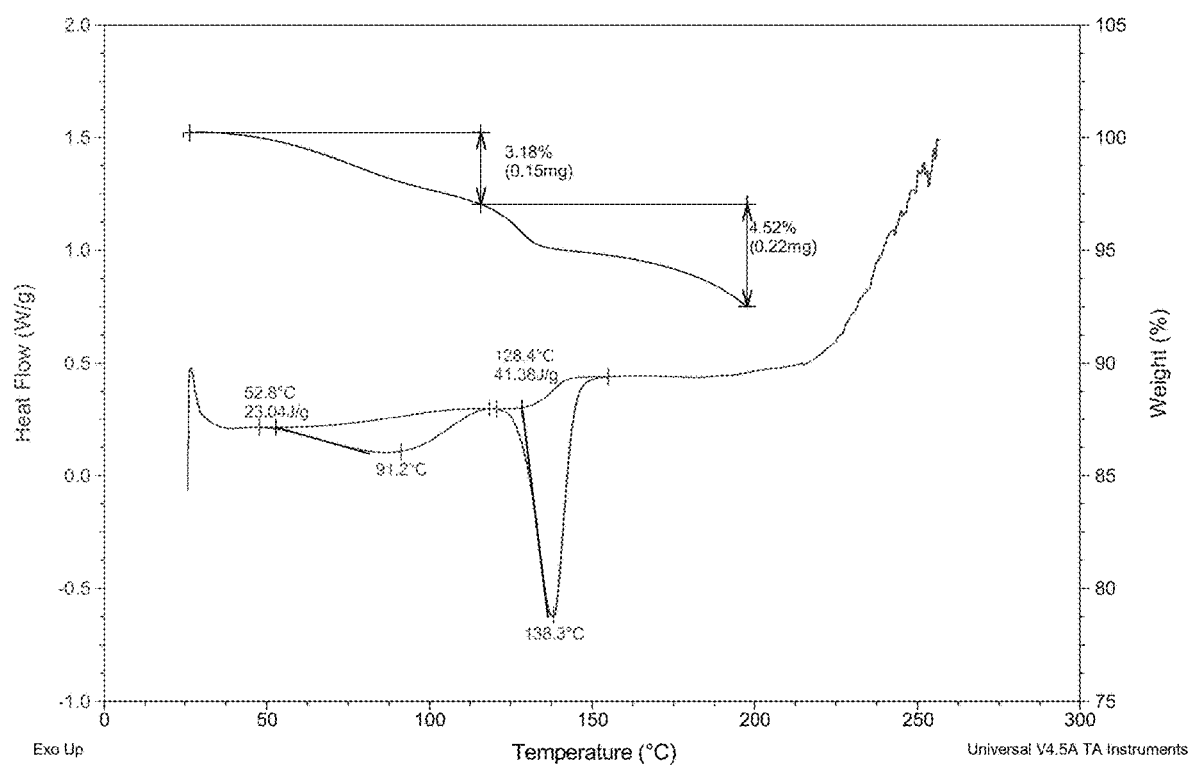

FIG. 12 provides representative DSC and TGA thermograms of Form A of an HBr salt of Compound 1.

Figure 13:
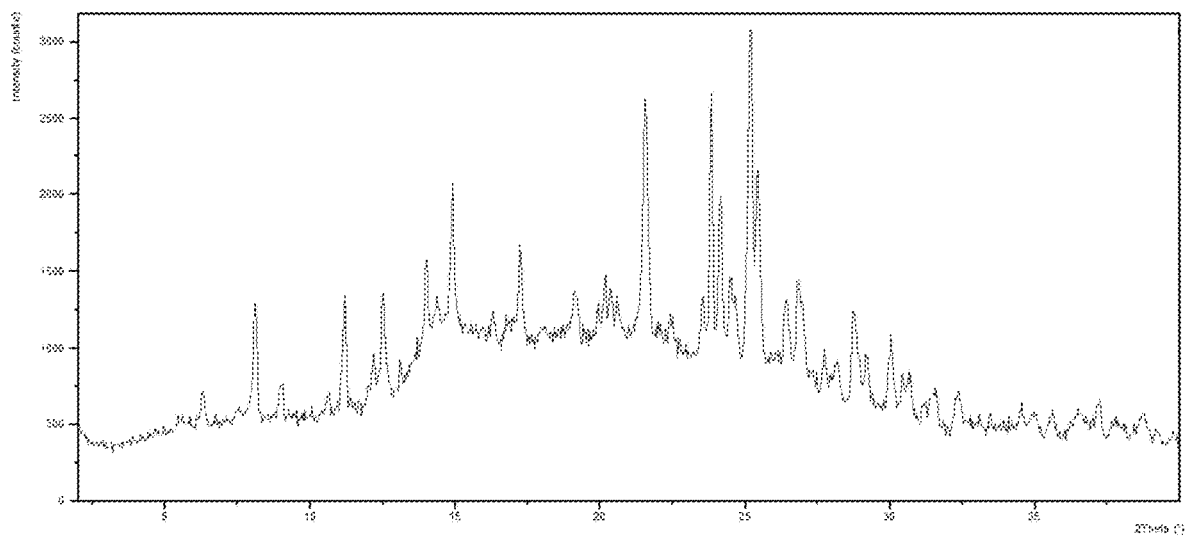

FIG. 13 provides a representative XRPD pattern of Form B of an HBr salt of Compound 1.

Figure 14:
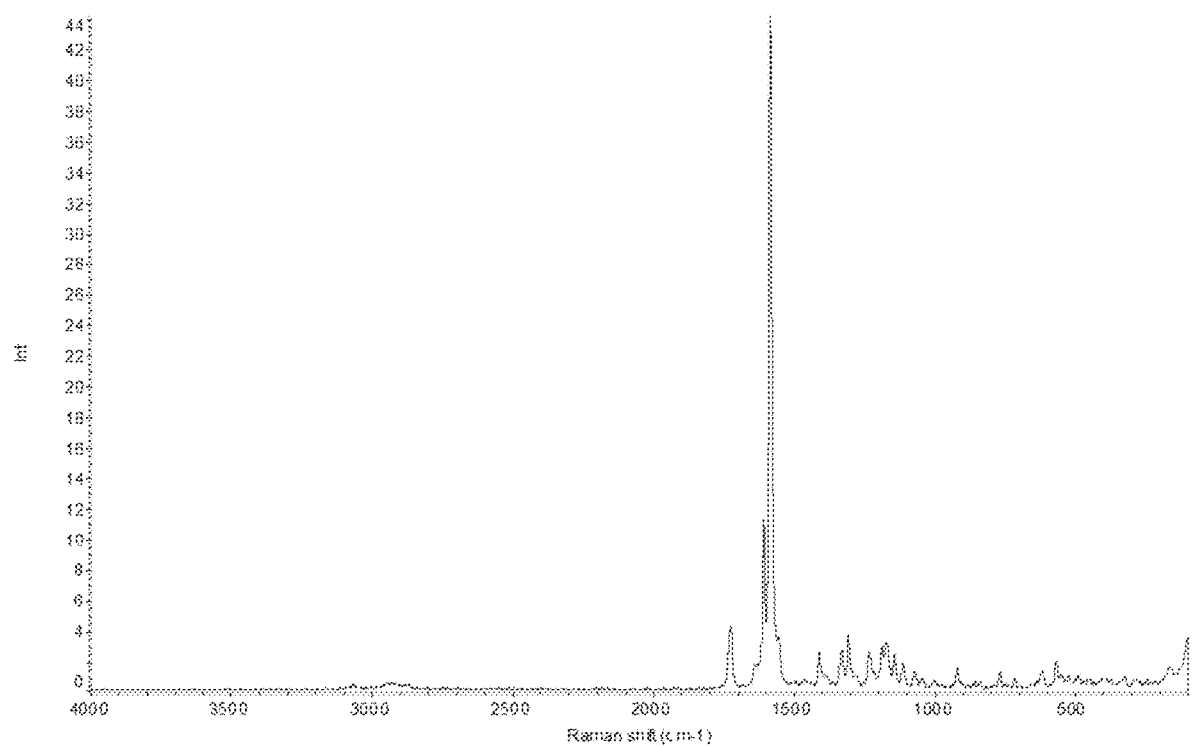

FIG. 14 provides a representative FT-Raman spectrum of Form B of an HBr salt of Compound 1.

Figure 15:
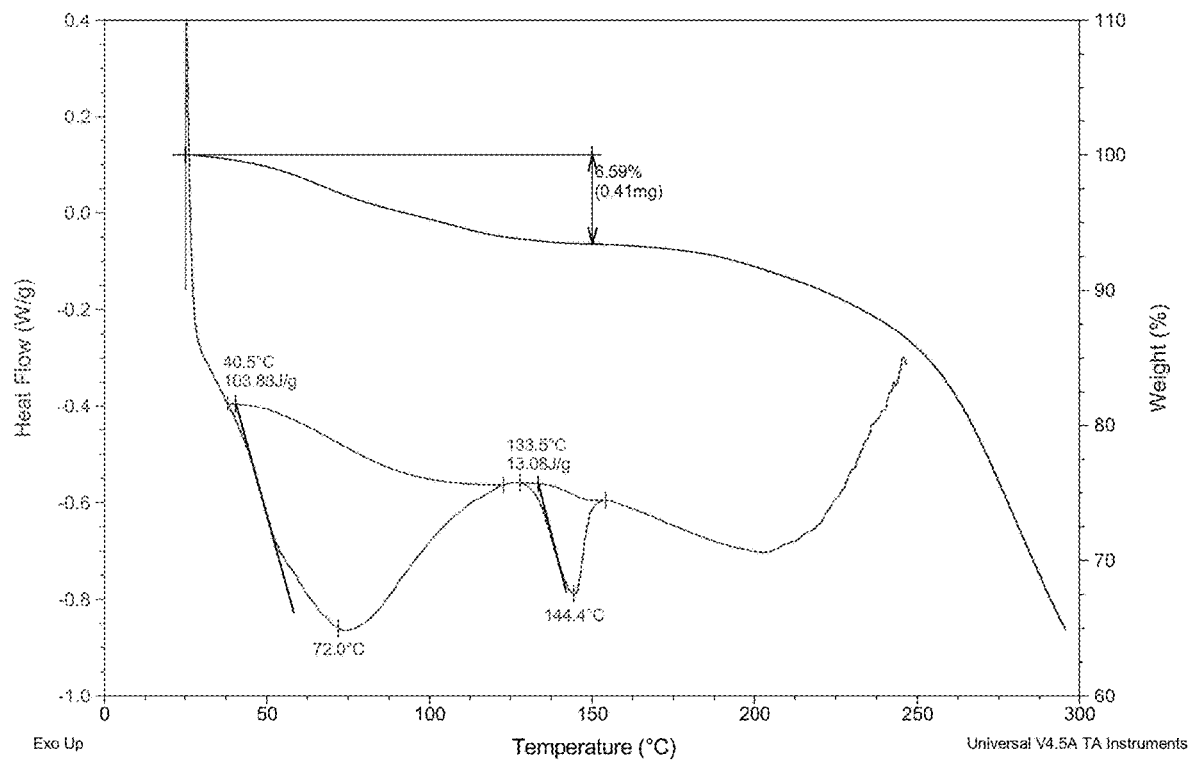

FIG. 15 provides representative DSC and TGA thermograms of Form B of an HBr salt of Compound 1.

Figure 16:
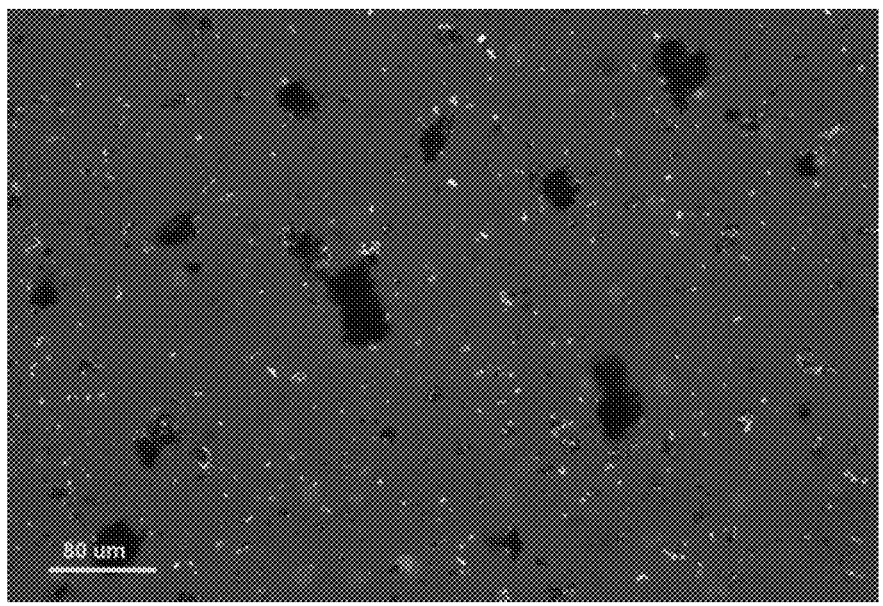

FIG. 16 provides a representative PLM image of Form B of an HBr salt of Compound 1.

Figure 17:
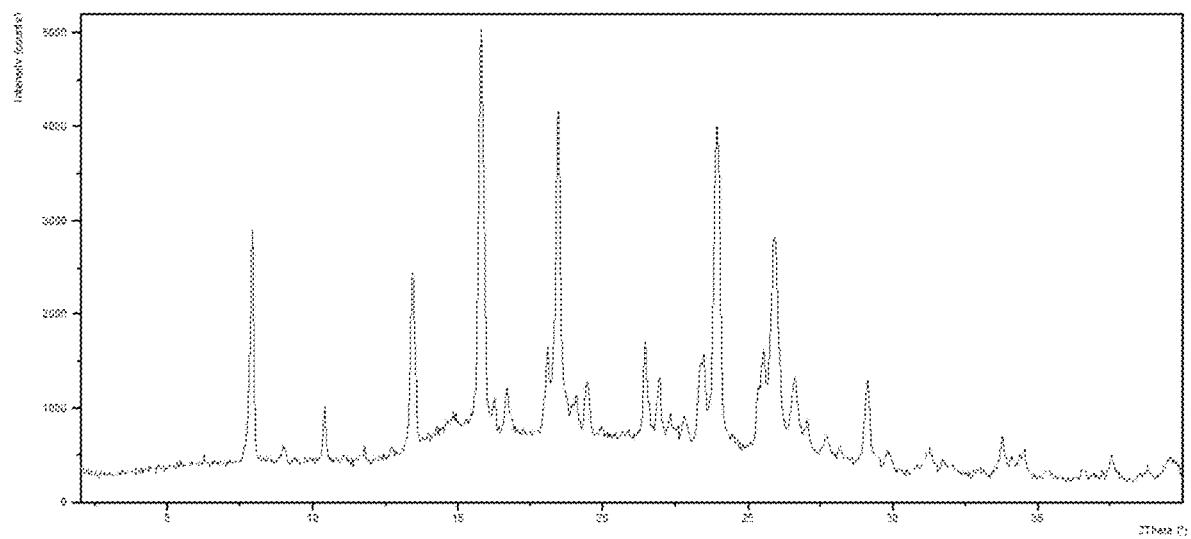

FIG. 17 provides a representative XRPD pattern of Form A of a napadisylate salt of Compound 1.

Figure 18:
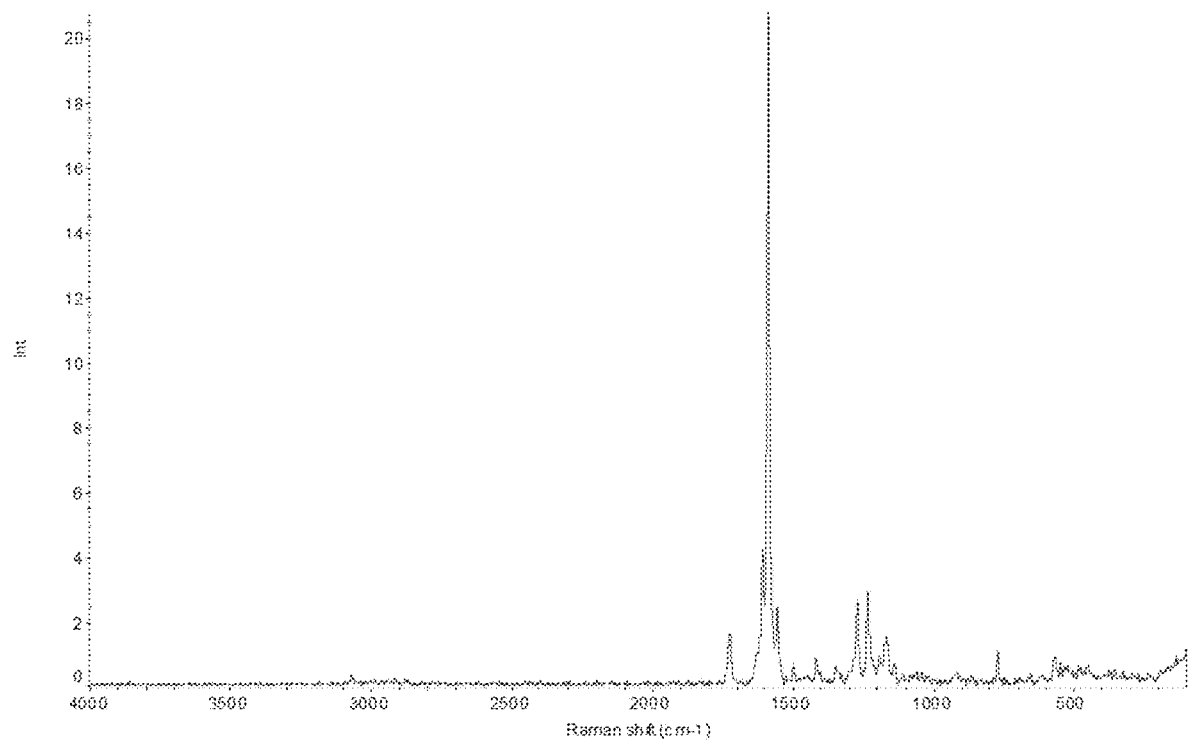

FIG. 18 provides a representative FT-Raman spectrum of Form A of a napadisylate salt of Compound 1.

Figure 19:
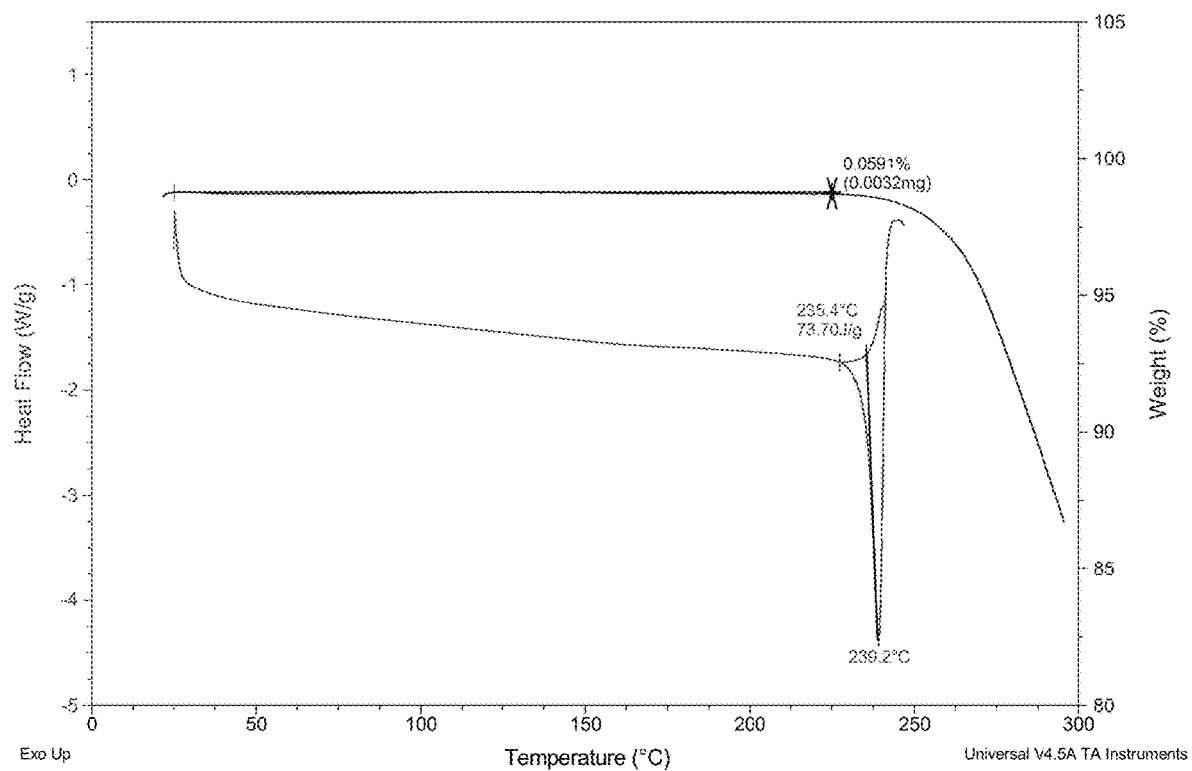

FIG. 19 provides representative DSC and TGA thermograms of Form A of a napadisylate salt of Compound 1.

Figure 20:
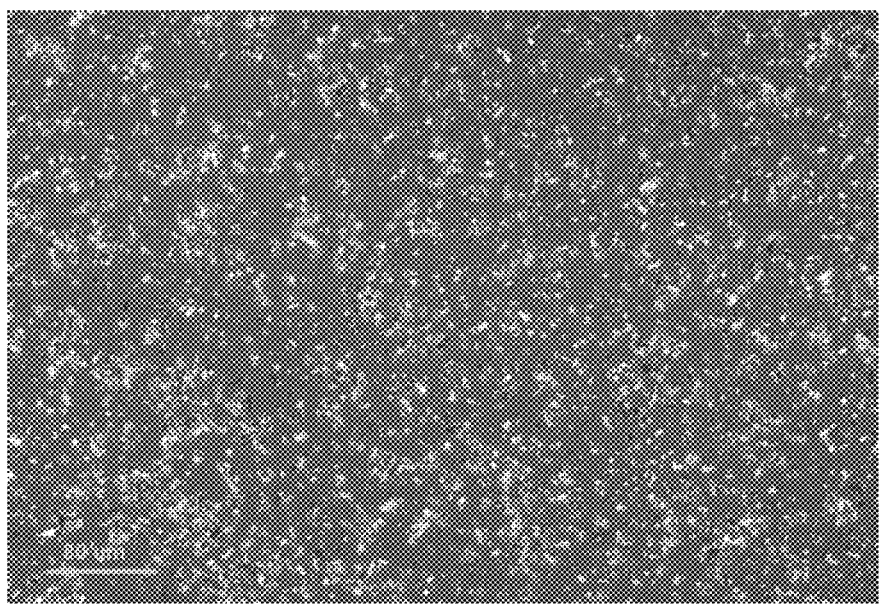

FIG. 20 provides a representative PLM image of Form A of a napadisylate salt of Compound 1.

Figure 21:
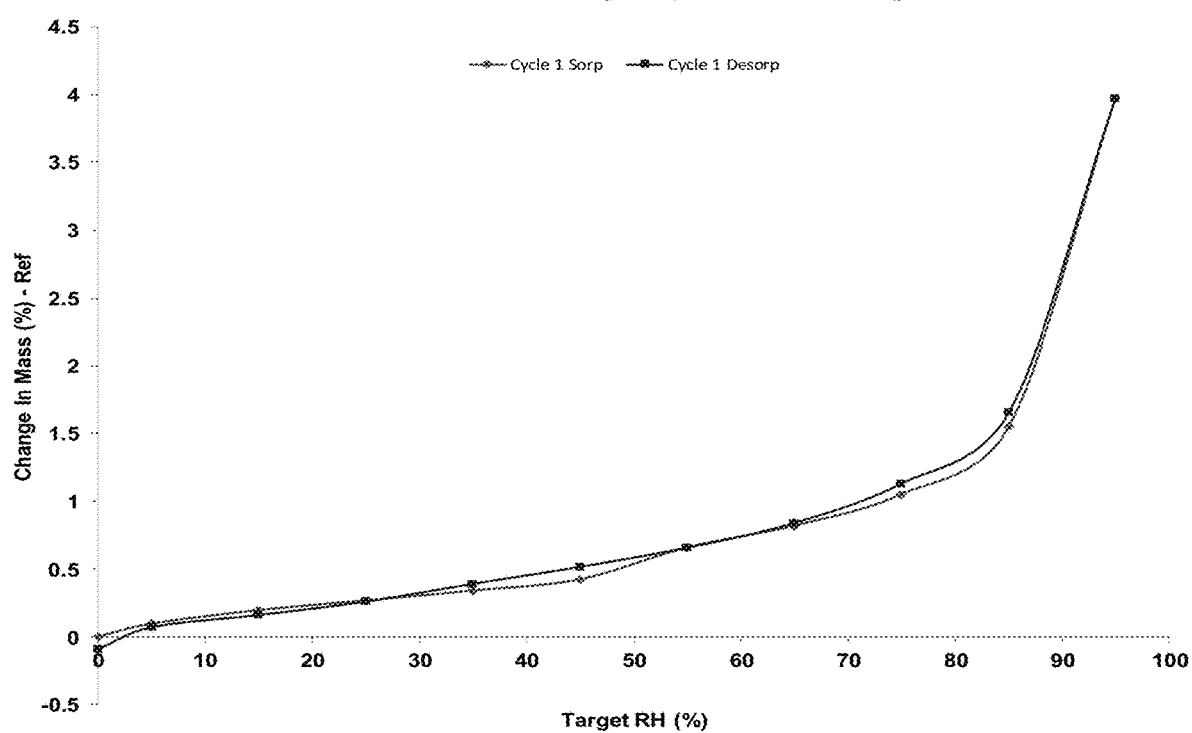

FIG. 21 provides a representative DVS isotherm of Form A of a napadisylate salt of Compound 1.

Figure 22:
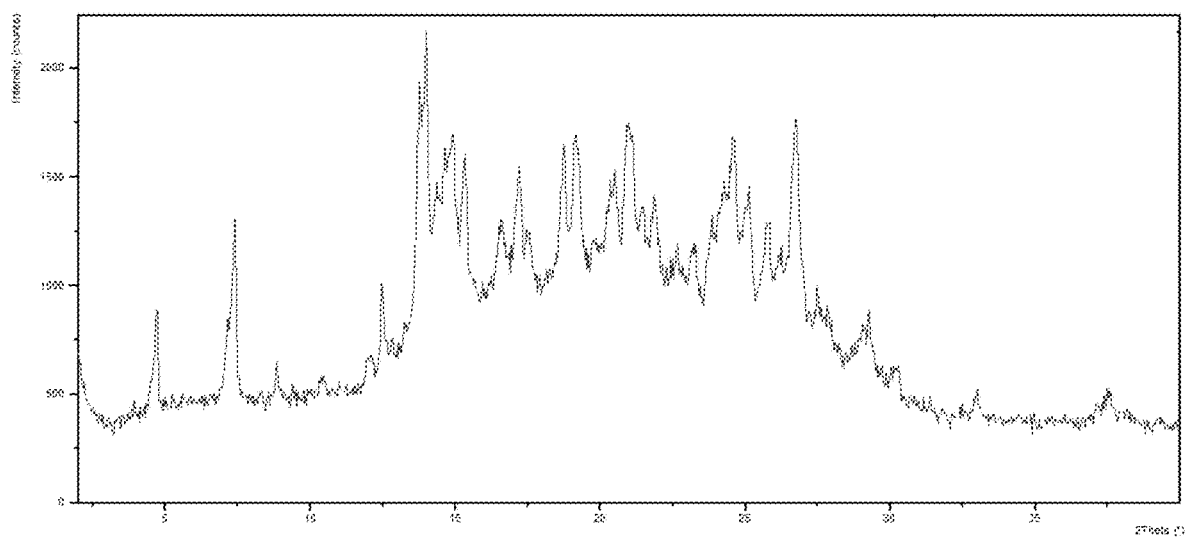

FIG. 22 provides a representative XRPD pattern of Form B of a napadisylate salt of Compound 1.

Figure 23:
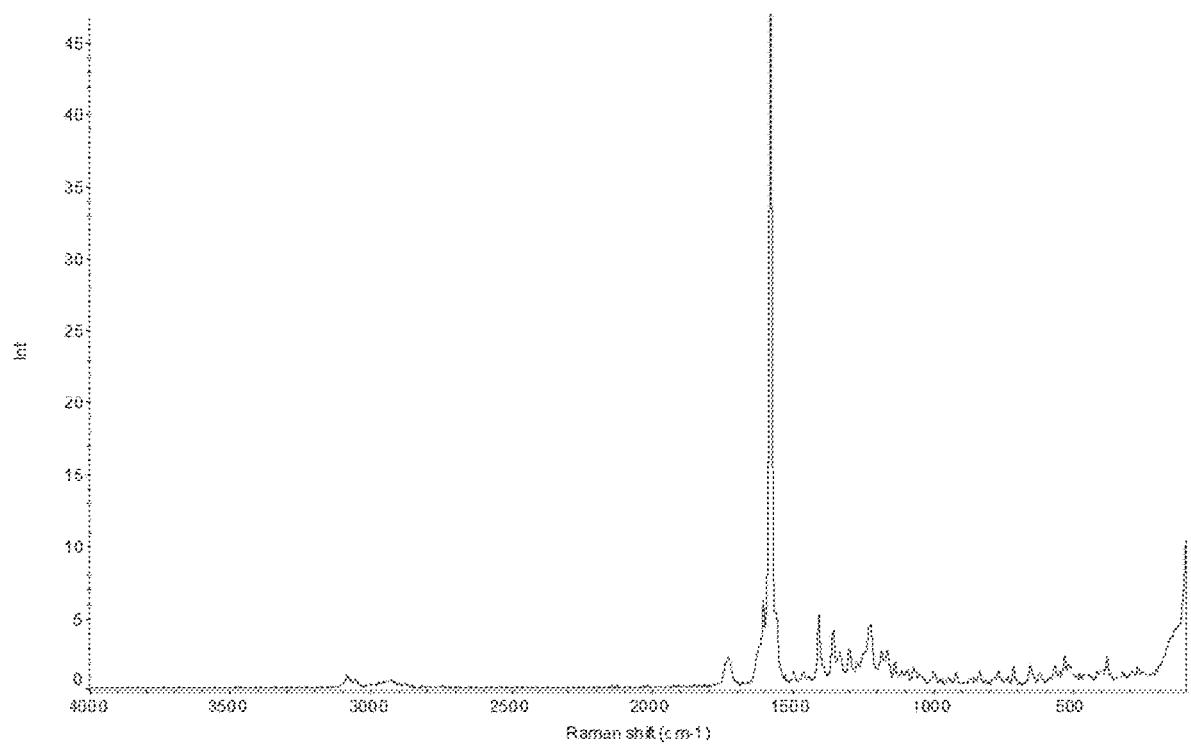

FIG. 23 provides a representative FT-Raman spectrum of Form B of a napadisylate salt of Compound 1.

Figure 24:
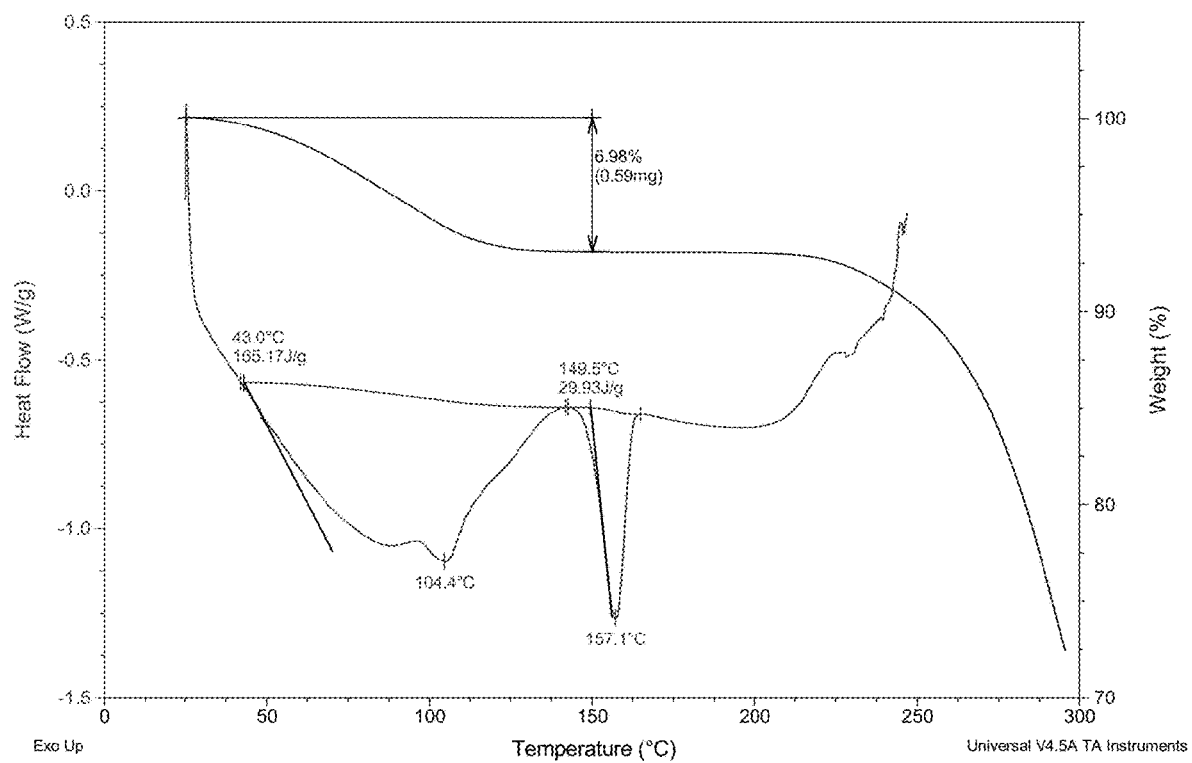

FIG. 24 provides representative DSC and TGA thermograms of Form B of a napadisylate salt of Compound 1.

Figure 25:
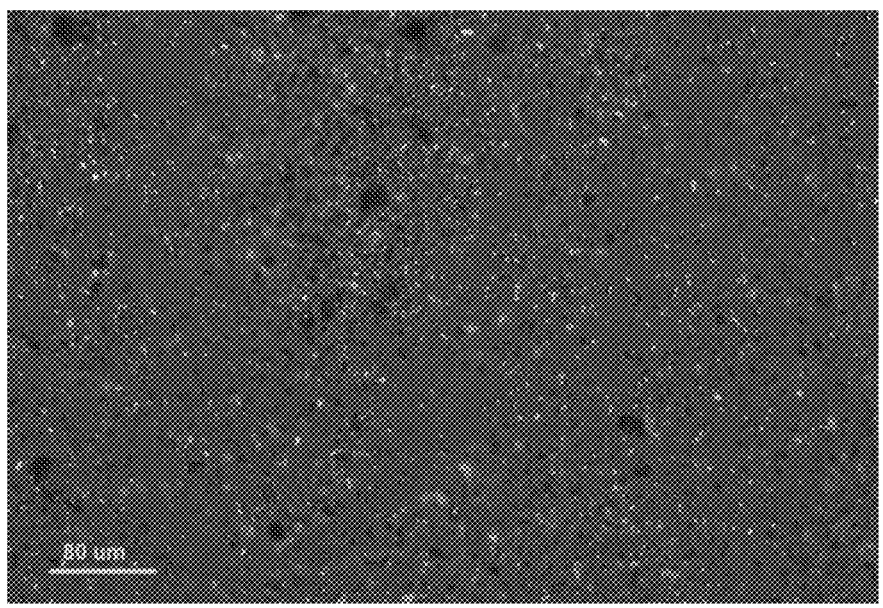

FIG. 25 provides a representative PLM image of Form B of a napadisylate salt of Compound 1.

Figure 26:
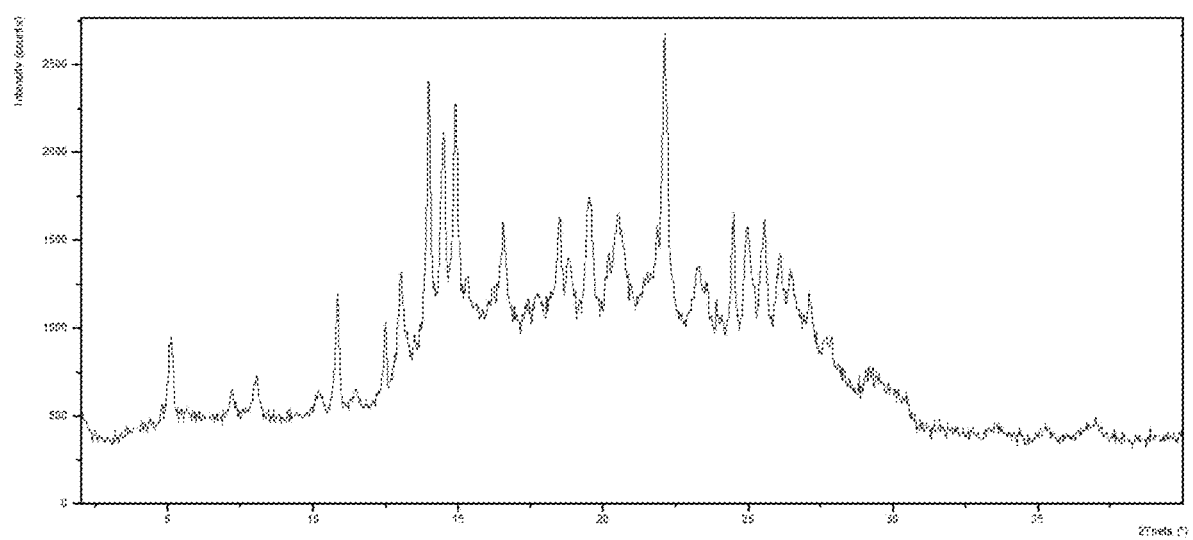

FIG. 26 provides a representative XRPD pattern of Form C of a napadisylate salt of Compound 1.

Figure 27:
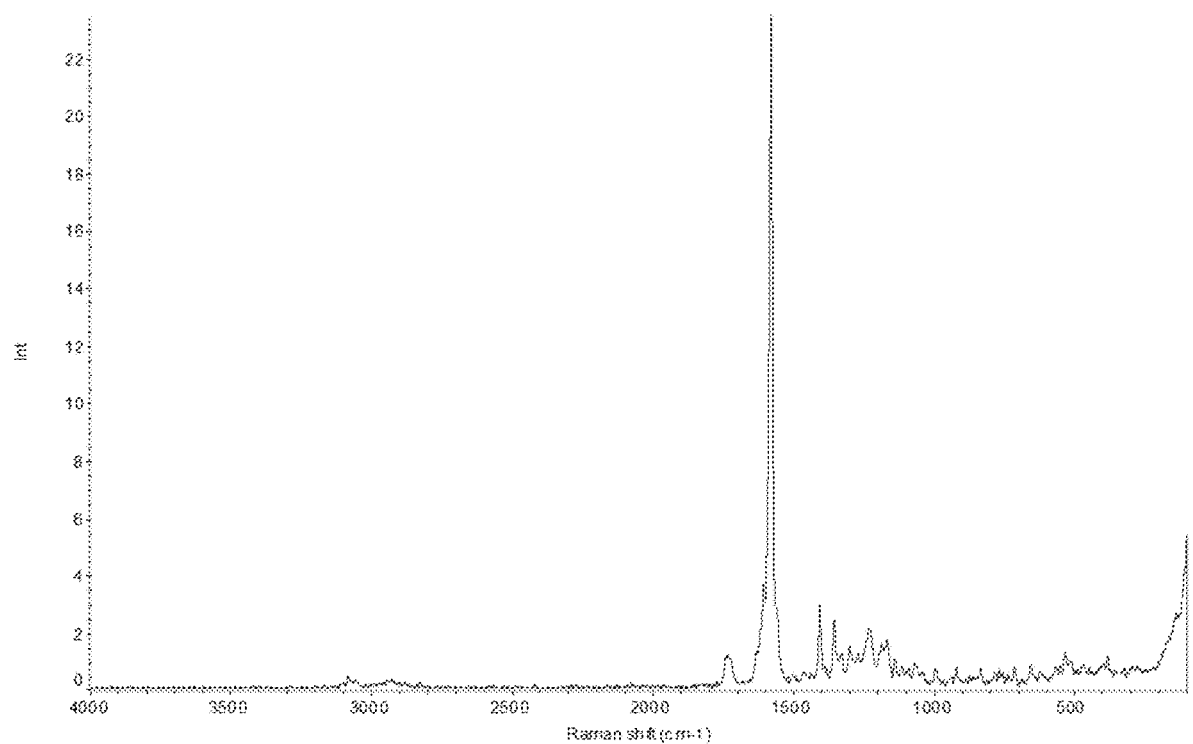

FIG. 27 provides a representative FT-Raman spectrum of Form C of a napadisylate salt of Compound 1.

Figure 28:
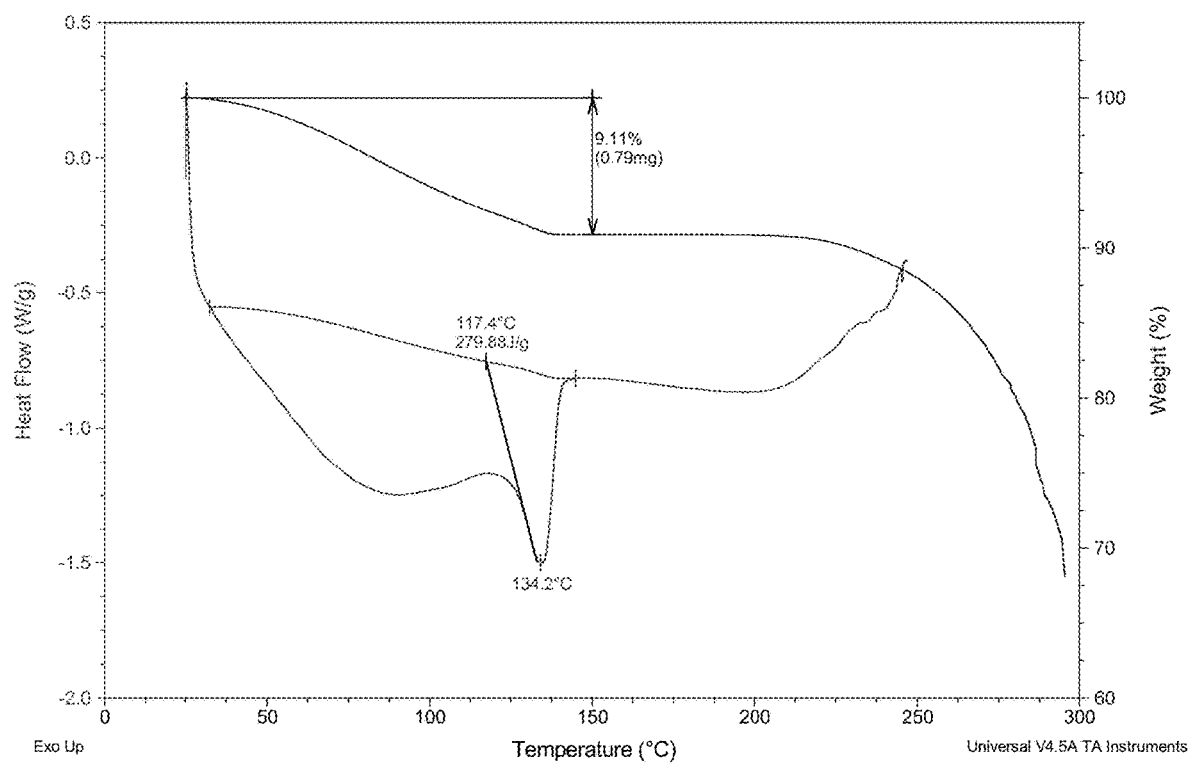

FIG. 28 provides representative DSC and TGA thermograms of Form C of a napadisylate salt of Compound 1.

Figure 29:
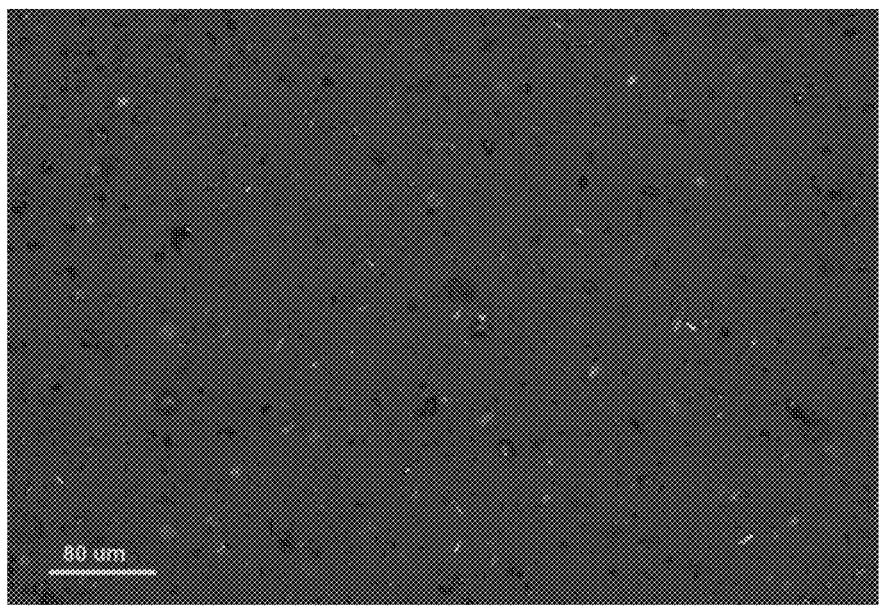

FIG. 29 provides a representative PLM image of Form C of a napadisylate salt of Compound 1.

Figure 30:
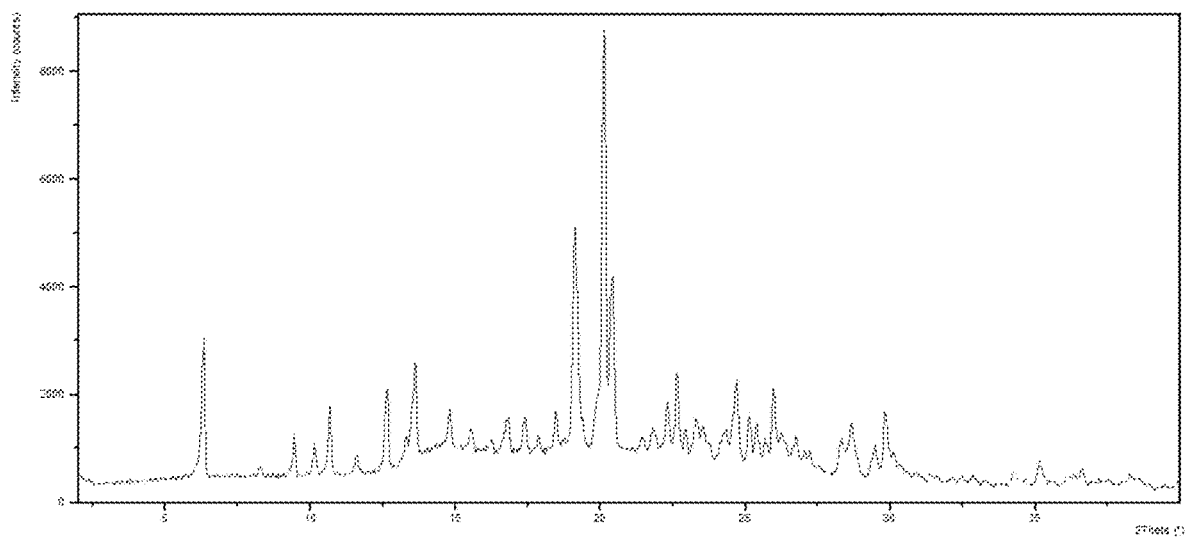

FIG. 30 provides a representative XRPD pattern of Form A of a 2-naphthalenesulfonate salt of Compound 1.

Figure 31:
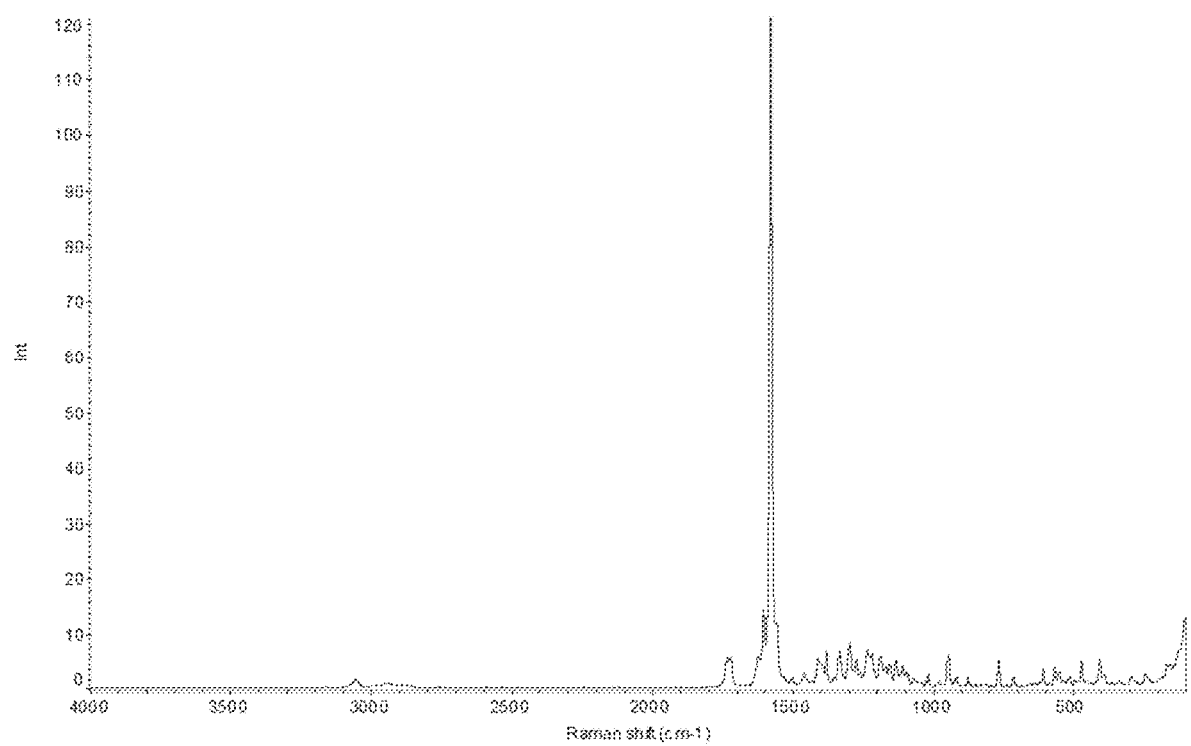

FIG. 31 provides a representative FT-Raman spectrum of Form A of a 2-naphthalenesulfonate salt of Compound 1.

Figure 32:
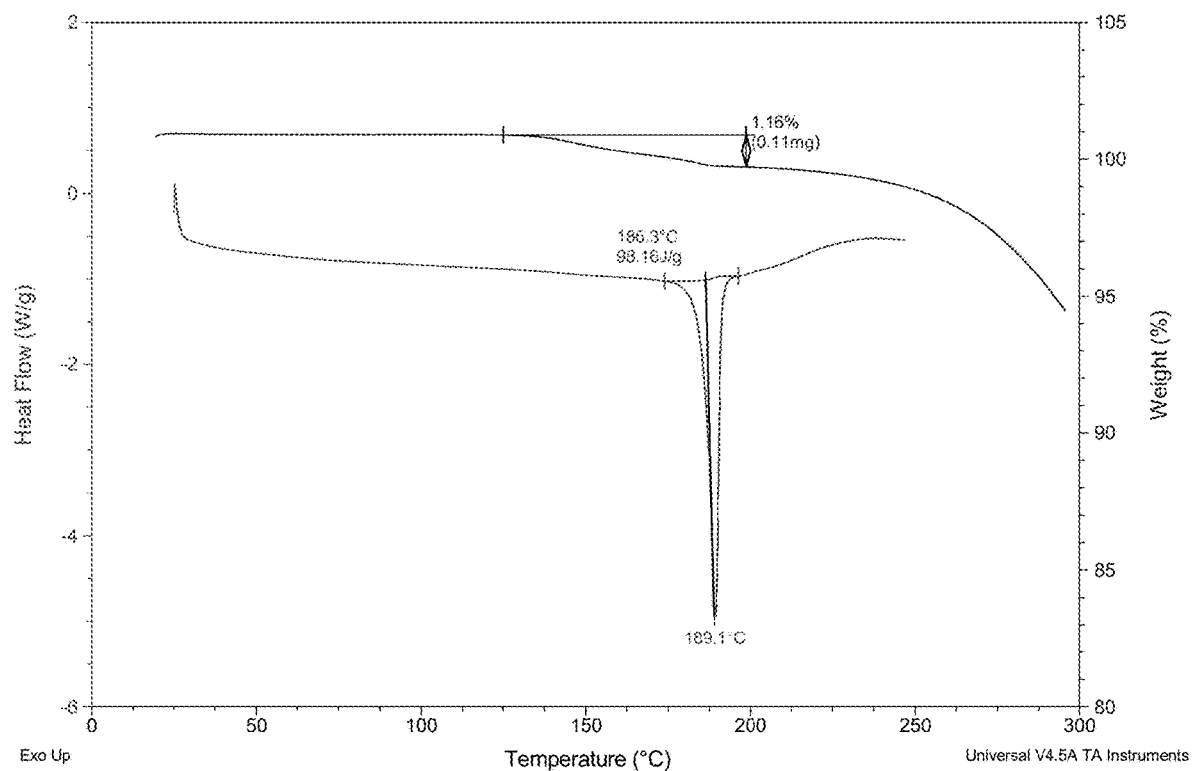

FIG. 32 provides representative DSC and TGA thermograms of Form A of a 2-naphthalenesulfonate salt of Compound 1.

Figure 33:
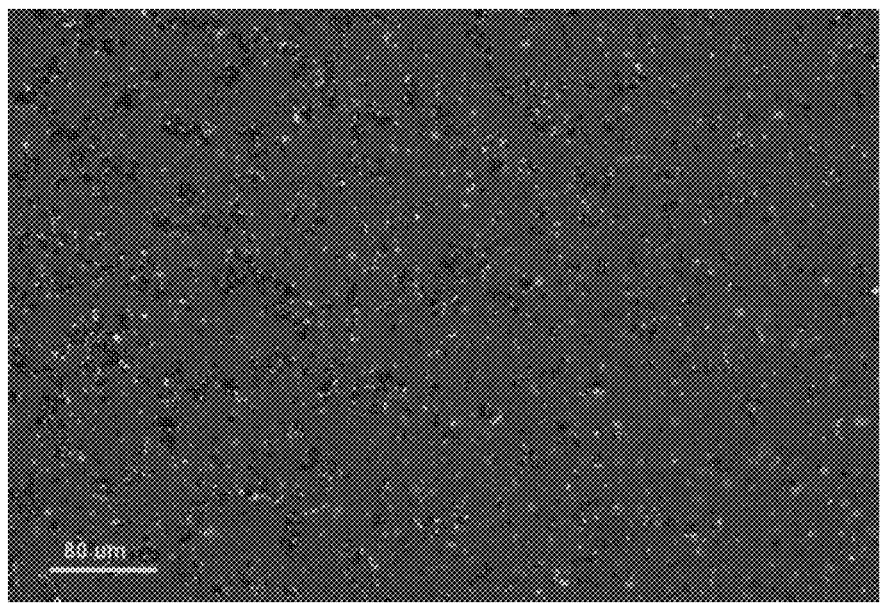

FIG. 33 provides a representative PLM image of Form A of a 2-naphthalenesulfonate salt of Compound 1.

Figure 34:
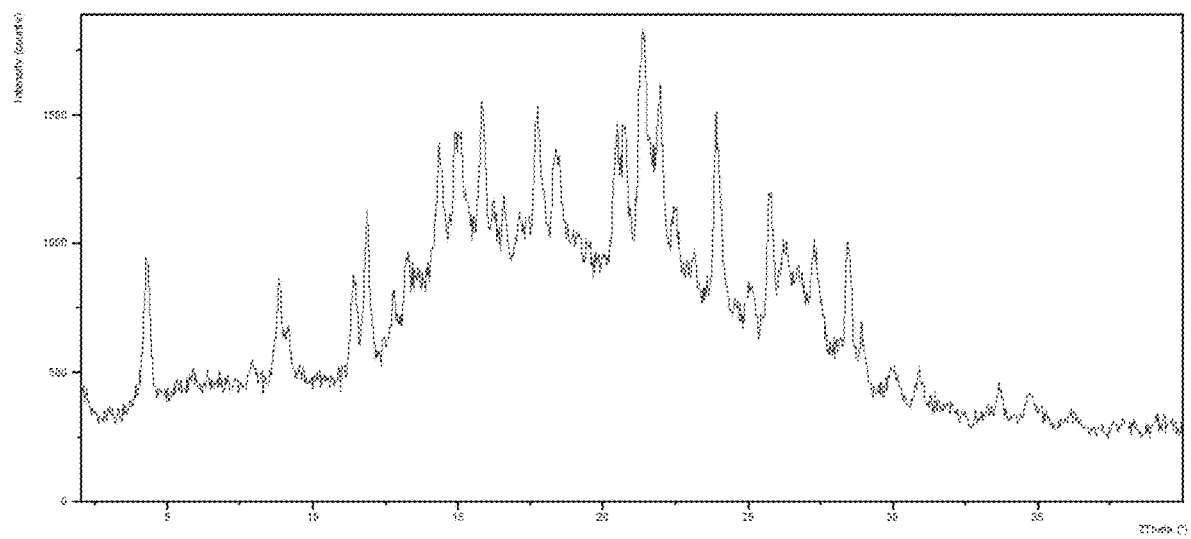

FIG. 34 provides a representative XRPD pattern of Form A of an edisylate salt of Compound 1.

Figure 35:
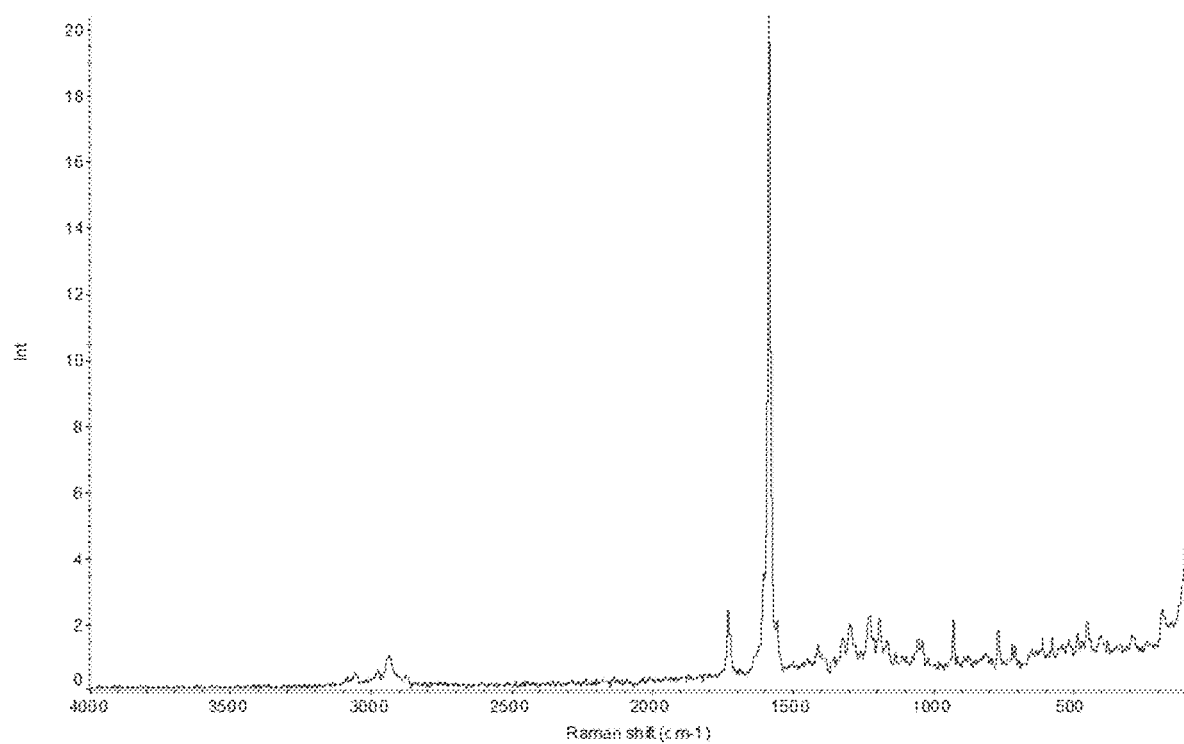

FIG. 35 provides a representative FT-Raman spectrum of Form A of an edisylate salt of Compound 1.

Figure 36:
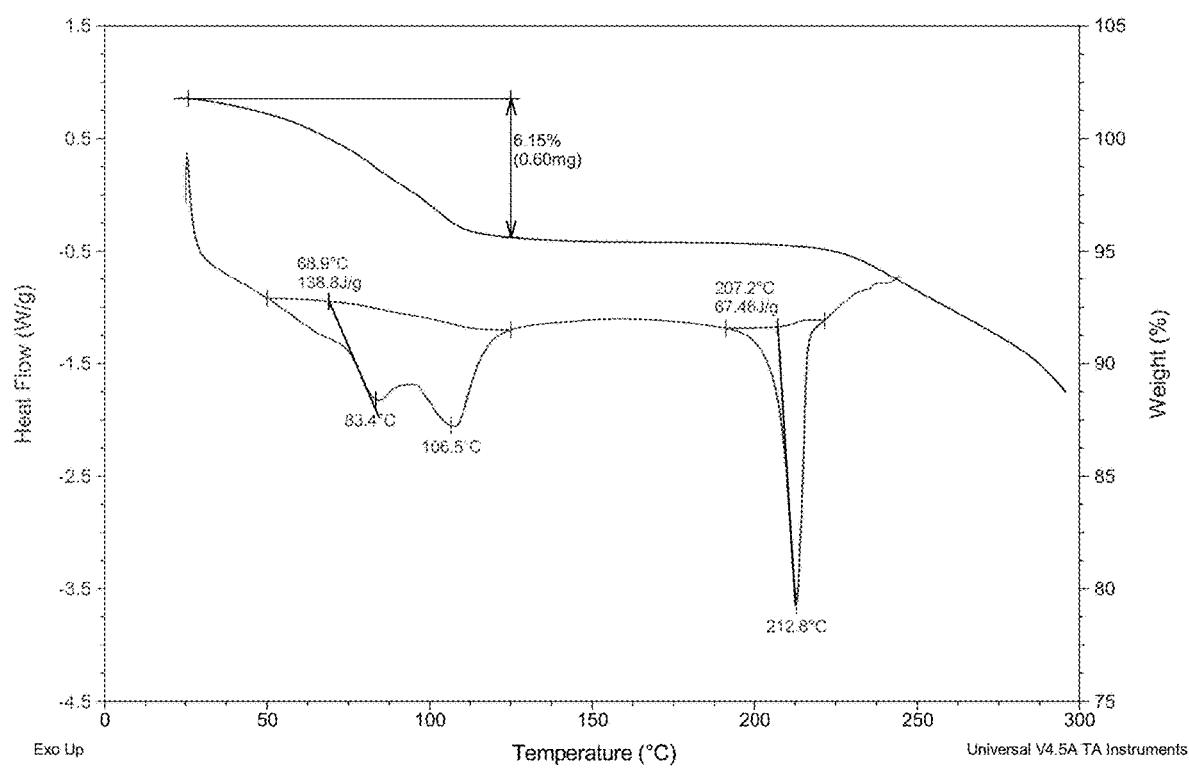

FIG. 36 provides representative DSC and TGA thermograms of Form A of an edisylate salt of Compound 1.

Figure 37:
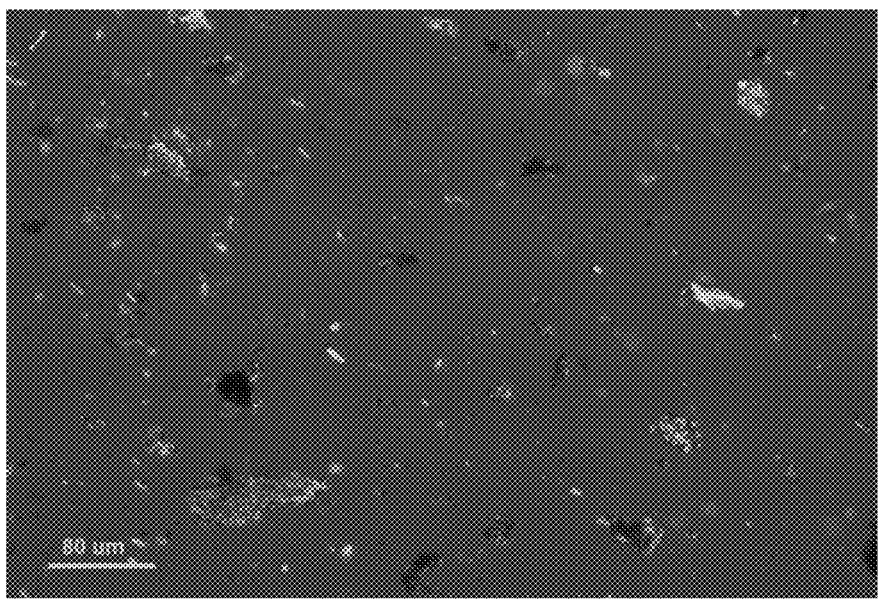

FIG. 37 provides a representative PLM image of Form A of an edisylate salt of Compound 1.

Figure 38:
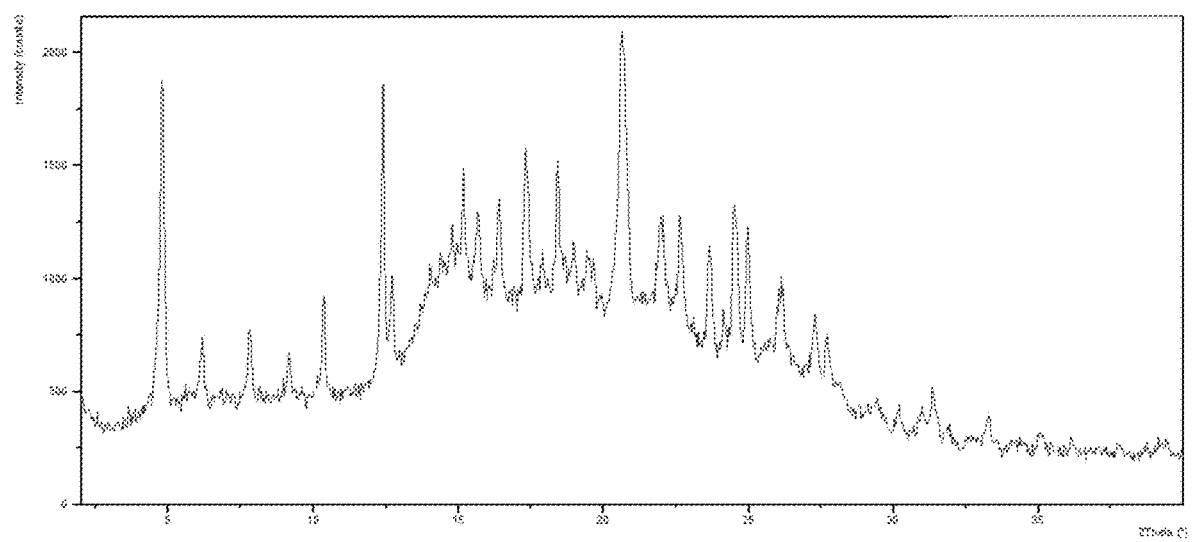

FIG. 38 provides a representative XRPD pattern of Form B of an edisylate salt of Compound 1.

Figure 39:
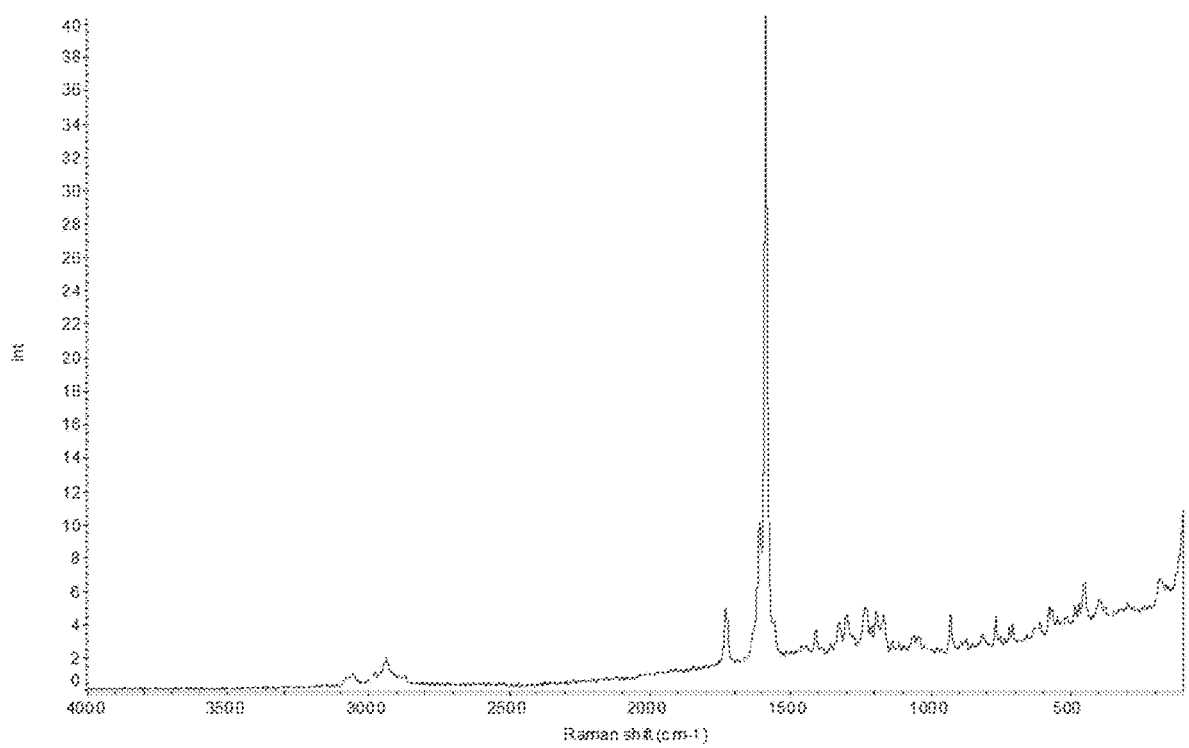

FIG. 39 provides a representative FT-Raman spectrum of Form B of an edisylate salt of Compound 1.

Figure 40:
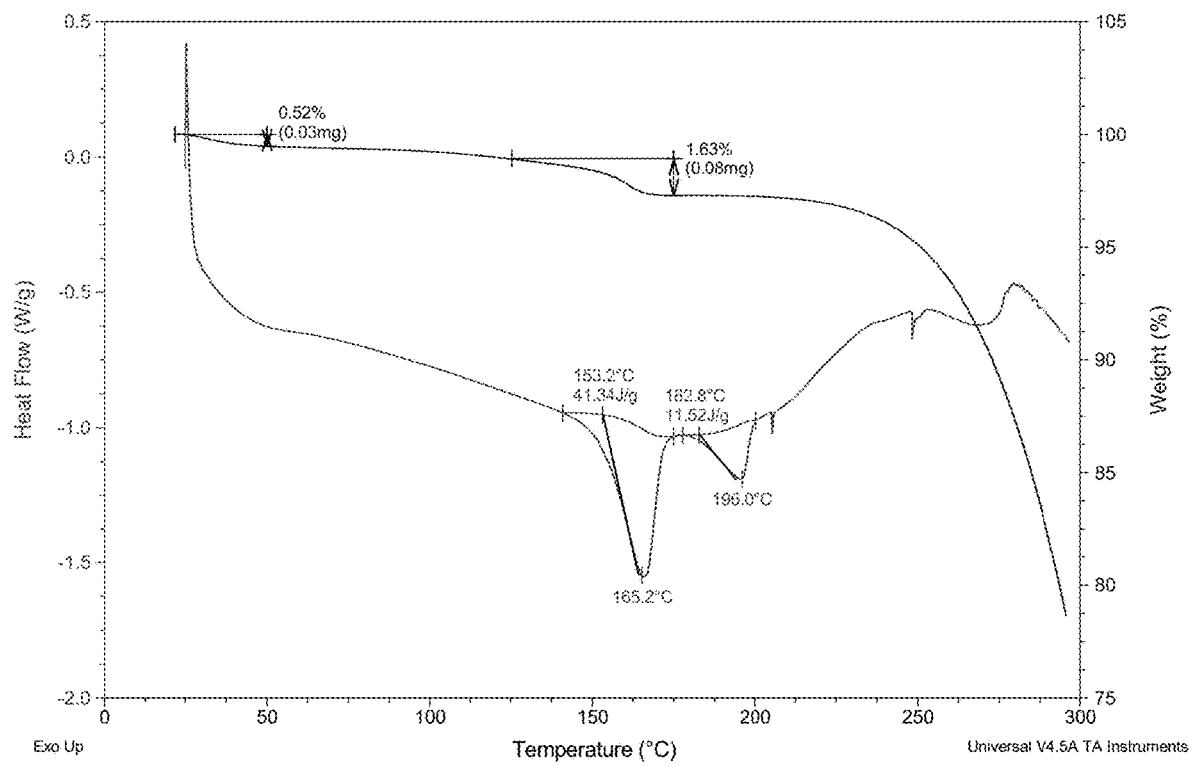

FIG. 40 provides representative DSC and TGA thermograms of Form B of an edisylate salt of Compound 1.

Figure 41:
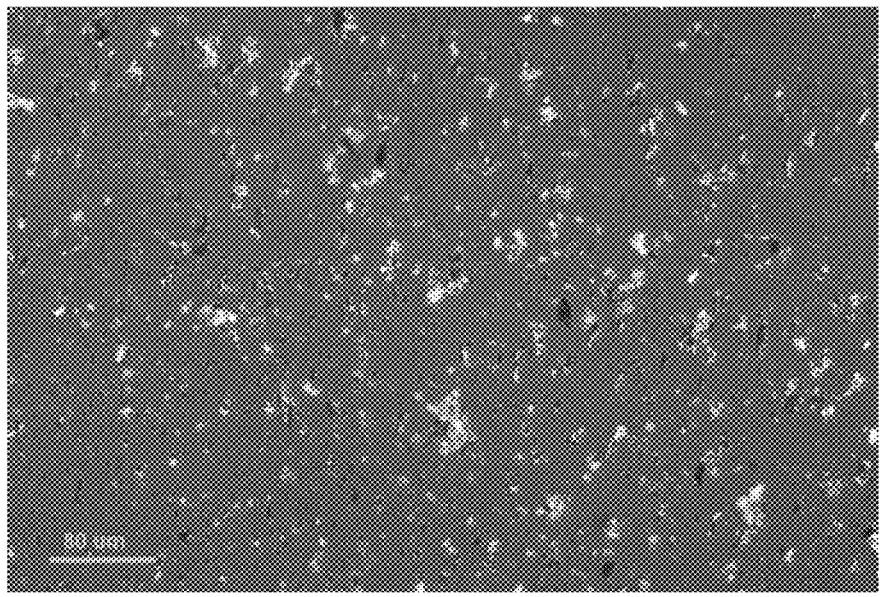

FIG. 41 provides a representative PLM image of Form B of an edisylate salt of Compound 1.

Figure 42:
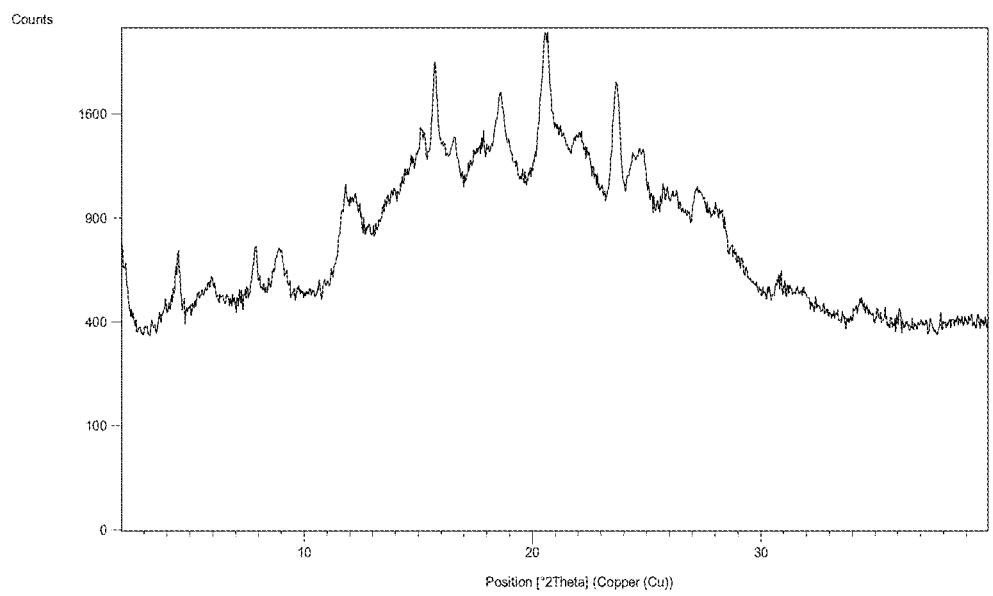

FIG. 42 provides a representative XRPD pattern of Form C of an edisylate salt of Compound 1.

Figure 43:
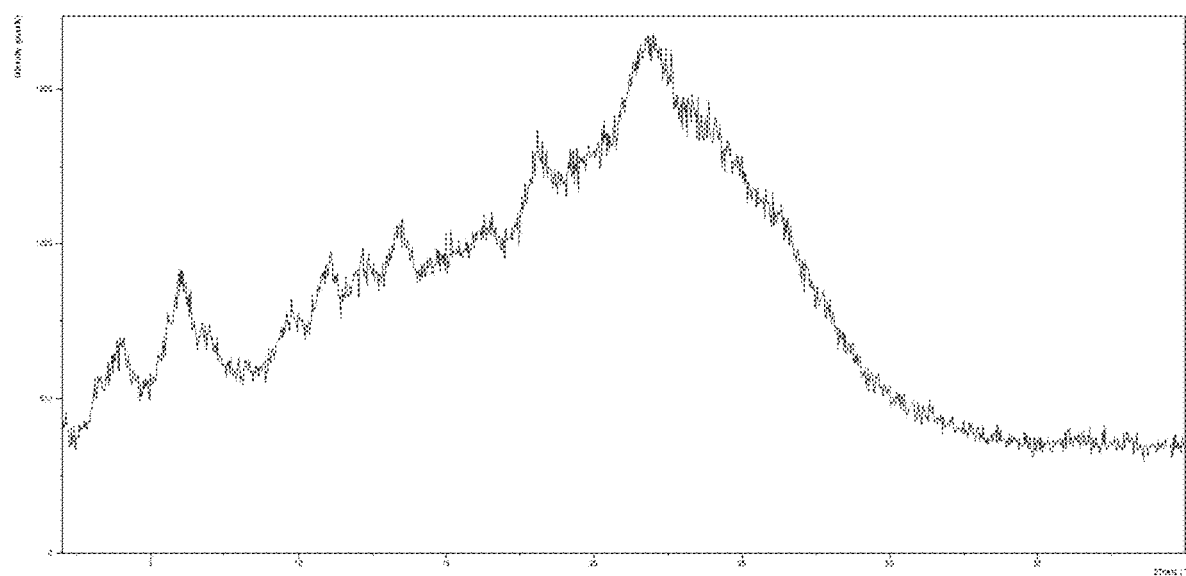

FIG. 43 provides a representative XRPD pattern of the starting material batch of Compound 1 used in crystal salt form screen.

Figure 44:
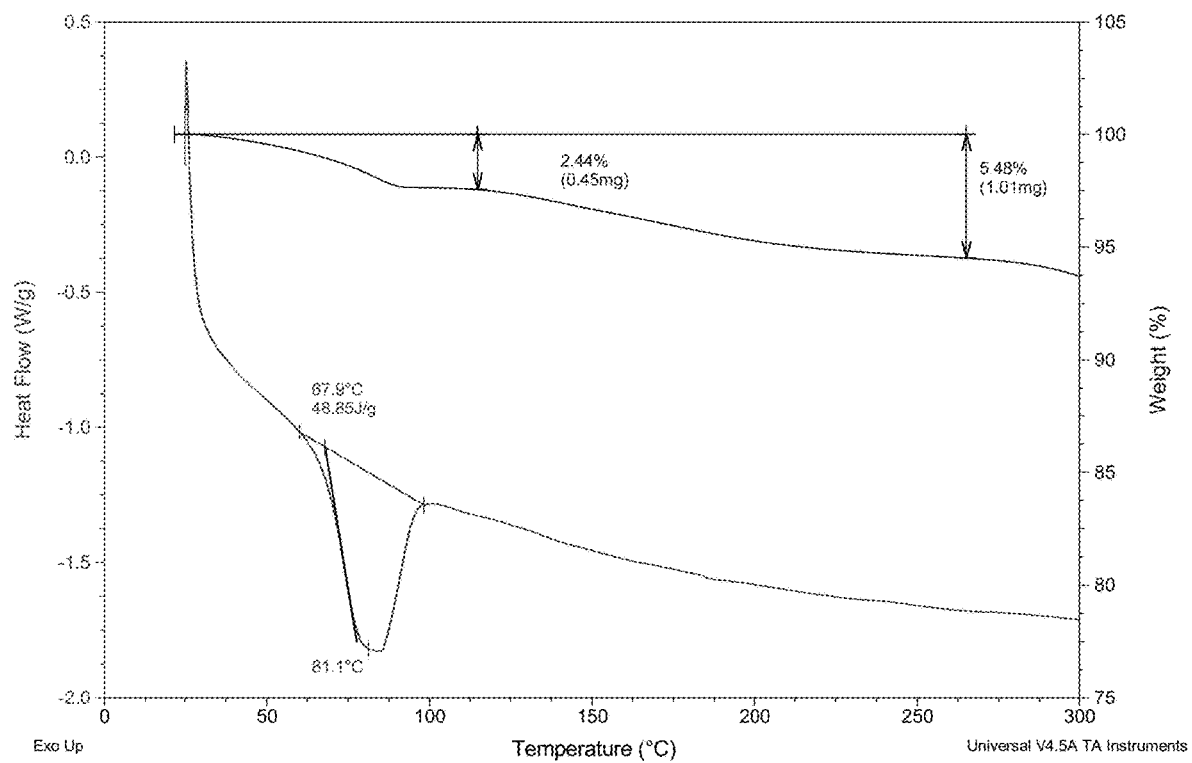

FIG. 44 provides representative DSC and TGA thermograms of the starting material batch of Compound 1 used in crystal salt form screen.

5. DETAILED DESCRIPTION

5.1 Definitions

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, infrared (IR) or Raman spectroscopy or X-ray powder diffraction (PXRD), indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), PXRD, single-crystal X-ray diffraction, vibrational spectroscopy, e.g., IR and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of a PXRD peak position may vary by up to ±0.2 degree two theta (2θ) while still describing the particular PXRD peak. In another embodiment, the value of a PXRD peak position may vary by up to +0.1 degree two theta while still describing the particular PXRD peak.

Unless otherwise specified, the terms "X-ray powder diffraction", "powder X-ray diffraction", "PXRD", and "XRPD" are used interchangeably in this application.

Solid forms may exhibit distinct physical characterization data that are unique to a particular solid form, such as the crystal forms provided herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms provided herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis variation.

As used herein, and unless otherwise specified, a crystalline that is "pure," i.e., substantially free of other crystalline or amorphous solid forms, contains less than about 10% by weight of one or more other crystalline or amorphous solid forms, less than about 5% by weight of one or more other crystalline or amorphous solid forms, less than about 3% by weight of one or more other crystalline or amorphous solid forms, or less than about 1% by weight of one or more other crystalline or amorphous solid forms.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition.

As used herein, and unless otherwise indicated, the term "desolvated solvate" refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

As used herein, and unless otherwise indicated, the term "composition" is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

As used herein, and unless otherwise indicated, the term "solid form" refers to a physical form which is not predominantly in a liquid or a gaseous state. The terms "solid type" and "type" are used interchangeably herein with "solid form". A solid form may be a crystalline form or a mixture thereof. In certain embodiments, a solid form may be a liquid crystal.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

As used herein and unless otherwise specified, the term "crystal form" or "crystalline form" refers to a solid form that is crystalline. In certain embodiments, a crystal form of a substance may be substantially free of amorphous solids and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

As used herein and unless otherwise specified, the term "amorphous" or "amorphous solid form" means that the substance, component, or product in question is not substantially crystalline as determined by X-ray diffraction. In particular, the term "amorphous solid" describes a disordered solid form, i.e., a solid form lacking long range crystalline order. In certain embodiments, an amorphous solid form of a substance may be substantially free of other amorphous solid form and/or crystal forms. In certain embodiments, an amorphous solid form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous solid forms and/or crystal forms on a weight basis. In certain embodiments, an amorphous solid form of a substance may be physically and/or chemically pure. In certain embodiments, an amorphous solid form of a substance be about 99%, about 98%, about 97%, about 96%, about 95%, about 94%, about 93%, about 92%, about 91%, or about 90% physically and/or chemically pure.

As used herein, and unless otherwise indicated, the term "tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

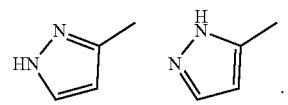

As readily understood by one skilled in the art, a wide variety of functional groups and other structures may exhibit tautomerism.

As used herein, and unless otherwise indicated, the term "zwitterion(s)" means compound(s) containing both a basic moiety, including but not limited to, for example, pyridine and imidazole; and an acidic moiety including but not limited to, for example, a carboxylic acid.

As used herein, the compound "(2Z,5Z)-5-(3-chloro-4-[(2R)-2,3-dihydroxypropoxy]benzylidene)-3-(2-methylphenyl)-2-(propylimino)-1,3-thiazolidin-4-one", the compound "(Z)-5-((Z)-3-chloro-4-((R)-2,3-dihydroxypropoxy)benzylidene)-2-(propylimino)-3-(o-tolyl)thiazolidin-4-one", or Compound 1 has the following structure:

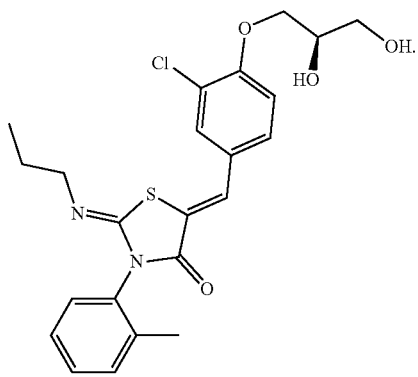 [SMILES: CCC/N=C1\S/C(=C\c2ccc(OC[C@H](O)CO)c(Cl)c2)C(=O)N1c1ccccc1C]

As used herein, and unless otherwise indicated, the term "treating" means an alleviation, in whole or in part, of the disease or disorder, or symptoms associated with the disease or disorder, or slowing, or halting of further progression or worsening of the disease or disorder, or symptoms associated with the disease or disorder.

As used herein, and unless otherwise indicated, the term "preventing" means prevention of the onset, recurrence, or spread of the disease or disorder, or symptoms associated with the disorder or disease, in a patient at risk for developing the disease or disorder.

As used herein, and unless otherwise specified, the term "therapeutically effective amount" of a compound refers to an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human, in another embodiment a cell from any one of the foregoing animals. In one embodiment, a subject or patient is a non-human animal, in another embodiment a non-human mammal. In another embodiment, a subject or patient is a human having or at risk for having an autoimmune or chronic inflammatory disease. In certain embodiments, the autoimmune or chronic inflammatory disease is polymyositis, dermatomyositis, lupus nephritis, rheumatoid arthritis, inflammatory bowel disease, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease or multiple sclerosis. In certain embodiments, provided herein are methods for treating a subject suffering from or at risk for having relapsing-remitting multiple sclerosis, primary progressive multiple sclerosis, secondary progressive multiple sclerosis, and relapsing secondary progressive multiple sclerosis. In certain embodiments, a subject or patient is a human having or at risk for having a neurological disorder. In certain embodiments, the neurological disorder is Rett Syndrome. In certain embodiments, a subject or patient is a human having or at risk for having renal or hepatic impairment. In certain embodiments, a subject or patient is a human having or at risk for having a disease or disorder associated with sphingosine 1-phosphate, including but not limited to multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, and Graves' disease. In certain embodiments, a subject or patient is a human having or at risk for having a disease or disorder associated with the interferon alpha receptor 1, including but not limited to psoriasis, ulcerative colitis, systemic lupus, multiple sclerosis, and rheumatoid arthritis. In certain embodiments, a subject or patient is a human having a disease or disorder mediated by lymphocyte interactions, such as, for example, in transplantation, such as acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus.

Unless otherwise specified, to the extent that there is a discrepancy between a depicted chemical structure of a compound provided herein and a chemical name of a compound provided herein, the chemical structure shall control.

5.2 Compound 1 and Salts

The solid forms, formulations, and methods of use provided herein relate to solid forms (e.g., crystalline forms, amorphous forms, polymorphs or mixtures thereof) comprising a salt of Compound 1:

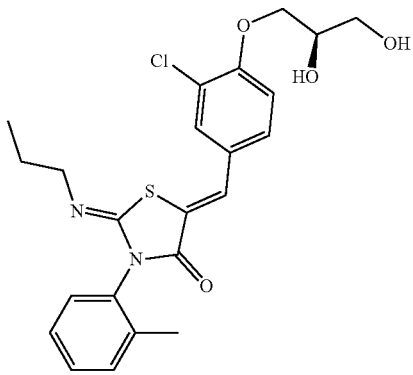

1 having the name (Z)-5-((Z)-3-chloro-4-((R)-2,3-dihydroxypropoxy)benzylidene)-2-(propylimino)-3-(o-tolyl)thiazolidin-4-one. The solid forms provided herein also include solid forms comprising a salt of a tautomer of Compound 1. Compound 1 can be prepared by methods known in the art. See, e.g., International Patent Application Publication No. WO 2005/054215.

Also provided herein are salts of Compound 1. In one embodiment, provided herein is an HCl salt of Compound 1. In one embodiment, provided herein is an HBr salt of Compound 1. In one embodiment, provided herein is a napadisylate salt (i.e., a naphthalene-1,5-disulfonic acid salt) of Compound 1. In one embodiment, provided herein is a sulfuric acid salt of Compound 1. In one embodiment, provided herein is an edisylate salt (i.e., an ethane-1,2-disulfonic acid salt) of Compound 1. In one embodiment, provided herein is a camphor-10-sulfonic acid salt of Compound 1. In one embodiment, provided herein is an ethanesulfonic acid salt of Compound 1. In one embodiment, provided herein is a p-toluenesulfonic acid salt of Compound 1. In one embodiment, provided herein is a trifluoroacetic acid salt of Compound 1. In one embodiment, provided herein is a methanesulfonic acid salt of Compound 1. In one embodiment, provided herein is a naphthalene-2-sulfonic acid salt (i.e., a 2-naphthalenesulfonate salt) of Compound 1. In one embodiment, provided herein is a benzenesulfonic acid salt of Compound 1.

5.3 Solid Forms of Salts of Compound 1

In certain embodiments, provided herein are solid forms comprising a salt of Compound 1. In certain embodiments, the solid form is crystalline. In certain embodiments, the solid form is a hydrate. In certain embodiments, the solid form is an anhydrate. In certain embodiments, the solid form is a solvate. In certain embodiments, the solid form is non-solvated.

In certain embodiments, the solid form comprises an HCl salt of Compound 1. In certain embodiments, the solid form comprises an HBr salt of Compound 1. In certain embodiments, the solid form comprises a napadisylate salt of Compound 1. In certain embodiments, the solid form comprises a 2-naphthalenesulfonate salt of Compound 1. In certain embodiments, the solid form comprises an edisylate salt of Compound 1.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art. While not intending to be bound by any particular theory, certain solid forms provided herein exhibit suitable pharmaceutical properties, e.g., pharmaceutical kinetics, pharmaceutical dynamics, half-life, $C_{max}$, and bioavailability. Such properties can be determined using assays known to the skilled artisan.

The solid forms provided herein (e.g., Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, or Form C of an edisylate salt of Compound 1) may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, high performance liquid chromatography (HPLC), and mass spectrometry.

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ or +0.1° 2θ (see, United States Pharmacopoeia, page 2228 (2003)).

(a) Methods of Preparing Solid Forms

In certain embodiments, a solid form provided herein is prepared by slurrying a salt of Compound 1 in a solvent. In one embodiment, a solid form provided herein is prepared by slurrying a salt of Compound 1 (e.g., an amorphous form of the salt of Compound 1) in a solvent for a period of time (e.g., about 48 h) while cycling the temperature (e.g., between about 5° C. and about 40° C.). In certain embodiments, provided herein are methods for making a solid form comprising a salt of Compound 1, comprising 1) obtaining a slurry of the salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide a solid form comprising a salt of Compound 1. In certain embodiments, the methods for making a solid form comprising a salt of Compound 1 are equilibration experiments, such as slurry experiments. In certain embodiments, the collected solids are dried using a flow of an inert gas, such as nitrogen or argon. In certain embodiments, the collected solids are dried under vacuum at a certain temperature (e.g., room temperature or about 40° C.). In a particular embodiment, the collected solids are dried using a combination of a flow of an inert gas, such as nitrogen or argon, under vacuum at a certain temperature (e.g., room temperature or about 40° C.).

In certain embodiments, a salt of Compound 1 (e.g., an amorphous form of the salt of Compound 1 used to prepare a solid form provided herein) is prepared by slurrying a free base of Compound 1 and an acid (e.g., one stoichiometric equivalent) in a solvent for a period of time (e.g., about 48 h) while cycling the temperature (e.g., between about 5° C. and about 40° C.), optionally followed by rapid evaporation.

In certain embodiments, a salt of Compound 1 is prepared by slurrying a free base of Compound 1 and an acid (e.g., 0.5 stoichiometric equivalent) in a solvent for a period of time (e.g., about 48 h) at ambient temperature. In one embodiment, the solids from the slurry are recovered by filtration and dried (e.g., in vacuum oven at 40° C. overnight) to provide a solid form comprising a salt of Compound 1.

(b) Hydrochloride Salt of Compound 1

In some embodiments, provided herein is a hydrochloride salt of Compound 1. It is contemplated that a hydrochloride salt of Compound 1 can exist in a variety of solid forms. Such solid forms include crystalline solids, such as polymorphs, solvates and hydrates of crystalline hydrochloride salt of Compound 1, as well as amorphous solids, or mixtures thereof.

In one embodiment, provided herein is a solid form comprising a hydrochloride salt of Compound 1. In one embodiment, the solid form is a solvate of a hydrochloride salt of Compound 1. In one embodiment, the solid form is a hydrate of a hydrochloride salt of Compound 1. In one embodiment, the solid form is a non-solvated form of a hydrochloride salt of Compound 1. In one embodiment, the solid form is an anhydrate of a hydrochloride salt of Compound 1.

In some embodiments, the molar ratio of Compound 1 to hydrochloric acid in the solid form ranges from about 1:1 to about 1:2. In one embodiment, the molar ratio is about 1:2 (i.e., bis-hydrochloride salt). In another embodiment, the molar ratio is about 1:1 (i.e., mono-hydrochloride salt).

(i) Form A of Hydrochloride Salt of Compound 1

In certain embodiments, provided herein is Form A of a hydrochloride salt of Compound 1.

In one embodiment, Form A is crystalline. In one embodiment, Form A is substantially crystalline.

In one embodiment, the molar ratio of Compound 1 to hydrochloric acid in Form A is about 1:1. In one embodiment, Form A is a mono-hydrochloride salt of Compound 1.

In one embodiment, Form A is a hydrate of a hydrochloride salt of Compound 1.

A representative XRPD pattern of Form A is provided in FIG. 1.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 4.1, 6.6, 8.1, 9.6, 10.4, 11.1, 13.5, 14.1, 15.8, 16.2, 16.7, 20.4, 21.2, 21.6, 22.3, 24.3, 24.7, 25.6, 26.0, 27.2, 28.7, 29.3, and 30.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 6.6, 9.6, and 16.2° 2θ. In one embodiment, the XRPD pattern further comprises peaks at approximately 11.1, 20.4, and 24.3° 2θ. In one embodiment, the XRPD pattern comprises peaks at approximately 6.6, 9.6, 11.1, 16.2, 20.4, and 24.3° 2θ, in combination with at least one peak selected from approximately 4.1, 8.1, 14.1, and 15.8° 2θ.

In one embodiment, provided herein is a solid form comprising a hydrochloride salt of Compound 1, characterized by an XRPD pattern that matches the XRPD pattern presented in FIG. 1.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form A is provided in FIG. 2. In one embodiment, provided herein is a solid form comprising a hydrochloride salt of Compound 1, characterized by an FT-Raman spectrum that matches the FT-Raman spectrum presented in FIG. 2.

Representative differential scanning calorimetry (DSC) and thermal gravimetric analysis (TGA) thermograms of Form A are provided in FIG. 3.

In one embodiment, provided herein is a solid form comprising a hydrochloride salt of Compound 1, which exhibits, as characterized by DSC, a first thermal event with an onset temperature of about 55° C., and a second thermal event with an onset temperature of about 110° C. In one embodiment, the first thermal event also has a peak temperature of about 80° C., and the second thermal event also has a peak temperature of about 122° C. In one embodiment, provided herein is a solid form comprising a hydrochloride salt of Compound 1, characterized by a DSC thermogram that matches the DSC thermogram presented in FIG. 3.

In one embodiment, provided herein is a solid form comprising a hydrochloride salt of Compound 1, which exhibits a weight loss of about 4.8% upon heating from about 26° C. to about 100° C., and a weight loss of about 5.9% upon heating from about 100° C. to about 225° C. In one embodiment, without being limited by any particular theory, the weight losses correspond to the loss of water (and trace ethyl acetate) up to 100° C. followed by loss of (trace ethyl acetate and) HCl gas above 100° C. In one embodiment, provided herein is a solid form comprising a hydrochloride salt of Compound 1, characterized by a TGA thermogram that matches the TGA thermogram presented in FIG. 3.

A representative polarized light microscopy (PLM) image of Form A is presented in FIG. 4.

In one embodiment, Form A is prepared by slurrying an HCl salt of Compound 1 in a solvent. In one embodiment, Form A is prepared by slurrying an HCl salt of Compound 1 (e.g., an amorphous form of the HCl salt of Compound 1) in a solvent for a period of time (e.g., about 48 h) while cycling the temperature (e.g., between about 5° C. and about 40° C.). In one embodiment, provided herein is a method for preparing Form A, comprising 1) obtaining a slurry of an HCl salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form A of an HCl salt of Compound 1. In one embodiment, the solvent is ethyl acetate. In one embodiment, the solvent is MIBK. In one embodiment, the solvent is acetonitrile.

In one embodiment, provided herein is a solid form comprising Form A of an HCl salt of Compound 1 and one or more forms of a free base of Compound 1 (e.g., amorphous form and crystalline forms). In one embodiment, provided herein is a solid form comprising Form A of an HCl salt of Compound 1 and one or more non-Form A forms of an HCl salt of Compound 1 (e.g., Form B and Form C of an HCl salt of Compound 1).

(ii) Form B of Hydrochloride Salt of Compound 1

In certain embodiments, provided herein is Form B of a hydrochloride salt of Compound 1.

In one embodiment, Form B is crystalline. In one embodiment, Form B is substantially crystalline.

A representative XRPD pattern of Form B is provided in FIG. 5.

In one embodiment, provided herein is a solid form comprising a hydrochloride salt of Compound 1, characterized by 1, 2, 3, 4, 5, 6, 7, 8, 9, 10, 11, or all of the peaks located at approximately the following positions: 9.9, 10.2, 13.5, 14.6, 16.9, 18.4, 19.7, 24.3, 24.9, 26.0, 29.3, and 33.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 10.2, 16.9, and 26.0° 2θ. In one embodiment, the XRPD pattern further comprises peaks at approximately 9.9, 13.5, and 19.7° 2θ. In one embodiment, the XRPD pattern comprises peaks at approximately 9.9, 10.2, 13.5, 16.9, 19.7, and 26.0° 2θ, in combination with at least one peak selected from approximately 14.6, 18.4, 24.3, and 24.9° 2θ.

In one embodiment, provided herein is a solid form comprising a hydrochloride salt of Compound 1, characterized by an XRPD pattern that matches the XRPD pattern presented in FIG. 5.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

In one embodiment, Form B is prepared by slurrying an HCl salt of Compound 1 in a solvent. In one embodiment, provided herein is a method for preparing Form B, comprising 1) obtaining a slurry of an HCl salt of Compound 1 in a solvent; 2) seeding the slurry with Form A of an HCl salt of Compound 1; 3) stirring the slurry at a first temperature (e.g., about 40° C.) for a period of time (e.g., about 1 h); 4) slowly cooling (at a rate of, e.g., about 0.1° C./min) the slurry to a second temperature (e.g., room temperature) followed by stirring at the second temperature for a period of time (e.g., overnight); and 5) collecting solids by filtering an aliquot of the slurry to provide Form B of an HCl salt of Compound 1. In one embodiment, the solvent is acetonitrile.

In one embodiment, Form B of a hydrochloride salt of Compound 1 converts to Form C of a hydrochloride salt of Compound 1 under ambient conditions.

In one embodiment, provided herein is a solid form comprising Form B of an HCl salt of Compound 1 and one or more forms of a free base of Compound 1 (e.g., amorphous form and crystalline forms). In one embodiment, provided herein is a solid form comprising Form B of an HCl salt of Compound 1 and one or more non-Form B forms of an HCl salt of Compound 1 (e.g., Form A and Form C of an HCl salt of Compound 1).

(iii) Form C of Hydrochloride Salt of Compound 1

In certain embodiments, provided herein is Form C of a hydrochloride salt of Compound 1.

In one embodiment, Form C is crystalline. In one embodiment, Form C is substantially crystalline.

In one embodiment, the molar ratio of Compound 1 to hydrochloric acid in Form C is about 1:1. In one embodiment, Form C is a mono-hydrochloride salt of Compound 1.

In one embodiment, Form C is a hydrate of a hydrochloride salt of Compound 1. In one embodiment, Form C is a solvate of a hydrochloride salt of Compound 1. In one embodiment, Form C is an acetonitrile solvate of a hydrochloride salt of Compound 1.

A representative XRPD pattern of Form C is provided in FIG. 6.

In one embodiment, provided herein is a solid form comprising a hydrochloride salt of Compound 1, characterized by 1, 2, 3, 4, 5, 6, 7, 8, 9, 10, or all of the peaks located at approximately the following positions: 9.8, 10.4, 11.5, 13.6, 16.5, 17.1, 18.2, 19.9, 20.9, 24.6, and 26.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by all of the peaks.

In one embodiment, provided herein is a solid form comprising a hydrochloride salt of Compound 1, characterized by an XRPD pattern comprising peaks at approximately 10.4, 13.6, and 20.9° 2θ. In one embodiment, the XRPD pattern further comprises peaks at approximately 9.8, 19.9, and 24.6° 2θ. In one embodiment, the XRPD pattern comprises peaks at approximately 9.8, 10.4, 13.6, 19.9, 20.9, and 24.6° 2θ, in combination with at least one peak selected from approximately 11.5, 16.5, 18.2, and 26.6° 2θ.

In one embodiment, provided herein is a solid form comprising a hydrochloride salt of Compound 1, characterized by an XRPD pattern that matches the XRPD pattern presented in FIG. 6.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form C is provided in FIG. 7. In one embodiment, provided herein is a solid form comprising a hydrochloride salt of Compound 1, characterized by an FT-Raman spectrum that matches the FT-Raman spectrum presented in FIG. 7.

Representative differential scanning calorimetry (DSC) and thermal gravimetric analysis (TGA) thermograms of Form C are provided in FIG. 8.

In one embodiment, provided herein is a solid form comprising a hydrochloride salt of Compound 1, which exhibits, as characterized by DSC, a first thermal event with an onset temperature of about 98° C., and a second thermal event with an onset temperature of about 135° C. In one embodiment, the first thermal event also has a peak temperature of about 119° C., and the second thermal event also has a peak temperature of about 143° C. In one embodiment, provided herein is a solid form comprising a hydrochloride salt of Compound 1, characterized by a DSC thermogram that matches the DSC thermogram presented in FIG. 8.

In one embodiment, provided herein is a solid form comprising a hydrochloride salt of Compound 1, which exhibits a weight loss of about 3.2% upon heating from about 20° C. to about 100° C., and a weight loss of about 7.9% upon heating from about 100° C. to about 200° C. In one embodiment, without being limited by any particular theory, the weight losses correspond to the loss of water (and trace acetonitrile) up to 100° C. followed by loss of acetonitrile then HCl gas above 100° C. In one embodiment, provided herein is a solid form comprising a hydrochloride salt of Compound 1, characterized by a TGA thermogram that matches the TGA thermogram presented in FIG. 8.

A representative polarized light microscopy (PLM) image of Form C is presented in FIG. 9.

In one embodiment, Form C is prepared by slurrying an HCl salt of Compound 1 in a solvent. In one embodiment, provided herein is a method for preparing Form C, comprising 1) obtaining a slurry of an HCl salt of Compound 1 in a solvent; 2) seeding the slurry with Form A of an HCl salt of Compound 1; 3) stirring the slurry at a first temperature (e.g., about 40° C.) for a period of time (e.g., about 1 h); 4) slowly cooling (at a rate of, e.g., about 0.1° C./min) the slurry to a second temperature (e.g., room temperature) followed by stirring at the second temperature for a period of time (e.g., overnight); and 5) collecting solids from the slurry by filtration (e.g., under vacuum) and drying (e.g., air-drying) the collected solids to provide Form C of an HCl salt of Compound 1. In one embodiment, the solvent is acetonitrile.

In one embodiment, provided herein is a solid form comprising Form C of an HCl salt of Compound 1 and one or more forms of a free base of Compound 1 (e.g., amorphous form and crystalline forms). In one embodiment, provided herein is a solid form comprising Form C of an HCl salt of Compound 1 and one or more non-Form C forms of an HCl salt of Compound 1 (e.g., Form A and Form B of an HCl salt of Compound 1). In one embodiment, provided herein is a solid form comprising Form C of an HCl salt of Compound 1 and one or more non-HCl salt forms of Compound 1.

(c) Hydrobromide Salt of Compound 1

In some embodiments, provided herein is a hydrobromide salt of Compound 1. It is contemplated that a hydrobromide salt of Compound 1 can exist in a variety of solid forms. Such solid forms include crystalline solids, such as polymorphs, solvates and hydrates of crystalline hydrobromide salt of Compound 1, as well as amorphous solids, or mixtures thereof.

In one embodiment, provided herein is a solid form comprising a hydrobromide salt of Compound 1. In one embodiment, the solid form is a solvate of a hydrobromide salt of Compound 1. In one embodiment, the solid form is a hydrate of a hydrobromide salt of Compound 1. In one embodiment, the solid form is a non-solvated form of a hydrobromide salt of Compound 1. In one embodiment, the solid form is an anhydrate of a hydrobromide salt of Compound 1.

In some embodiments, the molar ratio of Compound 1 to hydrobromic acid in the solid form ranges from about 1:1 to about 1:2. In one embodiment, the molar ratio is about 1:2 (i.e., bis-hydrobromide salt). In another embodiment, the molar ratio is about 1:1 (i.e., mono-hydrobromide salt).

(i) Form A of Hydrobromide Salt of Compound 1

In certain embodiments, provided herein is Form A of a hydrobromide salt of Compound 1.

In one embodiment, Form A is crystalline. In one embodiment, Form A is substantially crystalline.

In one embodiment, Form A is a hydrate of a hydrobromide salt of Compound 1.

A representative XRPD pattern of Form A is provided in FIG. 10.

In one embodiment, provided herein is a solid form comprising a hydrobromide salt of Compound 1, characterized by 1, 2, 3, 4, 5, 6, 7, 8, 9, 10, 11, or all of the peaks located at approximately the following positions: 6.6, 9.5, 11.2, 13.4, 14.0, 16.1, 20.3, 21.4, 21.7, 25.4, 26.9, and 29.3° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 6.6, 16.1, and 20.3° 2θ. In one embodiment, the XRPD pattern further comprises peaks at approximately 9.5, 11.2, and 25.4° 2θ. In one embodiment, the XRPD pattern comprises peaks at approximately 6.6, 9.5, 11.2, 16.1, 20.3, and 25.4° 2θ, in combination with at least one peak selected from approximately 13.4, 14.0, 21.4, and 21.7° 2θ.

In one embodiment, provided herein is a solid form comprising a hydrobromide salt of Compound 1, characterized by an XRPD pattern that matches the XRPD pattern presented in FIG. 10.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form A is provided in FIG. 11. In one embodiment, provided herein is a solid form comprising a hydrobromide salt of Compound 1, characterized by an FT-Raman spectrum that matches the FT-Raman spectrum presented in FIG. 11.

Representative differential scanning calorimetry (DSC) and thermal gravimetric analysis (TGA) thermograms of Form A are provided in FIG. 12.

In one embodiment, provided herein is a solid form comprising a hydrobromide salt of Compound 1, which exhibits, as characterized by DSC, a first thermal event with an onset temperature of about 53° C., and a second thermal event with an onset temperature of about 128° C. In one embodiment, the first thermal event also has a peak temperature of about 91° C., and the second thermal event also has a peak temperature of about 138° C. In one embodiment, provided herein is a solid form comprising a hydrobromide salt of Compound 1, characterized by a DSC thermogram that matches the DSC thermogram presented in FIG. 12.

In one embodiment, provided herein is a solid form comprising a hydrobromide salt of Compound 1, which exhibits a weight loss of about 3.2% upon heating from about 26° C. to about 116° C., and a weight loss of about 4.5% upon heating from about 116° C. to about 198° C. In one embodiment, without being limited by any particular theory, the weight losses correspond to the loss of water up to 116° C. followed by loss of HBr gas above 116° C. In one embodiment, provided herein is a solid form comprising a hydrobromide salt of Compound 1, characterized by a TGA thermogram that matches the TGA thermogram presented in FIG. 12.

In one embodiment, Form A is prepared by slurrying an HBr salt of Compound 1 in a solvent. In one embodiment, Form A is prepared by slurrying an HBr salt of Compound 1 (e.g., an amorphous form of the HBr salt of Compound 1) in a solvent for a period of time (e.g., about 48 h) while cycling the temperature (e.g., between about 5° C. and about 40° C.). In one embodiment, provided herein is a method for preparing Form A, comprising 1) obtaining a slurry of an HBr salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form A of an HBr salt of Compound 1. In one embodiment, the solvent is MIBK. In one embodiment, the solvent is 2-propanol.

In one embodiment, provided herein is a solid form comprising Form A of an HBr salt of Compound 1 and one or more forms of a free base of Compound 1 (e.g., amorphous form and crystalline forms). In one embodiment, provided herein is a solid form comprising Form A of an HBr salt of Compound 1 and one or more non-Form A forms of an HBr salt of Compound 1 (e.g., Form B of an HBr salt of Compound 1).

(ii) Form B of Hydrobromide Salt of Compound 1

In certain embodiments, provided herein is Form B of a hydrobromide salt of Compound 1.

In one embodiment, Form B is crystalline. In one embodiment, Form B is substantially crystalline.

In one embodiment, the molar ratio of Compound 1 to hydrobromic acid in Form B is about 1:1. In one embodiment, Form B is a mono-hydrobromide salt of Compound 1.

In one embodiment, Form B is a hydrate of a hydrobromide salt of Compound 1.

A representative XRPD pattern of Form B is provided in FIG. 13.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 6.3, 8.1, 9.0, 10.6, 11.2, 12.2, 12.5, 14.0, 14.9, 17.3, 19.2, 20.2, 20.4, 20.6, 21.6, 23.5, 23.8, 24.2, 24.5, 25.2, 25.5, 26.4, 26.8, 28.8, and 30.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 8.1, 14.9, and 25.2° 2θ. In one embodiment, the XRPD pattern further comprises peaks at approximately 11.2, 21.6, and 23.8° 2θ. In one embodiment, the XRPD pattern comprises peaks at approximately 8.1, 11.2, 14.9, 21.6, 23.8, and 25.2° 2θ, in combination with at least one peak selected from approximately 12.5, 14.0, 24.2, and 25.5° 2θ.

In one embodiment, provided herein is a solid form comprising a hydrobromide salt of Compound 1, characterized by an XRPD pattern that matches the XRPD pattern presented in FIG. 13.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form B is provided in FIG. 14. In one embodiment, provided herein is a solid form comprising a hydrobromide salt of Compound 1, characterized by an FT-Raman spectrum that matches the FT-Raman spectrum presented in FIG. 14.

Representative differential scanning calorimetry (DSC) and thermal gravimetric analysis (TGA) thermograms of Form B are provided in FIG. 15.

In one embodiment, provided herein is a solid form comprising a hydrobromide salt of Compound 1, which exhibits, as characterized by DSC, a first thermal event with an onset temperature of about 41° C., and a second thermal event with an onset temperature of about 133° C. In one embodiment, the first thermal event also has a peak temperature of about 72° C., and the second thermal event also has a peak temperature of about 144° C. In one embodiment, provided herein is a solid form comprising a hydrobromide salt of Compound 1, characterized by a DSC thermogram that matches the DSC thermogram presented in FIG. 15.

In one embodiment, provided herein is a solid form comprising a hydrobromide salt of Compound 1, which exhibits a weight loss of about 6.6% upon heating from about 25° C. to about 150° C. In one embodiment, without being limited by any particular theory, the weight losses correspond to the loss of water and then HBr gas up to 150° C. In one embodiment, provided herein is a solid form comprising a hydrobromide salt of Compound 1, characterized by a TGA thermogram that matches the TGA thermogram presented in FIG. 15.

A representative polarized light microscopy (PLM) image of Form B is presented in FIG. 16.

In one embodiment, Form B is prepared by slurrying an HBr salt of Compound 1 in a solvent. In one embodiment, provided herein is a method for preparing Form B, comprising 1) obtaining a slurry of an HBr salt of Compound 1 in a solvent; 2) concentrating the slurry in vacuo to dryness; 3) adding the same solvent to the dried sample; 4) seeding the mixture with Form A of an HBr salt of Compound 1; 5) heating the mixture (e.g., about 40° C.) for a period of time (e.g., about 1 h); 5) slowly cooling (at a rate of, e.g., about 0.1° C./min) the mixture to ambient temperature; 6) stirring the mixture at ambient temperature for a period of time (e.g., overnight); and 7) collecting solids from the slurry by filtration (e.g., under vacuum) and drying (e.g., air-drying) the collected solids (e.g., for about 20 minutes) to provide Form B of an HBr salt of Compound 1. In one embodiment, the solvent is MIBK.

In one embodiment, provided herein is a solid form comprising Form B of an HBr salt of Compound 1 and one or more forms of a free base of Compound 1 (e.g., amorphous form and crystalline forms). In one embodiment, provided herein is a solid form comprising Form B of an HBr salt of Compound 1 and one or more non-Form B forms of an HBr salt of Compound 1 (e.g., Form A of an HBr salt of Compound 1).

(d) Napadisylate Salt of Compound 1

In some embodiments, provided herein is a napadisylate salt (i.e., a naphthalene-1,5-disulfonic acid salt) of Compound 1. It is contemplated that a napadisylate salt of Compound 1 can exist in a variety of solid forms. Such solid forms include crystalline solids, such as polymorphs, solvates and hydrates of crystalline napadisylate salt of Compound 1, as well as amorphous solids, or mixtures thereof.

In one embodiment, provided herein is a solid form comprising a napadisylate salt of Compound 1. In one embodiment, the solid form is a solvate of a napadisylate salt of Compound 1. In one embodiment, the solid form is a hydrate of a napadisylate salt of Compound 1. In one embodiment, the solid form is a non-solvated form of a napadisylate salt of Compound 1. In one embodiment, the solid form is an anhydrate of a napadisylate salt of Compound 1.

In some embodiments, the molar ratio of Compound 1 to naphthalene-1,5-disulfonic acid in the solid form ranges from about 2:1 to about 1:2. In one embodiment, the molar ratio is about 1:2 (i.e., bis-napadisylate salt). In another embodiment, the molar ratio is about 1:1 (i.e., mono-napadisylate salt). In yet another embodiment, the molar ratio is about 2:1 (i.e., hemi-napadisylate salt).

(i) Form A of Napadisylate Salt of Compound 1

In certain embodiments, provided herein is Form A of a napadisylate salt of Compound 1.

In one embodiment, Form A is crystalline. In one embodiment, Form A is substantially crystalline.

In one embodiment, the molar ratio of Compound 1 to naphthalene-1,5-disulfonic acid in Form A is about 2:1. In one embodiment, Form A is a hemi-napadisylate salt of Compound 1.

In one embodiment, Form A is an anhydrate of a napadisylate salt of Compound 1.

A representative XRPD pattern of Form A is provided in FIG. 17.

In one embodiment, provided herein is a solid form comprising a napadisylate salt of Compound 1, characterized by 1, 2, 3, 4, 5, 6, 7, 8, 9, 10, 11, 12, 13, 14, 15, 16, 17, 18, 19, or all of the peaks located at approximately the following positions: 7.9, 9.0, 10.4, 11.8, 13.5, 15.8, 16.7, 18.1, 18.5, 19.5, 21.5, 21.9, 23.5, 24.0, 25.5, 25.9, 26.6, 27.0, 29.1, and 33.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a napadisylate salt of Compound 1, characterized by an XRPD pattern comprising peaks at approximately 7.9, 15.8, and 18.5° 2θ. In one embodiment, the XRPD pattern further comprises peaks at approximately 13.5, 24.0, and 25.9° 2θ. In one embodiment, the XRPD pattern comprises peaks at approximately 7.9, 13.5, 15.8, 18.5, 24.0, and 25.9° 2θ, in combination with at least one peak selected from approximately 10.4, 18.1, 21.5, and 25.5° 2θ.

In one embodiment, provided herein is a solid form comprising a napadisylate salt of Compound 1, characterized by an XRPD pattern that matches the XRPD pattern presented in FIG. 17.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form A is provided in FIG. 18. In one embodiment, provided herein is a solid form comprising a napadisylate salt of Compound 1, characterized by an FT-Raman spectrum that matches the FT-Raman spectrum presented in FIG. 18.

Representative differential scanning calorimetry (DSC) and thermal gravimetric analysis (TGA) thermograms of Form A are provided in FIG. 19.

In one embodiment, provided herein is a solid form comprising a napadisylate salt of Compound 1, which exhibits, as characterized by DSC, a thermal event with an onset temperature of about 235° C. In one embodiment, the thermal event also has a peak temperature of about 239° C. In one embodiment, provided herein is a solid form comprising a napadisylate salt of Compound 1, characterized by a DSC thermogram that matches the DSC thermogram presented in FIG. 19.

In one embodiment, provided herein is a solid form comprising a napadisylate salt of Compound 1, which exhibits a weight loss of about 0.06% upon heating from about 25° C. to about 225° C. In one embodiment, provided herein is a solid form comprising a napadisylate salt of Compound 1, characterized by a TGA thermogram that matches the TGA thermogram presented in FIG. 19.

A representative polarized light microscopy (PLM) image of Form A is presented in FIG. 20.

A representative dynamic vapor sorption (DVS) isotherm of Form A is presented in FIG. 21. In one embodiment, Form A exhibits a weight increase of about 1.6% at 85% relative humidity at 25° C. In one embodiment, provided herein is a solid form comprising a napadisylate salt of Compound 1, characterized by a DVS isotherm that matches the DVS isotherm presented in FIG. 21. In one embodiment, Form A is slightly hygroscopic.

In one embodiment, Form A is prepared by slurrying a napadisylate salt of Compound 1 in a solvent. In one embodiment, Form A is prepared by slurrying a napadisylate salt of Compound 1 (e.g., an amorphous form of the napadisylate salt of Compound 1) in a solvent for a period of time (e.g., about 48 h) while cycling the temperature (e.g., between about 5° C. and about 40° C.). In one embodiment, provided herein is a method for preparing Form A, comprising 1) obtaining a slurry of a napadisylate salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form A of a napadisylate salt of Compound 1. In one embodiment, the solvent is 2-propanol.

In one embodiment, provided herein is a solid form comprising Form A of a napadisylate salt of Compound 1 and one or more forms of a free base of Compound 1 (e.g., amorphous form and crystalline forms). In one embodiment, provided herein is a solid form comprising Form A of a napadisylate salt of Compound 1 and one or more non-Form A forms of a napadisylate salt of Compound 1 (e.g., Form B and Form C of a napadisylate salt of Compound 1).

(ii) Form B of Napadisylate Salt of Compound 1

In certain embodiments, provided herein is Form B of a napadisylate salt of Compound 1.

In one embodiment, Form B is crystalline. In one embodiment, Form B is substantially crystalline.

In one embodiment, the molar ratio of Compound 1 to naphthalene-1,5-disulfonic acid in Form B is about 1:1. In one embodiment, Form B is a mono-napadisylate salt of Compound 1.

In one embodiment, Form B is a hydrate of a napadisylate salt of Compound 1.

A representative XRPD pattern of Form B is provided in FIG. 22.

In one embodiment, provided herein is a solid form comprising a napadisylate salt of Compound 1, characterized by 1, 2, 3, 4, 5, 6, 7, 8, 9, 10, 11, 12, 13, 14, 15, 16, 17, 18, or all of the peaks located at approximately the following positions: 4.7, 7.4, 8.9, 12.5, 13.8, 14.0, 14.9, 15.4, 16.6, 17.2, 18.8, 19.1, 20.5, 20.9, 21.9, 24.6, 25.2, 25.8, and 26.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a napadisylate salt of Compound 1, characterized by an XRPD pattern comprising peaks at approximately 4.7, 7.4, and 14.0° 2θ. In one embodiment, the XRPD pattern further comprises peaks at approximately 19.1, 20.9, and 26.8° 2θ. In one embodiment, the XRPD pattern comprises peaks at approximately 4.7, 7.4, 14.0, 19.1, 20.9, and 26.8° 2θ, in combination with at least one peak selected from approximately 13.8, 14.9, 15.4, and 18.8° 2θ.

In one embodiment, provided herein is a solid form comprising a napadisylate salt of Compound 1, characterized by an XRPD pattern that matches the XRPD pattern presented in FIG. 22.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form B is provided in FIG. 23. In one embodiment, provided herein is a solid form comprising a napadisylate salt of Compound 1, characterized by an FT-Raman spectrum that matches the FT-Raman spectrum presented in FIG. 23.

Representative differential scanning calorimetry (DSC) and thermal gravimetric analysis (TGA) thermograms of Form B are provided in FIG. 24.

In one embodiment, provided herein is a solid form comprising a napadisylate salt of Compound 1, which exhibits, as characterized by DSC, a first thermal event with an onset temperature of about 43° C., and a second thermal event with an onset temperature of about 150° C. In one embodiment, the first thermal event also has a peak temperature of about 104° C., and the second thermal event also has a peak temperature of about 157° C. In one embodiment, provided herein is a solid form comprising a napadisylate salt of Compound 1, characterized by a DSC thermogram that matches the DSC thermogram presented in FIG. 24.

In one embodiment, provided herein is a solid form comprising a napadisylate salt of Compound 1, which exhibits a weight loss of about 7.0% upon heating from about 25° C. to about 150° C. In one embodiment, without being limited by any particular theory, the weight losses correspond to the loss of water up to 150° C. In one embodiment, provided herein is a solid form comprising a napadisylate salt of Compound 1, characterized by a TGA thermogram that matches the TGA thermogram presented in FIG. 24.

A representative polarized light microscopy (PLM) image of Form B is presented in FIG. 25.

In one embodiment, Form B is prepared by slurrying a napadisylate salt of Compound 1 in a solvent. In one embodiment, Form B is prepared by slurrying a napadisylate salt of Compound 1 (e.g., an amorphous form of the napadisylate salt of Compound 1) in a solvent for a period of time (e.g., about 48 h) while cycling the temperature (e.g., between about 5° C. and about 40° C.). In one embodiment, provided herein is a method for preparing Form B, comprising 1) obtaining a slurry of a napadisylate salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form B of a napadisylate salt of Compound 1. In one embodiment, the solvent is 1-butanol. In one embodiment, the solvent is MIBK. In one embodiment, the solvent is acetone. In one embodiment, the solvent is acetonitrile.

In one embodiment, provided herein is a solid form comprising Form B of a napadisylate salt of Compound 1 and one or more forms of a free base of Compound 1 (e.g., amorphous form and crystalline forms). In one embodiment, provided herein is a solid form comprising Form B of a napadisylate salt of Compound 1 and one or more non-Form B forms of a napadisylate salt of Compound 1 (e.g., Form A and Form C of a napadisylate salt of Compound 1).

(iii) Form C of Napadisylate Salt of Compound 1

In certain embodiments, provided herein is Form C of a napadisylate salt of Compound 1.

In one embodiment, Form C is crystalline. In one embodiment, Form C is substantially crystalline.

In one embodiment, the molar ratio of Compound 1 to naphthalene-1,5-disulfonic acid in Form C is about 1:1. In one embodiment, Form C is a mono-napadisylate salt of Compound 1.

In one embodiment, Form C is a hydrate of a napadisylate salt of Compound 1.

A representative XRPD pattern of Form C is provided in FIG. 26.

In one embodiment, provided herein is a solid form comprising a napadisylate salt of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 5.1, 7.2, 8.1, 10.3, 10.9, 12.5, 13.0, 14.0, 14.5, 14.9, 16.6, 18.5, 18.8, 19.5, 20.5, 22.1, 23.2, 24.5, 24.9, 25.6, 26.1, 26.5, and 27.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a napadisylate salt of Compound 1, characterized by an XRPD pattern comprising peaks at approximately 5.1, 14.0, and 14.9° 2θ. In one embodiment, the XRPD pattern further comprises peaks at approximately 10.9, 14.5, and 22.1° 2θ. In one embodiment, the XRPD pattern comprises peaks at approximately 5.1, 10.9, 14.0, 14.5, 14.9, and 22.1° 2θ, in combination with at least one peak selected from approximately 12.5, 13.0, 16.6, and 19.5° 2θ.

In one embodiment, provided herein is a solid form comprising a napadisylate salt of Compound 1, characterized by an XRPD pattern that matches the XRPD pattern presented in FIG. 26.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form C is provided in FIG. 27. In one embodiment, provided herein is a solid form comprising a napadisylate salt of Compound 1, characterized by an FT-Raman spectrum that matches the FT-Raman spectrum presented in FIG. 27.

Representative differential scanning calorimetry (DSC) and thermal gravimetric analysis (TGA) thermograms of Form C are provided in FIG. 28.

In one embodiment, provided herein is a solid form comprising a napadisylate salt of Compound 1, which exhibits, as characterized by DSC, a (broad) thermal event with an onset temperature of about 117° C. In one embodiment, the thermal event also has a peak temperature of about 134° C. In one embodiment, provided herein is a solid form comprising a napadisylate salt of Compound 1, characterized by a DSC thermogram that matches the DSC thermogram presented in FIG. 28.

In one embodiment, provided herein is a solid form comprising a napadisylate salt of Compound 1, which exhibits a weight loss of about 9.1% upon heating from about 25° C. to about 150° C. In one embodiment, without being limited by any particular theory, the weight losses correspond to the loss of water up to 150° C. In one embodiment, provided herein is a solid form comprising a napadisylate salt of Compound 1, characterized by a TGA thermogram that matches the TGA thermogram presented in FIG. 28.

A representative polarized light microscopy (PLM) image of Form C is presented in FIG. 29.

In one embodiment, Form C is prepared by slurrying a napadisylate salt of Compound 1 in a solvent. In one embodiment, Form C is prepared by slurrying a napadisylate salt of Compound 1 (e.g., an amorphous form of the napadisylate salt of Compound 1) in a solvent for a period of time (e.g., about 48 h) while cycling the temperature (e.g., between about 5° C. and about 40° C.). In one embodiment, provided herein is a method for preparing Form C, comprising 1) obtaining a slurry of a napadisylate salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form C of a napadisylate salt of Compound 1. In one embodiment, the solvent is toluene. In one embodiment, the solvent is MTBE.

In one embodiment, provided herein is a solid form comprising Form C of a napadisylate salt of Compound 1 and one or more forms of a free base of Compound 1 (e.g., amorphous form and crystalline forms). In one embodiment, provided herein is a solid form comprising Form C of a napadisylate salt of Compound 1 and one or more non-Form C forms of a napadisylate salt of Compound 1 (e.g., Form A and Form B of a napadisylate salt of Compound 1).

(e) 2-Naphthalenesulfonate Salt of Compound 1

In some embodiments, provided herein is a 2-naphthalenesulfonate salt of Compound 1. It is contemplated that a 2-naphthalenesulfonate salt of Compound 1 can exist in a variety of solid forms. Such solid forms include crystalline solids, such as polymorphs, solvates and hydrates of crystalline 2-naphthalenesulfonate salt of Compound 1, as well as amorphous solids, or mixtures thereof.

In one embodiment, provided herein is a solid form comprising a 2-naphthalenesulfonate salt of Compound 1. In one embodiment, the solid form is a solvate of a 2-naphthalenesulfonate salt of Compound 1. In one embodiment, the solid form is a hydrate of a 2-naphthalenesulfonate salt of Compound 1. In one embodiment, the solid form is a non-solvated form of a 2-naphthalenesulfonate salt of Compound 1. In one embodiment, the solid form is an anhydrate of a 2-naphthalenesulfonate salt of Compound 1.

In some embodiments, the molar ratio of Compound 1 to 2-naphthalenesulfonic acid in the solid form ranges from about 1:1 to about 1:2. In one embodiment, the molar ratio is about 1:2 (i.e., bis-2-naphthalenesulfonate salt). In another embodiment, the molar ratio is about 1:1 (i.e., mono-2-naphthalenesulfonate salt).

(i) Form A of 2-Naphthalenesulfonate Salt of Compound 1

In certain embodiments, provided herein is Form A of a 2-naphthalenesulfonate salt of Compound 1.

In one embodiment, Form A is crystalline. In one embodiment, Form A is substantially crystalline.

In one embodiment, the molar ratio of Compound 1 to 2-naphthalenesulfonic acid in Form A is about 1:1. In one embodiment, Form A is a mono-2-naphthalenesulfonate salt of Compound 1.

In one embodiment, Form A is an anhydrate of a 2-naphthalenesulfonate salt of Compound 1. In one embodiment, Form A is a solvate of a 2-naphthalenesulfonate salt of Compound 1. In one embodiment, Form A is a 2-propanol solvate of a 2-naphthalenesulfonate salt of Compound 1.

A representative XRPD pattern of Form A is provided in FIG. 30.

In one embodiment, provided herein is a solid form comprising a 2-naphthalenesulfonate salt of Compound 1, characterized by 1, 2, 3, 4, 5, 6, 7, 8, 9, 10, 11, 12, 13, 14, 15, 16, 17, 18, 19, 20, 21, 22, 23, or all of the peaks located at approximately the following positions: 6.3, 9.5, 10.2, 10.7, 11.6, 12.7, 13.3, 13.6, 14.8, 15.6, 16.8, 17.4, 18.5, 19.1, 20.1, 20.4, 22.3, 22.7, 23.3, 24.7, 25.2, 26.0, 28.7, and 29.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a 2-naphthalenesulfonate salt of Compound 1, characterized by an XRPD pattern comprising peaks at approximately 6.3, 19.1, and 20.1° 2θ. In one embodiment, the XRPD pattern further comprises peaks at approximately 12.7, 13.6, and 20.4° 2θ. In one embodiment, the XRPD pattern comprises peaks at approximately 6.3, 12.7, 13.6, 19.1, 20.1, and 20.4° 2θ, in combination with at least one peak selected from approximately 9.5, 10.7, 22.7, and 24.7° 2θ.

In one embodiment, provided herein is a solid form comprising a 2-naphthalenesulfonate salt of Compound 1, characterized by an XRPD pattern that matches the XRPD pattern presented in FIG. 30.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form A is provided in FIG. 31. In one embodiment, provided herein is a solid form comprising a 2-naphthalenesulfonate salt of Compound 1, characterized by an FT-Raman spectrum that matches the FT-Raman spectrum presented in FIG. 31.

Representative differential scanning calorimetry (DSC) and thermal gravimetric analysis (TGA) thermograms of Form A are provided in FIG. 32.

In one embodiment, provided herein is a solid form comprising a 2-naphthalenesulfonate salt of Compound 1, which exhibits, as characterized by DSC, a thermal event with an onset temperature of about 186° C. In one embodiment, the thermal event also has a peak temperature of about 189° C. In one embodiment, provided herein is a solid form comprising a 2-naphthalenesulfonate salt of Compound 1, characterized by a DSC thermogram that matches the DSC thermogram presented in FIG. 32.

In one embodiment, provided herein is a solid form comprising a 2-naphthalenesulfonate salt of Compound 1, which exhibits a weight loss of about 1.2% upon heating from about 125° C. to about 199° C. In one embodiment, without being limited by any particular theory, the weight loss from about 125° C. to about 199° C. corresponds to the loss of 2-propanol. In one embodiment, provided herein is a solid form comprising a 2-naphthalenesulfonate salt of Compound 1, characterized by a TGA thermogram that matches the TGA thermogram presented in FIG. 32.

A representative polarized light microscopy (PLM) image of Form A is presented in FIG. 33.

In one embodiment, Form A is prepared by slurrying a 2-naphthalenesulfonate salt of Compound 1 in a solvent. In one embodiment, Form A is prepared by slurrying a 2-naphthalenesulfonate salt of Compound 1 (e.g., an amorphous form of the 2-naphthalenesulfonate salt of Compound 1) in a solvent for a period of time (e.g., about 48 h) while cycling the temperature (e.g., between about 5° C. and about 40° C.). In one embodiment, provided herein is a method for preparing Form A, comprising 1) obtaining a slurry of a 2-naphthalenesulfonate salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form A of a 2-naphthalenesulfonate salt of Compound 1. In one embodiment, the solvent is 2-propanol.

In one embodiment, provided herein is a solid form comprising Form A of a 2-naphthalenesulfonate salt of Compound 1 and one or more forms of a free base of Compound 1 (e.g., amorphous form and crystalline forms). In one embodiment, provided herein is a solid form comprising Form A of a 2-naphthalenesulfonate salt of Compound 1 and one or more non-Form A forms of a 2-naphthalenesulfonate salt of Compound 1 (e.g., Form B and Form C of a 2-naphthalenesulfonate salt of Compound 1).

(f) Edisylate Salt of Compound 1

In some embodiments, provided herein is an edisylate salt (i.e., an ethane-1,2-disulfonic acid salt) of Compound 1. It is contemplated that an edisylate salt of Compound 1 can exist in a variety of solid forms. Such solid forms include crystalline solids, such as polymorphs, solvates and hydrates of crystalline edisylate salt of Compound 1, as well as amorphous solids, or mixtures thereof.

In one embodiment, provided herein is a solid form comprising an edisylate salt of Compound 1. In one embodiment, the solid form is a solvate of an edisylate salt of Compound 1. In one embodiment, the solid form is a hydrate of an edisylate salt of Compound 1. In one embodiment, the solid form is a non-solvated form of an edisylate salt of Compound 1. In one embodiment, the solid form is an anhydrate of an edisylate salt of Compound 1.

In some embodiments, the molar ratio of Compound 1 to ethane-1,2-disulfonic acid in the solid form ranges from about 2:1 to about 1:2. In one embodiment, the molar ratio is about 1:2 (i.e., bis-edisylate salt). In another embodiment, the molar ratio is about 1:1 (i.e., mono-edisylate salt). In yet another embodiment, the molar ratio is about 2:1 (i.e., hemi-edisylate salt). In one embodiment, the molar ratio is about 4:3.

(i) Form A of Edisylate Salt of Compound 1

In certain embodiments, provided herein is Form A of an edisylate salt of Compound 1.

In one embodiment, Form A is crystalline. In one embodiment, Form A is substantially crystalline.

In one embodiment, the molar ratio of Compound 1 to ethane-1,2-disulfonic acid in Form A is about 1:1. In one embodiment, Form A is a mono-edisylate salt of Compound 1.

In one embodiment, Form A is a hydrate of an edisylate salt of Compound 1.

A representative XRPD pattern of Form A is provided in FIG. 34.

In one embodiment, provided herein is a solid form comprising an edisylate salt of Compound 1, characterized by 1, 2, 3, 4, 5, 6, 7, 8, 9, 10, 11, 12, 13, 14, 15, 16, or all of the peaks located at approximately the following positions: 4.3, 8.8, 11.4, 11.9, 14.4, 14.9, 15.9, 17.7, 18.3, 20.5, 20.8, 21.3, 22.0, 23.9, 25.8, 27.3, and 28.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising an edisylate salt of Compound 1, characterized by an XRPD pattern comprising peaks at approximately 4.3, 8.8, and 11.9° 2θ. In one embodiment, the XRPD pattern further comprises peaks at approximately 15.9, 21.3, and 23.9° 2θ. In one embodiment, the XRPD pattern comprises peaks at approximately 4.3, 8.8, 11.9, 15.9, 21.3, and 23.9° 2θ, in combination with at least one peak selected from approximately 14.4, 14.9, 17.7, and 22.0° 2θ.

In one embodiment, provided herein is a solid form comprising an edisylate salt of Compound 1, characterized by an XRPD pattern that matches the XRPD pattern presented in FIG. 34.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form A is provided in FIG. 35. In one embodiment, provided herein is a solid form comprising an edisylate salt of Compound 1, characterized by an FT-Raman spectrum that matches the FT-Raman spectrum presented in FIG. 35.

Representative differential scanning calorimetry (DSC) and thermal gravimetric analysis (TGA) thermograms of Form A are provided in FIG. 36.

In one embodiment, provided herein is a solid form comprising an edisylate salt of Compound 1, which exhibits, as characterized by DSC, a first thermal event with an onset temperature of about 69° C., and a second thermal event with an onset temperature of about 207° C. In one embodiment, the first thermal event also has two peak temperatures of about 83° C. and about 107° C., respectively, and the second thermal event also has a peak temperature of about 213° C. In one embodiment, provided herein is a solid form comprising an edisylate salt of Compound 1, characterized by a DSC thermogram that matches the DSC thermogram presented in FIG. 36.

In one embodiment, provided herein is a solid form comprising an edisylate salt of Compound 1, which exhibits a weight loss of about 6.2% upon heating from about 26° C. to about 125° C. In one embodiment, without being limited by any particular theory, the weight losses correspond to the loss of water up to 125° C. In one embodiment, provided herein is a solid form comprising an edisylate salt of Compound 1, characterized by a TGA thermogram that matches the TGA thermogram presented in FIG. 36.

A representative polarized light microscopy (PLM) image of Form A is presented in FIG. 37.

In one embodiment, Form A is prepared by slurrying an edisylate salt of Compound 1 in a solvent. In one embodiment, Form A is prepared by slurrying an edisylate salt of Compound 1 (e.g., an amorphous form of the Edisylate salt of Compound 1) in a solvent for a period of time (e.g., about 48 h) while cycling the temperature (e.g., between about 5° C. and about 40° C.). In one embodiment, provided herein is a method for preparing Form A, comprising 1) obtaining a slurry of an edisylate salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form A of an edisylate salt of Compound 1. In one embodiment, the solvent is toluene. In one embodiment, the solvent is MTBE. In one embodiment, the solvent is 1-butanol. In one embodiment, the solvent is MIBK. In one embodiment, the solvent is ethyl acetate. In one embodiment, the solvent is acetone. In one embodiment, the solvent is acetonitrile.

In one embodiment, provided herein is a method for preparing Form A, comprising 1) obtaining a slurry of an edisylate salt of Compound 1 in a solvent; 2) seeding the slurry with Form A of an edisylate salt of Compound 1; 3) stirring the slurry at a first temperature (e.g., about 25° C.); 4) cooling the slurry to a second temperature (e.g., about 5° C.) followed by stirring at the second temperature for a period of time (e.g., overnight); and 5) collecting solids from the slurry by filtration (e.g., under vacuum) and drying (e.g., air-drying) the collected solids (e.g., for about 20 minutes) to provide Form A of an edisylate salt of Compound 1. In one embodiment, the solvent is acetone.

In one embodiment, provided herein is a solid form comprising Form A of an edisylate salt of Compound 1 and one or more forms of a free base of Compound 1 (e.g., amorphous form and crystalline forms). In one embodiment, provided herein is a solid form comprising Form A of an edisylate salt of Compound 1 and one or more non-Form A forms of an edisylate salt of Compound 1 (e.g., Form B and Form C of an edisylate salt of Compound 1).

(ii) Form B of Edisylate Salt of Compound 1

In certain embodiments, provided herein is Form B of an edisylate salt of Compound 1.

In one embodiment, Form B is crystalline. In one embodiment, Form B is substantially crystalline.

In one embodiment, the molar ratio of Compound 1 to ethane-1,2-disulfonic acid in Form B is about 4:3.

A representative XRPD pattern of Form B is provided in FIG. 38.

In one embodiment, provided herein is a solid form comprising an edisylate salt of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 4.8, 6.2, 7.8, 9.2, 10.4, 12.4, 12.7, 14.8, 15.2, 15.7, 16.4, 17.4, 18.4, 20.7, 22.1, 22.7, 23.7, 24.5, 25.0, 26.2, 27.3, 27.7, and 31.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising an edisylate salt of Compound 1, characterized by an XRPD pattern comprising peaks at approximately 4.8, 12.4, and 20.7° 2θ. In one embodiment, the XRPD pattern further comprises peaks at approximately 6.2, 7.8, and 15.2° 2θ. In one embodiment, the XRPD pattern comprises peaks at approximately 4.8, 6.2, 7.8, 12.4, 15.2, and 20.7° 2θ, in combination with at least one peak selected from approximately 10.4, 12.7, 17.4, and 18.4° 2θ.

In one embodiment, provided herein is a solid form comprising an edisylate salt of Compound 1, characterized by an XRPD pattern that matches the XRPD pattern presented in FIG. 38.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form B is provided in FIG. 39. In one embodiment, provided herein is a solid form comprising an edisylate salt of Compound 1, characterized by an FT-Raman spectrum that matches the FT-Raman spectrum presented in FIG. 39.

Representative differential scanning calorimetry (DSC) and thermal gravimetric analysis (TGA) thermograms of Form B are provided in FIG. 40.

In one embodiment, provided herein is a solid form comprising an edisylate salt of Compound 1, which exhibits, as characterized by DSC, a first thermal event with an onset temperature of about 153° C., and a second thermal event with an onset temperature of about 183° C. In one embodiment, the first thermal event also has a peak temperature of about 165° C., and the second thermal event also has a peak temperature of about 196° C. In one embodiment, provided herein is a solid form comprising an edisylate salt of Compound 1, characterized by a DSC thermogram that matches the DSC thermogram presented in FIG. 40.

In one embodiment, provided herein is a solid form comprising an edisylate salt of Compound 1, which exhibits a weight loss of about 0.5% upon heating from about 22° C. to about 50° C., and a weight loss of about 1.6% upon heating from about 125° C. to about 175° C. In one embodiment, without being limited by any particular theory, the weight losses correspond to the loss of water up to 50° C., followed by the loss of 2-propanol with melt from about 125° C. to about 175° C. In one embodiment, provided herein is a solid form comprising an edisylate salt of Compound 1, characterized by a TGA thermogram that matches the TGA thermogram presented in FIG. 40.

A representative polarized light microscopy (PLM) image of Form B is presented in FIG. 41.

In one embodiment, Form B is prepared by slurrying an edisylate salt of Compound 1 in a solvent. In one embodiment, Form B is prepared by slurrying an edisylate salt of Compound 1 (e.g., an amorphous form of the Edisylate salt of Compound 1) in a solvent for a period of time (e.g., about 48 h) while cycling the temperature (e.g., between about 5° C. and about 40° C.). In one embodiment, provided herein is a method for preparing Form B, comprising 1) obtaining a slurry of an edisylate salt of Compound 1 in a solvent; 2) stirring the slurry for a period of time (e.g., about 48 h) while cycling the temperature (e.g., between about 5° C. and about 40° C.); 3) optionally slowly cooling the slurry (e.g., from about 50° C. to about 5° C., at a rate of, e.g., about 0.1° C./min) followed by holding (e.g., at about 5° C.); 4) optionally slowly evaporating remaining solution at ambient conditions for a period of time (e.g., up to 7 days); and 5) collecting solids from the slurry by filtration and optionally drying the collected solids to provide Form B of an edisylate salt of Compound 1. In one embodiment, the solvent is 2-propanol.

In one embodiment, provided herein is a solid form comprising Form B of an edisylate salt of Compound 1 and one or more forms of a free base of Compound 1 (e.g., amorphous form and crystalline forms). In one embodiment, provided herein is a solid form comprising Form B of an edisylate salt of Compound 1 and one or more non-Form B forms of an edisylate salt of Compound 1 (e.g., Form A and Form C of an edisylate salt of Compound 1).

(iii) Form C of Edisylate Salt of Compound 1

In certain embodiments, provided herein is Form C of an edisylate salt of Compound 1.

In one embodiment, Form C is crystalline. In one embodiment, Form C is substantially crystalline.

A representative XRPD pattern of Form C is provided in FIG. 42.

In one embodiment, provided herein is a solid form comprising an edisylate salt of Compound 1, characterized by 1, 2, 3, 4, 5, 6, 7, 8, 9, or all of the peaks located at approximately the following positions: 4.5, 7.9, 8.9, 11.8, 15.2, 15.7, 18.6, 20.5, 20.7, and 23.7° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by all of the peaks.

In one embodiment, provided herein is a solid form comprising an edisylate salt of Compound 1, characterized by an XRPD pattern comprising peaks at approximately 4.5, 15.7, and 20.7° 2θ. In one embodiment, the XRPD pattern further comprises peaks at approximately 7.9, 20.5, and 23.7° 2θ. In one embodiment, the XRPD pattern comprises peaks at approximately 4.5, 7.9, 15.7, 20.5, 20.7, and 23.7° 2θ, in combination with at least one peak selected from approximately 8.9, 11.8, 15.2, and 18.6° 2θ.

In one embodiment, provided herein is a solid form comprising an edisylate salt of Compound 1, characterized by an XRPD pattern that matches the XRPD pattern presented in FIG. 42.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

In one embodiment, Form C of an edisylate salt of Compound 1 is prepared by heating Form A of an edisylate salt of Compound 1 to, e.g., at least 175° C.

In one embodiment, provided herein is a solid form comprising Form C of an edisylate salt of Compound 1 and one or more forms of a free base of Compound 1 (e.g., amorphous form and crystalline forms). In one embodiment, provided herein is a solid form comprising Form C of an edisylate salt of Compound 1 and one or more non-Form C forms of an edisylate salt of Compound 1 (e.g., Form A and Form B of an edisylate salt of Compound 1).

5.4 Methods of Use

The salts, solid forms and the pharmaceutical compositions comprising a salt of Compound 1 provided herein can be used in all the methods provided herein. The salts, solid forms and the pharmaceutical compositions comprising a salt of Compound 1 provided herein can be used in the treatment of all diseases, disorders or conditions provided herein.

Provided herein are methods for treating a subject suffering from or at risk for having a disease or disorder that is associated with an activated immune system, wherein the method comprises administering to said subject a salt of Compound 1 provided herein or a pharmaceutical composition thereof. Also provided herein are methods for treating a subject suffering from or at risk for having a disease or disorder that is associated with an activated immune system, wherein the method comprises administering to said subject a solid form comprising a salt of Compound 1 provided herein or a pharmaceutical composition thereof. In one embodiment, the disease or disorder can be treated and/or prevented with a selective $S1P_1$ receptor agonist.

In one embodiment, the disease or disorder is selected from the group consisting of rejection of transplanted organs or tissue; graft-versus-host diseases brought about by transplantation; autoimmune syndromes including rheumatoid arthritis; systemic lupus erythematosus; Hashimoto's thyroiditis; lymphocytic thyroiditis; multiple sclerosis; myasthenia gravis; type I diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; coeliac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

Provided herein are methods for treating a subject suffering from or at risk for having a disease or disorder, wherein the method comprises administering to said subject a salt of Compound 1 provided herein, a solid form comprising a salt of Compound 1 provided herein, or a pharmaceutical composition thereof, and wherein the disease or disorder is selected from the group consisting of rejection of transplanted organs or tissues such as kidney, liver, heart, lung, pancreas, cornea, and skin; graft-versus-host disease, e.g., brought about by stem cell transplantation; autoimmune syndromes including rheumatoid arthritis, multiple sclerosis, myasthenia gravis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; pollen allergies; type I diabetes; post-infectious autoimmune diseases including rheumatic fever and post-infectious glomerulonephritis; solid cancers; and tumor metastasis, e.g., metastasis of carcinoma.

Provided herein are methods for treating a subject suffering from or at risk for having an autoimmune disease or chronic inflammatory disorder, wherein the method comprises administering to said subject a salt of Compound 1 provided herein or a pharmaceutical composition thereof. Also provided herein are methods for treating a subject suffering from or at risk for having an autoimmune disease or chronic inflammatory disorder, wherein the method comprises administering to said subject a solid form comprising a salt of Compound 1 provided herein or a pharmaceutical composition thereof. In certain embodiments, the autoimmune or chronic inflammatory disorder is polymyositis, dermatomyositis, lupus nephritis, rheumatoid arthritis, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease, or multiple sclerosis.

In one embodiment, provided herein is a method of treating multiple sclerosis, wherein the method comprises administering to a patient in need thereof a salt of Compound 1 provided herein or a pharmaceutical composition thereof. In one embodiment, provided herein is a method of treating multiple sclerosis, wherein the method comprises administering to a patient in need thereof a solid form comprising a salt of Compound 1 provided herein or a pharmaceutical composition thereof. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1. In one embodiment, provided herein is a method for treating multiple sclerosis, comprising administering to a subject Form A of an HCl salt of Compound 1 provided herein. In one embodiment, provided herein is a method for treating multiple sclerosis, comprising administering to a subject Form B of an HCl salt of Compound 1 provided herein. In one embodiment, provided herein is a method for treating multiple sclerosis, comprising administering to a subject Form C of an HCl salt of Compound 1 provided herein. In one embodiment, provided herein is a method for treating multiple sclerosis, comprising administering to a subject Form A of an HBr salt of Compound 1 provided herein. In one embodiment, provided herein is a method for treating multiple sclerosis, comprising administering to a subject Form B of an HBr salt of Compound 1 provided herein. In one embodiment, provided herein is a method for treating multiple sclerosis, comprising administering to a subject Form A of a napadisylate salt of Compound 1 provided herein. In one embodiment, provided herein is a method for treating multiple sclerosis, comprising administering to a subject Form B of a napadisylate salt of Compound 1 provided herein. In one embodiment, provided herein is a method for treating multiple sclerosis, comprising administering to a subject Form C of a napadisylate salt of Compound 1 provided herein. In one embodiment, provided herein is a method for treating multiple sclerosis, comprising administering to a subject Form A of a 2-naphthalenesulfonate salt of Compound 1 provided herein. In one embodiment, provided herein is a method for treating multiple sclerosis, comprising administering to a subject Form A of an edisylate salt of Compound 1 provided herein. In one embodiment, provided herein is a method for treating multiple sclerosis, comprising administering to a subject Form B of an edisylate salt of Compound 1 provided herein. In one embodiment, provided herein is a method for treating multiple sclerosis, comprising administering to a subject Form C of an edisylate salt of Compound 1 provided herein. In one embodiment, the multiple sclerosis is relapsing-remitting multiple sclerosis, primary progressive multiple sclerosis, secondary progressive multiple sclerosis, or relapsing secondary progressive multiple sclerosis. In one embodiment, the multiple sclerosis is relapsing multiple sclerosis. In one embodiment, the multiple sclerosis is relapsing-remitting multiple sclerosis.

In one embodiment, provided herein is a method of treating psoriasis, wherein the method comprises administering to a patient in need thereof a salt of Compound 1 provided herein or a pharmaceutical composition thereof. In one embodiment, provided herein is a method of treating psoriasis, wherein the method comprises administering to a patient in need thereof a solid form comprising a salt of Compound 1 provided herein or a pharmaceutical composition thereof. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1. In one embodiment, provided herein is a method for treating psoriasis, comprising administering to a subject Form A of an HCl salt of Compound 1 provided herein. In one embodiment, provided herein is a method for treating psoriasis, comprising administering to a subject Form B of an HCl salt of Compound 1 provided herein. In one embodiment, provided herein is a method for treating psoriasis, comprising administering to a subject Form C of an HCl salt of Compound 1 provided herein. In one embodiment, provided herein is a method for treating psoriasis, comprising administering to a subject Form A of an HBr salt of Compound 1 provided herein. In one embodiment, provided herein is a method for treating psoriasis, comprising administering to a subject Form B of an HBr salt of Compound 1 provided herein. In one embodiment, provided herein is a method for treating psoriasis, comprising administering to a subject Form A of a napadisylate salt of Compound 1 provided herein. In one embodiment, provided herein is a method for treating psoriasis, comprising administering to a subject Form B of a napadisylate salt of Compound 1 provided herein. In one embodiment, provided herein is a method for treating psoriasis, comprising administering to a subject Form C of a napadisylate salt of Compound 1 provided herein. In one embodiment, provided herein is a method for treating psoriasis, comprising administering to a subject Form A of a 2-naphthalenesulfonate salt of Compound 1 provided herein. In one embodiment, provided herein is a method for treating psoriasis, comprising administering to a subject Form A of an edisylate salt of Compound 1 provided herein. In one embodiment, provided herein is a method for treating psoriasis, comprising administering to a subject Form B of an edisylate salt of Compound 1 provided herein. In one embodiment, provided herein is a method for treating psoriasis, comprising administering to a subject Form C of an edisylate salt of Compound 1 provided herein. In one embodiment, the psoriasis is chronic plaque psoriasis. In one embodiment, the psoriasis is moderate to severe chronic plaque psoriasis.

In one embodiment, provided herein is a method of treating polymyositis, wherein the method comprises administering to a patient in need thereof a salt of Compound 1 provided herein or a pharmaceutical composition thereof. In one embodiment, provided herein is a method of treating polymyositis, wherein the method comprises administering to a patient in need thereof a solid form comprising a salt of Compound 1 provided herein or a pharmaceutical composition thereof. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1. In one embodiment, provided herein is a method for treating polymyositis, comprising administering to a subject Form A of an HCl salt of Compound 1 provided herein. In one embodiment, provided herein is a method for treating polymyositis, comprising administering to a subject Form B of an HCl salt of Compound 1 provided herein. In one embodiment, provided herein is a method for treating polymyositis, comprising administering to a subject Form C of an HCl salt of Compound 1 provided herein. In one embodiment, provided herein is a method for treating polymyositis, comprising administering to a subject Form A of an HBr salt of Compound 1 provided herein. In one embodiment, provided herein is a method for treating polymyositis, comprising administering to a subject Form B of an HBr salt of Compound 1 provided herein. In one embodiment, provided herein is a method for treating polymyositis, comprising administering to a subject Form A of a napadisylate salt of Compound 1 provided herein. In one embodiment, provided herein is a method for treating polymyositis, comprising administering to a subject Form B of a napadisylate salt of Compound 1 provided herein. In one embodiment, provided herein is a method for treating polymyositis, comprising administering to a subject Form C of a napadisylate salt of Compound 1 provided herein. In one embodiment, provided herein is a method for treating polymyositis, comprising administering to a subject Form A of a 2-naphthalenesulfonate salt of Compound 1 provided herein. In one embodiment, provided herein is a method for treating polymyositis, comprising administering to a subject Form A of an edisylate salt of Compound 1 provided herein. In one embodiment, provided herein is a method for treating polymyositis, comprising administering to a subject Form B of an edisylate salt of Compound 1 provided herein. In one embodiment, provided herein is a method for treating polymyositis, comprising administering to a subject Form C of an edisylate salt of Compound 1 provided herein.

In one embodiment, provided herein is a method of treating graft versus host disease, wherein the method comprises administering to a patient in need thereof a salt of Compound 1 provided herein or a pharmaceutical composition thereof. In one embodiment, provided herein is a method of treating graft versus host disease, wherein the method comprises administering to a patient in need thereof a solid form comprising a salt of Compound 1 provided herein or a pharmaceutical composition thereof. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1. In one embodiment, provided herein is a method for treating graft versus host disease, comprising administering to a subject Form A of an HCl salt of Compound 1 provided herein. In one embodiment, provided herein is a method for treating graft versus host disease, comprising administering to a subject Form B of an HCl salt of Compound 1 provided herein. In one embodiment, provided herein is a method for treating graft versus host disease, comprising administering to a subject Form C of an HCl salt of Compound 1 provided herein. In one embodiment, provided herein is a method for treating graft versus host disease, comprising administering to a subject Form A of an HBr salt of Compound 1 provided herein. In one embodiment, provided herein is a method for treating graft versus host disease, comprising administering to a subject Form B of an HBr salt of Compound 1 provided herein. In one embodiment, provided herein is a method for treating graft versus host disease, comprising administering to a subject Form A of a napadisylate salt of Compound 1 provided herein. In one embodiment, provided herein is a method for treating graft versus host disease, comprising administering to a subject Form B of a napadisylate salt of Compound 1 provided herein. In one embodiment, provided herein is a method for treating graft versus host disease, comprising administering to a subject Form C of a napadisylate salt of Compound 1 provided herein. In one embodiment, provided herein is a method for treating graft versus host disease, comprising administering to a subject Form A of a 2-naphthalenesulfonate salt of Compound 1 provided herein. In one embodiment, provided herein is a method for treating graft versus host disease, comprising administering to a subject Form A of an edisylate salt of Compound 1 provided herein. In one embodiment, provided herein is a method for treating graft versus host disease, comprising administering to a subject Form B of an edisylate salt of Compound 1 provided herein. In one embodiment, provided herein is a method for treating graft versus host disease, comprising administering to a subject Form C of an edisylate salt of Compound 1 provided herein. In one embodiment, the graft versus host disease is symptomatic chronic GVHD.

In another embodiment, provided herein are methods for treating a subject suffering from or at risk for having a neurological disorder, wherein the method comprises administering to said subject a salt of Compound 1 provided herein or a pharmaceutical composition thereof. In another embodiment, provided herein are methods for treating a subject suffering from or at risk for having a neurological disorder, wherein the method comprises administering to said subject a solid form comprising a salt of Compound 1 provided herein or a pharmaceutical composition thereof. In one embodiment, the neurological disorder is Rett Syndrome. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1.

In another embodiment, provided herein are methods for treating a subject suffering from or at risk for renal or hepatic impairment, wherein the method comprises administering to said subject a salt of Compound 1 provided herein or a pharmaceutical composition thereof. In another embodiment, provided herein are methods for treating a subject suffering from or at risk for renal or hepatic impairment, wherein the method comprises administering to said subject a solid form comprising a salt of Compound 1 provided herein or a pharmaceutical composition thereof. In one embodiment, the solid form is selected from the group consisting Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1.

In another embodiment, provided herein are methods for treating a subject suffering from or at risk for a disease or disorder mediated by lymphocyte interactions, wherein the method comprises administering to said subject a salt of Compound 1 provided herein or a pharmaceutical composition thereof. In another embodiment, provided herein are methods for treating a subject suffering from or at risk for a disease or disorder mediated by lymphocyte interactions, wherein the method comprises administering to said subject a solid form comprising a salt of Compound 1 provided herein or a pharmaceutical composition thereof. In certain embodiments, the disease or disorder mediated by lymphocyte interactions is, for example, in transplantation, acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1.

In another embodiment, provided herein are methods for the treatment of a disease or disorder associated with sphingosine 1-phosphate and/or sphingosine 1-phosphate receptor, wherein the method comprises administering to said subject a salt of Compound 1 provided herein or a pharmaceutical composition thereof. In another embodiment, provided herein are methods for the treatment of a disease or disorder associated with sphingosine 1-phosphate and/or sphingosine 1-phosphate receptor, wherein the method comprises administering to said subject a solid form comprising a salt of Compound 1 provided herein or a pharmaceutical composition thereof. In certain embodiments, the disease or disorder associated with sphingosine 1-phosphate is multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, or Graves' disease. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1

In another embodiment, provided herein are methods for the treatment of a disease or disorder associated with the interferon alpha receptor 1, wherein the method comprises administering to said subject a salt of Compound 1 provided herein or a pharmaceutical composition thereof. In another embodiment, provided herein are methods for the treatment of a disease or disorder associated with the interferon alpha receptor 1, wherein the method comprises administering to said subject a solid form comprising a salt of Compound 1 provided herein or a pharmaceutical composition thereof. In certain embodiments, the disease or disorder associated with the interferon alpha receptor is psoriasis, ulcerative colitis, systemic lupus, multiple sclerosis, or rheumatoid arthritis. In one embodiment, the solid form is selected from the group consisting of Form A, Form B, and Form C of an HCl salt of Compound 1, Form A and Form B of an HBr salt of Compound 1, Form A, Form B, and Form C of a napadisylate salt of Compound 1, Form A of a 2-naphthalenesulfonate salt of Compound 1, Form A, Form B, and Form C of an edisylate salt of Compound 1.

In certain embodiments, the methods provided herein comprise administering a salt of Compound 1 or a pharmaceutical composition thereof, in combination with one or more additional therapeutic agents. In certain embodiments, the methods provided herein comprise administering a solid form comprising a salt of Compound 1 or a pharmaceutical composition thereof, in combination with one or more additional therapeutic agents. In one embodiment, the additional therapeutic agents can be selected from the group comprising or consisting of immunosuppressants, corticosteroids, nonsteroidal anti-inflammatory drugs, cytotoxic drugs, adhesion molecule inhibitors, cytokines, cytokine inhibitors, cytokine receptor antagonists and recombinant cytokine receptors.

In one embodiment, the additional therapeutic agent is an immunosuppressant agent. In one embodiment, the additional therapeutic agent is selected from the group consisting of cyclosporin, daclizumab, basiliximab, everolimus, tacrolimus (FK506), azathiopirene, leflunomide, and 15-deoxyspergualin.

In one embodiment, the additional therapeutic agent is selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl) ethyl methyl (2E)but-2-ene-1,4-dioate, or a pharmaceutically acceptable salt thereof.

5.5 Pharmaceutical Compositions

Salts of Compound 1 provided herein are useful for the preparation of pharmaceutical compositions, comprising an effective amount of a salt of Compound 1 provided herein, and a pharmaceutically acceptable vehicle, carrier, diluent, or excipient, or a mixture thereof. Solid forms comprising a salt of Compound 1 provided herein are useful for the preparation of pharmaceutical compositions, comprising an effective amount of a solid form comprising a salt of Compound 1 provided herein, and a pharmaceutically acceptable vehicle, carrier, diluent, or excipient, or a mixture thereof. In certain embodiments, the pharmaceutically acceptable carrier is hydroxypropyl methylcellulose. In some embodiments, the pharmaceutical compositions described herein are suitable for oral, parenteral, mucosal, transdermal or topical administration.

5.6 Oral Administration

The pharmaceutical compositions provided herein may be administered orally, for example in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, the pharmaceutically acceptable carrier or excipient is selected from the group consisting of lactose (e.g., as lactose monohydrate); microcrystalline cellulose; non-basic polymers (e.g., homopolymers of cross-linked N-vinyl-2-pyrrolidone (crospovidone), hypromellose (hydroxypropylmethyl cellulose), and ethyl cellulose); waxes; colloidal silicon dioxide; stearic acid; hydrogenated vegetable oil; mineral oil; polyethylene glycol (e.g., polyethylene glycol 4000-6000); glyceryl palmitostearate; and glyceryl behenate. In another embodiment, the pharmaceutically acceptable carrier or excipient is microcrystalline cellulose.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1% to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and L-tartaric acid. Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The salts of Compound 1 provided herein can be formulated as an oral dosage form. In certain embodiments the oral dosage form comprises one or more of the salts of Compound 1 provided herein. In certain embodiments the oral dosage form comprises one or more of the salts of Compound 1 provided herein, in an amount that provides at least 0.001 mg, at least 0.005 mg, at least 0.01 mg, at least 0.05 mg, at least 0.1 mg, at least 0.5 mg, at least 1 mg, at least 2 mg, at least 5 mg, at least 10 mg, at least 20 mg, at least 30 mg, at least 40 mg, or at least 50 mg of Compound 1. In certain embodiments the oral dosage form comprises one or more of the salts of Compound 1 provided herein, in an amount that provides about 1 mg, about 2 mg, about 5 mg, about 10 mg, about 20 mg, about 30 mg, about 40 mg, or about 50 mg of Compound 1. In one embodiment, the oral dosage form comprises one or more of the salts of Compound 1 provided herein, in an amount that provides about 20 mg of Compound 1.

The solid forms and the pharmaceutical compositions comprising a salt of Compound 1 provided herein can be formulated as an oral dosage form. In certain embodiments the oral dosage form comprises one or more of the solid forms comprising a salt of Compound 1 provided herein. In certain embodiments the oral dosage form comprises one or more of the solid forms comprising a salt of Compound 1 provided herein, in an amount that provides at least 0.001 mg, at least 0.005 mg, at least 0.01 mg, at least 0.05 mg, at least 0.1 mg, at least 0.5 mg, at least 1 mg, at least 2 mg, at least 5 mg, at least 10 mg, at least 20 mg, at least 30 mg, at least 40 mg, or at least 50 mg of Compound 1. In certain embodiments the oral dosage form comprises one or more of the solid forms comprising a salt of Compound 1 provided herein, in an amount that provides about 1 mg, about 2 mg, about 5 mg, about 10 mg, about 20 mg, about 30 mg, about 40 mg, or about 50 mg of Compound 1. In one embodiment, the oral dosage form comprises one or more of the solid forms comprising a salt of Compound 1 provided herein, in an amount that provides about 20 mg of Compound 1.

5.7 Parenteral Administration

The pharmaceutical compositions provided herein can be administered parenterally, for example, by injection, infusion, or implantation techniques, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

5.8 Dosage

In certain embodiments, a dose of Compound 1 used in the methods provided herein is between about 0.5 mg and about 1000 mg per day. In certain embodiments, the dose is between about 1 mg and about 500 mg per day. In certain embodiments, the dose is between about 5 mg and about 200 mg per day.

In certain embodiments, a maintenance dose for Compound 1 used in the methods provided herein is about 10 mg or about 20 mg orally once daily. In certain embodiments, a maintenance dose for Compound 1 is about 20 mg orally once daily. In certain embodiments, the maintenance dose of Compound 1 is 20 mg once daily. In certain embodiments, the maintenance dose of Compound 1 is 20 mg administered as a monotherapy.

In certain embodiments, the Compound 1 can be administered orally once daily a dose of 10 mg for 7 days followed by 20 mg on day 8.

In certain embodiments, the dosing regimen can comprise administration of: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by: (a) a maintenance dose of 10 mg of Compound 1 administered orally once daily from day 12 onwards; or (b) 10 mg of Compound 1 administered orally once daily for 2, 3 or 4 days (i.e., on days 12 and 13; days 12, 13, and 14; or days 12, 13, 14, and 15), especially for 3 days (i.e., on days 12, 13, and 14), followed by a maintenance dose of 20 mg of Compound 1 to be administered orally once daily (i.e., from the day following the day of the last administration of the 10 mg dose onwards).

In certain embodiments, the dosing regimen can comprise administration of: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by 10 mg of Compound 1 administered orally once daily for 2, 3 or 4 days, especially for 3 days; followed by the maintenance dose of 20 mg of Compound 1 administered orally once daily.

In certain embodiments, 10 mg of Compound 1 can be administered orally once daily on days 12, 13, and 14; followed by a maintenance dose of 20 mg of Compound 1 administered orally once daily from day 15 onwards.

In certain embodiments, the dosing regimen can comprise administration of: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by the maintenance dose of 10 mg of Compound 1 administered orally once daily from day 12 onwards.

For clarity reasons, it is noted that the once daily oral doses referred to herein i) refer to the amount of Compound 1 in their free form. In case that for example a pharmaceutically acceptable salt of Compound 1 is used, the amounts given above will need to be adapted accordingly.

6. EXAMPLES

The following Examples are presented by way of illustration, not limitation.

6.1 Analytical Methods

FT-Raman Spectroscopy. Raman spectra were collected with a Nicolet NXR9650 or NXR 960 spectrometer (Thermo Electron) equipped with 1064 nm Nd:YVO4 excitation laser, InGaAs and liquid-N2 cooled Ge detectors, and a MicroStage. All spectra were acquired at 4 cm$^{-1}$ resolution, 64 scans, using Happ-Genzel apodization function and 2-level zero-filling.

Polarized-Light Microscopy (PLM). The photomicrographs were collected using Olympus BX60 polarized-light microscope equipped with Olympus DP70 camera.

Powder X-Ray Diffraction (PXRD). PXRD diffractograms were acquired on PANalytical X'Pert Pro diffractometer using Ni-filtered Cu Kα (45 kV/40 mA) radiation and a step size of 0.03° 2θ and X'celeratorTMRTMS (Real Time Multi-Strip) detector. Configuration on the incidental beam side: variable divergence slits (10 mm irradiated length), 0.04 rad Soller slits, fixed anti-scatter slit (0.50°), and 10 mm beam mask. Configuration on the diffracted beam side: variable anti-scatter slit (10 mm observed length) and 0.02 rad Soller slit. Samples were mounted flat on zero-background Si wafers.

Powder X-Ray Diffraction (PXRD). PXRD diffratograms were also obtained on a Rigaku SmartLab Guidance diffractometer with Cu-Kα radiation and D/teX Ultra detector. The powder samples were deposited on a zero-background polished silicon sample holder and were spun during measurement. Measurements were performed as follows: 40 kV/44 mA tube power, 0.02° 2θ step size, 5° 2θ/min scan rate, and 3-40° 2θ scan range.

Differential Scanning Calorimetry (DSC). DSC was conducted with a TA Instruments Q100 or Q2000 differential scanning calorimeter equipped with an autosampler and a refrigerated cooling system under 40 mL/min N2 purge. DSC thermograms of screening samples were obtained at 15° C./min in crimped Al pans, unless noted otherwise. DSC thermograms of input and scaled-up materials were obtained at 10° C./min in crimped Al pans, unless noted otherwise.

Thermogravimetric Analysis (TGA). TGA thermograms were obtained with a TA Instruments Q50 thermogravimetric analyzer under 40 mL/min N2 purge in Pt or Al pans. TGA thermograms of screening samples were obtained at 15° C./min, unless noted otherwise. TGA thermograms of input and scaled-up material were obtained at 10° C./min, unless noted otherwise.

Thermogravimetric Analysis with IR Off-Gas Detection (TGA-IR). TGA-IR was conducted with a TA Instruments Q5000 thermogravimetric analyzer interfaced to a Nicolet 6700 FT-TR spectrometer (Thermo Electron) equipped with an external TGA-IR module with a gas flow cell and DTGS detector. TGA was conducted with 25 mL/min N2 flow and heating rate of 15° C./min in Pt or Al pans. IR spectra were collected at 4 cm$^{-1}$ resolution and 32 scans at each time point.

Proton Nuclear Magnetic Resonance ($^1$H NMR). The $^1$H NMR spectra were collected using Agilent DD2 500 MHz spectrometer with TMS reference. Samples were dissolved in DMSO-d6.

Ion Chromatography (IC). Ion chromatography was performed on a Dionex ICS-3000. Column: Dionex IonPac AS12A 4×200 mm; Detection: Suppressed conductivity, ASRS 300 with suppressor current at 22 mA; Eluent (2.7 mM $Na_2CO_3$/0.3 mM $NaHCO_3$) at 1.5 mL/min.

High-performance Liquid Chromatography (HPLC). HPLC analyses were conducted with an Agilent 1260 Infinity system equipped with a G1311B Quad pump, G1329B Autosampler, G1330B autosampler thermostat, G1316A Thermostatted Column Compartment, and G4212B diode array detector.

| Column | Sunfire C18, 3.5 µm, 3.0 × 100 mm | | |
|---|---|---|---|
| Mobile phase A | Water with 0.05% TFA (v/v) | | |
| Mobile phase B | Acetonitrile with 0.05% TFA (v/v) | | |
| Gradient | Time (min) | % A | % B |
| | 0 | 90 | 10 |
| | 8.00 | 5 | 95 |
| | 8.10 | 90 | 10 |
| | 11.00 | 90 | 10 |
| Flow rate | 0.5 mL/min | | |
| Column temperature | 40° C. | | |
| Injection volume | 1 or 2 µL | | |
| Detection | UV VWD at 348 nm | | |

Dynamic Vapor Sorption (DVS): A portion of a test sample was loaded into an aluminum sample holder and tested using a DVS-Intrinsic dynamic gravimetric water sorption analyzer from Surface Measurement Systems. The test was run in one continuous adsorption/desorption cycle from 0-95% relative humidity (RH) range with step size of 5% or 10% RH and dm/dt change of 0.001%/min in 15 min with a minimum of 10 min and a maximum of 360 min. The sample temperature is maintained at 25° C. The nitrogen gas flow rate is 200 standard cubic centimeters per minute (sccm). Humidity is precisely controlled through mixing dry and water saturated gas. The weight change of the sample as a function of % RH is constantly monitored and recorded through an SMS Ultrabalance.

6.2 Crystal Salt Form Screen

Compound 1 can be prepared by methods known in the art. See, e.g., International Patent Application Publication No. WO 2005/054215.

The PXRD of the starting material batch (free base) used in the crystal salt form screen is presented in FIG. 43, and the DSC/TGA is presented in FIG. 44.

Salt screening of Compound 1 involved 96 salt formation experiments.

Counterion Selection

Compound 1 has one weakly basic site with predicted $pK_a$ of 0.9. A total of 12 acids exhibiting suitable $pK_a$ values were selected for salt formation. One stoichiometric equivalent of acid was dosed in all experiments. Table 1 provides a summary of the utilized acids.

TABLE 1

Acids Used in the Salt Screen

| No. | Acid | Dosing Method |
| --- | --- | --- |
| 1 | HCl | 3M in water |
| 2 | HBr | 3M in water |
| 3 | Naphthalene-1,5-disulfonic | 1.5M in water |
| 4 | Sulfuric | 2.5M in water |
| 5 | Ethane-1,2-disulfonic | 3M in water |
| 6 | Camphor-10-sulfonic | 3M in water |
| 7 | Ethanesulfonic | 3M in water |
| 8 | p-Toluenesulfonic | 3M in water |
| 9 | Trifluoroacetic | 3M in water |
| 10 | Methanesulfonic | 3M in water |
| 11 | Naphthalene-2-sulfonic | 3M in THF |
| 12 | Benzenesulfonic | 3M in water |

Solvent Selection

The solvents initially selected for the salt screen are shown in Table 2. The solvents were selected based on solubility of the parent, polarity, and chemical diversity.

TABLE 2

Solvents Selected in the Salt Screen

| No. | Solvent | Description |
| --- | --- | --- |
| 1 | Toluene | Aromatic, nonpolar, aprotic |
| 2 | Methyl tert-Butyl Ether (MTBE) | Ether, moderately nonpolar, aprotic |
| 3 | 1-Butanol | Alcohol, moderately polar, protic |
| 4 | Methyl iso-Butyl Ketone (MIBK) | Ketone, moderately polar, aprotic |
| 5 | Ethyl Acetate (EtOAc) | Ester, moderately polar, aprotic |
| 6 | Acetone | Ketone, moderately polar, aprotic |
| 7 | Acetonitrile (MeCN) | Nitrile, polar, aprotic |
| 8 | 2-Propanol (IPA) | Alcohol, moderately polar, protic |

Modes of Crystallization

The modes of crystallization utilized for the salt screening studies are as follows:
1. Temperature-cycled ripening from 40-5° C. after counterion addition (TC1).
2. Fast evaporation of solvents under reduced pressure followed by temperature-cycled ripening from 40-5° C. in neat solvents (TC2).
3. Controlled cooling of samples from 50-5° C. at 0.1° C./min followed by hold at 5° C. (CC).
4. Slow evaporation of solvents at RT for up to seven days (EV).

Salt Screening Procedure

Details of the screening procedure and the various crystallization modes are detailed below. The procedure utilized is as follows:
1. Dispensed 300 µL of solvents into 2-mL HPLC vials containing starting material batch of Compound 1.
2. Added one stoichiometric equivalent of the acid to the vial.
3. Stirred the solutions and suspensions/gums/oils while cycling the temperature between 40° C. and 5° C. at a rate of 0.5° C./min for two days (TC1).
4. Evaporated solutions and amorphous suspensions/gums/oils rapidly under reduced pressure by Genevac.
5. Added original solvent to the solids (200 µL).
6. Stirred the solutions and amorphous suspensions/gums/oils while cycling the temperature between 40° C. and 5° C. at a rate of 0.5° C./min for two days (TC2).
7. Heated the samples to 50° C., then slowly cooled samples from 50-5° C. at 0.1° C./min followed by hold at 5° C. (CC).
8. Evaporated remaining solutions at ambient conditions for up to 7 days (EV).

Isolation and Characterization

All samples were examined for crystallinity by PLM at the end of each crystallization mode. If an experiment yielded a birefringent hit, the solids were isolated by vacuum filtration and air-dried with vacuum pull at room temperature. The solids were analyzed by FT-Raman spectroscopy and/or PXRD.

FT-Raman spectra/PXRD pattern of samples prepared using the same acid were compared to determine whether they were the same crystal form. Representative samples from each unique group were subjected to further characterization using PXRD, DSC, TGA and TGA-IR analyses (as appropriate).

Salt Screening Results

Table 3 shows the salt screen results. Salt screening experiments led to crystalline salt hits from 6 of the 12 acids. All remaining experiments yielded non-crystalline products (gums/amorphous glassy material) or yielded solids consistent with free base. Detailed characterization of the selected crystalline salts including preparation is provided below.

TABLE 3

Salt Screening Results

| Acid | Toluene | MTBE | 1-Butanol | MIBK | Ethyl Acetate | Acetone | Acetonitrile | 2-propanol |
| --- | --- | --- | --- | --- | --- | --- | --- | --- |
| HCl | Am | Am | FB (PC) | A | A | Am | A | D/D |
| HBr | Am | Am | D/D | A | Am | Am | D/D | A |
| 1,5-Naphthalenedisulfonic | C | C | B | B | Am | B | B | A |
| Sulfuric | Am | Am | FB (PC) | Am | Am | Am | Am | FB (PC) |
| 1,2-Ethanedisulfonic | A | A | A | A | A | A | A | B |
| Camphor-10-sulfonic | Am | Am | FB (PC) | FB (PC) | Am | Am | Am | FB (PC) |
| Ethanesulfonic | Am | Am | FB (PC) | A | Am | Am | Am | FB (PC) |
| p-Toluenesulfonic | Am | Am | FB (PC) | Am | D/D | Am | Am | FB (PC) |
| Trifluoroacetic | Am | FB (C) | D/D | Am | Am | Am | Am | FB (C) |
| Methanesulfonic | Am | Am | FB (PC) | Am | Am | Am | Am | D/D |
| 2-Naphthalenesulfonic | Am | Am | Am | Am | Am | Am | Am | A |
| Benzenesulfonic | Am | Am | FB (PC) | Am | Am | Am | Am | D/D |

Single letter (A, B, C, etc.) = Crystalline salt
FB (C) = Crystalline free base
FB (PC) = Poorly crystalline free base
D/D = Discolored solids/degradation
Am = amorphous, gum, or oil Salt screening experiments led to crystalline hits from eight acids: HCl, HBr, naphthalene-1,5-disulfonic, ethane-1,2-disulfonic, ethanesulfonic, p-toluenesulfonic, trifluoroacetic, 2-naphthalenesulfonic acids. The hit from p-toluenesulfonic was determined to be primarily not the desired Compound 1, while the two hits from trifluoroacetic acid were determined to be different forms of Compound 1 free base rather than salt hits. An additional hit from ethanesulfonic acid was likely a salt.

The HCl, HBr, napadisylate, 2-naphthalenesulfonate, and edisylate salts were scaled up on 150-300 mg scale for detailed characterization.

6.3 Preparations and Characterization of Crystalline Salts (a) HCl Salt
Preparation of Form A of the HCl Salt Ethyl acetate (3.0 mL; 15 vol) was added to starting material of Compound 1 (214 mg). One equivalent of hydrochloric acid (3M in water; 155 µL) was added. The yellow solution was concentrated in vacuo to dryness, resulting in a yellow oil. Ethyl acetate (10 vol; 2.0 mL) and seed crystals of Form A of the HCl salt were added to the mixture. The mixture was temperature-cycled from 40-5° C. overnight. The solids were isolated by filtration under vacuum and air-dried for about 20 minutes. The yield was 77.6% (179 mg), and the solids were consistent with Form A of the HCl salt.

Characterization of Form A of the HCl Salt

The PXRD of Form A is presented in FIG. 1, the Raman spectrum of Form A is presented in FIG. 2, the DSC/TGA of Form A is presented in FIG. 3, and the PLM of Form A is presented in FIG. 4. The HCl salt was crystalline by PXRD, and the material was birefringent with tiny irregular particles by PLM. DSC analysis showed a large, broad endotherm with onset temperature of about 55° C. and a small endotherm with onset temperature of about 110° C. TGA-IR analysis showed a weight loss of 4.8% water and trace ethyl acetate up to 100° C. followed by loss of trace ethyl acetate and HCl gas above 100° C. Form A was determined to be a 1:1 HCl salt by ion-chromatography.

Preparation of Form B and Form C of the HCl Salt

Starting material of Compound 1 (401 mg) was dissolved in acetonitrile (15 vol; 6.0 mL). One equivalent of hydrochloric acid (3M in water; 290 µL) was added. The yellow solution was concentrated in vacuo to dryness, resulting in a mixture of solids and yellow oil. Acetonitrile (10 vol; 4.0 mL) and seed crystals of Form A of the HCl salt were added to the mixture. The slurry was heated at 40° C. for 1 hr, then slowly cooled to RT at 0.1° C./min. The mixture was stirred at RT overnight. A test aliquot was filtered and analysis by PXRD showed a unique pattern (Form B of HCl salt). The remaining solids were isolated by filtration under vacuum and air-dried for about 20 minutes. The yield was 82.2% (356 mg). PXRD analysis showed that the resultant solids were a new form of the HCl salt, Form C.

Characterization of Form B of the HCl Salt

The PXRD of Form B is presented in FIG. 5. The HCl salt was crystalline by PXRD.

Characterization of Form C of the HCl Salt

The PXRD of Form C is presented in FIG. 6, the Raman spectrum of Form C is presented in FIG. 7, the DSC/TGA of Form C is presented in FIG. 8, and the PLM of Form C is presented in FIG. 9. The HCl salt was crystalline by PXRD, and the material was birefringent with tiny irregular particles by PLM. DSC analysis showed a large, broad endotherm with onset temperature of about 98° C. and a small endotherm with onset temperature of about 135° C. TGA-IR analysis showed a weight loss of about 3.2% of water and then trace acetonitrile up to 100° C., followed by loss of acetonitrile and then HCl gas above 100° C. Proton NMR shows about 0.8eq of acetonitrile, which suggests that Form C may be a solvated form. Form C was determined to be a 1:1 HCl salt by ion-chromatography.

(b) HBr Salt
Preparation of Form A of the HBr Salt

MIBK (300 µL; 15 vol) was added to starting material of Compound 1 (20.1 mg). One equivalent of hydrobromic acid (3M in water; 14.5 µL) was added. The mixture was temperature-cycled from 40-5° C. for three days. The mixture of solution and oil was concentrated in vacuo to dryness, resulting in a yellow oil. MIBK (10 vol; 200 µL) was added. The mixture was temperature-cycled from 40-5° C. for two days. The solids were isolated by filtration under vacuum and air-dried.

Characterization of Form A of the HBr Salt

The PXRD of Form A is presented in FIG. 10, the Raman spectrum of Form A is presented in FIG. 11, and the DSC/TGA of Form A is presented in FIG. 12. The HBr salt was crystalline by PXRD. DSC analysis showed a broad endotherm with onset temperature of about 53° C. and a second endotherm with onset temperature of about 128° C. TGA-IR analysis showed a weight loss of about 3.2% attributed to water up to about 116° C. and additional weight loss of about 4.5% attributed to HBr up to 198° C.

Preparation of Form B of the HBr Salt

MIBK (3.0 mL; 15 vol) was added to starting material of Compound 1 (222 mg). One equivalent of hydrobromic acid (3M in water; 161 µL) was added. The oily mixture was concentrated in vacuo to dryness, resulting in a yellow oil. MIBK (10 vol; 2.0 mL) and seed crystals of Form A of the HBr salt were added to the mixture. The slurry was heated at 40° C. for 1 hr, then slowly cooled to RT at 0.1° C./min. The mixture was stirred at RT overnight. The solids were isolated by filtration under vacuum and air-dried for about 20 minutes. The yield was 80.2% (209 mg), and the solids were consistent by PXRD analysis with a new form, Form B, of the HBr salt.

Characterization of Form B of the HBr Salt

The PXRD of Form B is presented in FIG. 13, the Raman spectrum of Form B is presented in FIG. 14, the DSC/TGA of Form B is presented in FIG. 15, and the PLM of Form B is presented in FIG. 16. The HBr salt was crystalline by PXRD, and the material was birefringent with tiny irregular particles by PLM. DSC analysis showed a large, broad endotherm with onset temperature of about 41° C. and a small endotherm with onset temperature of about 133° C. TGA-IR analysis showed a weight loss of about 6.6% of water and then HBr gas up to about 150° C. Form B was determined to be a 1:1 HBr salt by ion-chromatography.

(c) Napadisylate Salt
Preparation of Form A of the Napadisylate Salt

2-Propanol (3.0 mL; 15 vol) was added to starting material of Compound 1 (207 mg). One equivalent of naphthalene-1,5-disulfonic acid (1.5M in water; 299 µL) was added, followed by seed crystals of Form A of the napadisylate salt to the mixture. The mixture was temperature-cycled from 40-5° C. overnight. The solids were isolated by filtration under vacuum and air-dried for about 20 minutes. The yield was about 70.1% (190 mg), and the solids were consistent with Form A of the hemi-napadisylate salt.

Characterization of Form A of the Napadisylate Salt

The PXRD of Form A is presented in FIG. 17, the Raman spectrum of Form A is presented in FIG. 18, the DSC/TGA of Form A is presented in FIG. 19, the PLM of Form A is presented in FIG. 20, and the DVS isotherm of Form A is presented in FIG. 21. The napadisylate salt was crystalline by PXRD, and the material was birefringent with tiny irregular particles by PLM. Thermal analysis showed <0.1% weight loss up to about 225° C. in TGA and a single sharp endotherm at about 235.4° C. in DSC. Form A was determined to be a hemi-salt (that is 1:2 naphthalene-1,5-disulfonic acid: free base) by proton NMR. The water uptake of about 1.55% at 85% RH at 25° C. in DVS indicates that the material is slightly hygroscopic in nature. There was no significant change in the XRPD pattern at the end of the adsorption/desorption cycle when compared to that of the as-prepared Form A of napadisylate salt.

Preparation of Form B of the Napadisylate Salt

Starting material of Compound 1 (221 mg) was dissolved in acetonitrile (15 vol; 3.0 mL). One equivalent of naphthalene-1,5-disulfonic acid (1.5M in water; 320 µL) was added. The oily yellow mixture was concentrated in vacuo to dryness, resulting in yellow solids. Acetonitrile (10 vol; 2.0 mL) and seed crystals of Form B of the napadisylate salt were added to the mixture. The mixture was temperature-cycled from 40-5° C. overnight. The solids were isolated by filtration under vacuum and air-dried for about 20 minutes. The yield was about 92.0% (331 mg), and the solids were consistent with Form B of the napadisylate salt.

Characterization of Form B of the Napadisylate Salt

The PXRD of Form B is presented in FIG. 22, the Raman spectrum of Form B is presented in FIG. 23, the DSC/TGA of Form B is presented in FIG. 24, and the PLM of Form B is presented in FIG. 25. The napadisylate salt was crystalline by PXRD, and the material was birefringent with tiny irregular particles by PLM. Thermal analysis showed about 7.0% weight loss of water up to 150° C. in TGA and a very broad endotherm with onset temperature of about 43.0° C. followed by a second endotherm with onset temperature of about 149.5° C. Form B was determined to be a mono-napadisylate salt (1:1 naphthalene-1,5-disulfonic acid: free base) by proton NMR.

Preparation of Form C of the Napadisylate Salt

Toluene (15 vol; 3.0 mL) was added to starting material of Compound 1 (218 mg). One equivalent of naphthalene-1,5-disulfonic acid (1.5M in water; 315 µL) was added. The oily yellow mixture was concentrated in vacuo to dryness, resulting in yellow solids. Toluene (10 vol; 2.0 mL) and seed crystals of Form C of the napadisylate salt were added to the mixture. The mixture was temperature-cycled from 40-5° C. overnight. The solids were isolated by filtration under vacuum and air-dried for about 20 minutes. The yield was about 93.1% (330 mg), and the solids were consistent with Form C of the napadisylate salt.

Characterization of Form C of the Napadisylate Salt

The PXRD of Form C is presented in FIG. 26, the Raman spectrum of Form C is presented in FIG. 27, the DSC/TGA of Form C is presented in FIG. 28, and the PLM of Form C is presented in FIG. 29. The napadisylate salt was crystalline by PXRD, and the material was birefringent with tiny irregular particles by PLM. Thermal analysis showed about 9.1% weight loss of water up to about 150° C. in TGA and a very broad double endotherm with onset temperature of about 117.4° C. in DSC. Form C was determined to be a mono-napadisylate salt (1:1 naphthalene-1,5-disulfonic acid: free base) by proton NMR.

(d) 2-Naphthalenesulfonate Salt

Preparation of Form A of the 2-Naphthalenesulfonate Salt

2-Propanol (15 vol; 3.4 mL) was added to starting material of Compound 1 (225 mg). One equivalent of solid 2-naphthalenesulfonic acid hydrate (110 mg) and seed crystals of Form A of the 2-naphthalenesulfonate salt were added. The mixture mostly dissolved then observed an increased precipitation. The mixture was temperature-cycled with stirring from 40-5° C. overnight. The solids were isolated by filtration under vacuum and air-dried for about 20 minutes. The yield was about 80.7% (263 mg), and the solids were consistent with Form A of the 2-naphthalenesulfonate salt.

Characterization of Form A of the 2-Naphthalenesulfonate Salt

The PXRD of Form A is presented in FIG. 30, the Raman spectrum of Form A is presented in FIG. 31, the DSC/TGA of Form A is presented in FIG. 32, and the PLM of Form A is presented in FIG. 33. The 2-naphthalenesulfonate salt was crystalline by PXRD, and the material was birefringent with tiny irregular particles by PLM. Thermal analysis showed about 1.2% weight loss of likely entrained 2-propanol in TGA and a sharp endotherm with onset temperature of about 186.3° C. in DSC. Form A was determined to be a mono salt (1:1 2-napthalenesulfonic acid: free base) and contained ~0.14eq of 2-propanol by proton NMR.

(e) Edisylate Salt

Preparation of Form A of the Edisylate Salt

Acetone (15 vol; 3.0 mL) was added to starting material of Compound 1 (207 mg). One equivalent of ethane-1,2-disulfonic acid (3.0M in water; 150 µL) and seed crystals of Form A of the edisylate salt were added. The mixture mostly dissolved then observed an increased precipitation. The mixture was stirred and cooled from 25-5° C. and held at 5° C. overnight. The solids were isolated by filtration under vacuum and air-dried for about 20 minutes. The yield was about 59.2% (173 mg), and the solids were consistent with Form A of the edisylate salt.

Characterization of Form A of the Edisylate Salt

The PXRD of Form A is presented in FIG. 34, the Raman spectrum of Form A is presented in FIG. 35, the DSC/TGA of Form A is presented in FIG. 36, and the PLM of Form A is presented in FIG. 37. The edisylate salt was crystalline by PXRD, and the material was birefringent with tiny irregular particles by PLM. Thermal analysis showed about 6.2% weight loss of water up to about 125° C. in TGA and a double endotherm with onset temperature of about 68.9° C. followed by a sharp endotherm with onset temperature of about 207.2° C. in DSC. Form A was determined to be a mono salt (1:1 ethane-1,2-disulfonic acid: free base) by proton NMR.

Preparation of Form B of the Edisylate Salt

2-Propanol (15 vol; 3.0 mL) was added to starting material of Compound 1 (206 mg). One equivalent of ethane-1,2-disulfonic acid (3.0M in water; 149 µL) and seed crystals of Form B of the edisylate salt were added. The mixture was temperature-cycled from 40-5° C. overnight with the last cycled cooling from 40-25° C. The solids were isolated by filtration under vacuum and air-dried for about 20 minutes. The yield was about 57.2% (154 mg), and the solids were consistent with Form B of the edisylate salt.

Characterization of Form B of the Edisylate Salt

The PXRD of Form B is presented in FIG. 38, the Raman spectrum of Form B is presented in FIG. 39, the DSC/TGA of Form B is presented in FIG. 40, and the PLM of Form B is presented in FIG. 41. The edisylate salt was crystalline by PXRD, and the material was birefringent with tiny irregular particles by PLM. TGA-IR analysis showed two weight losses, of about 0.5% attributed to surface water and followed by about 1.6% weight loss of likely entrained 2-propanol. DSC analysis showed two endotherms with onset temperatures of about 153.2° C. and 182.8° C., respectively. Form B was determined to be a 3:4 (ethane-1,2-disulfonic acid: free base) salt by proton NMR, which indicates that it has complex stoichiometry.

Preparation and Characterization of Form C of the Edisylate Salt

Approximately 5 mg of Form A of edisylate salt was heated to 175° C. at 15° C./min in TGA-IR. The residual yellow solids were crystalline by PXRD analysis. The PXRD of Form C is presented in FIG. 42.

TABLE 4

HPLC Analysis of Crystalline Salts

| Counterion/Form | Compound 1 (% Area) | Total Impurities (% area) |
|---|---|---|
| HCl (Form A) | 94.41 | 5.59 |
| HCl (Form C) | 99.31 | 0.69 |
| HBr (Form B) | 99.17 | 0.83 |
| Napadisylate (Form A) | 99.48 | 0.52 |
| Napadisylate (Form B) | 99.26 | 0.74 |
| Napadisylate (Form C) | 96.92 | 3.08 |
| 2-Naphthalenesulfonate (Form A) | 98.24 | 1.76 |
| Edisylate (Form A) | 99.10 | 0.90 |
| Edisylate (Form B) | 97.95 | 2.05 |

6.4 Evaluation of Solid Forms (a) Solubility Measurements

A weighed sample of each of Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, and Form C of an edisylate salt of Compound 1 is treated with aliquots of the test solvent at ambient temperature or elevated temperature. Complete dissolution of the test material is determined by visual inspection. Solubility was estimated based on the total solvent used to provide complete dissolution of the sample. The actual solubility may be greater than the value calculated because of the use of solvent aliquots that were too large or due to a slow rate of dissolution.

(b) Stability Measurements

Stability of each of Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, and Form C of an edisylate salt of Compound 1 is determined by exposing the sample to a 40° C./75% relative humidity (RH) environment for four weeks or 11% RH at ambient temperature for four days.

6.5 Biological Evaluation (a) S1P$_1$ Assays

The compounds are useful in the treatment of a variety of S1P1 receptor-mediated clinical conditions, including autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas. Therefore, the compounds of the invention may be assayed for their ability to modulate the S1P1 receptor activity. See Colandrea, *Biorg. Med. Chem. Lett.* 2006, 16(11):2905-2908.

(i) In Vitro Binding Assay

The solid forms described herein (e.g., Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, or Form C of an edisylate salt of Compound 1) are evaluated using a [$^{35}$S]-GTPgammaS binding assay to monitor dose-dependent selectivity against S1P1 receptors. The assay is completed with sample solid forms subjected to an eight-point, four-fold dose response curve with starting concentration of 10 µM. Selectivity is determined upon initial addition of solid forms followed by an incubation period. Following compound incubation, bounded [35S]-GTPgammaS is determined by filtration and scintillation counting. Percentage activation and inhibition values are determined relative to the reference agonist at S1P1.

(ii) In Vivo Blood Lymphocyte Depletion Assay

In addition to their S1P1 binding properties, modulators of the S1P1 receptor also have accelerating lymphocyte homing properties. These properties may be measured using a blood lymphocyte depletion assay. The solid forms described herein (e.g., Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, or Form C of an edisylate salt of Compound 1) are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms.

(b) In Vitro Metabolic Disposition in Liver Microsomal Fractions

The stability of each of Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, and Form C of an edisylate salt of Compound 1 is determined according to standard procedures known in the art. For example, stability of each of Form A of an HCl salt of Compound 1, Form B of an HCl salt of Compound 1, Form C of an HCl salt of Compound 1, Form A of an HBr salt of Compound 1, Form B of an HBr salt of Compound 1, Form A of a napadisylate salt of Compound 1, Form B of a napadisylate salt of Compound 1, Form C of a napadisylate salt of Compound 1, Form A of a 2-naphthalenesulfonate salt of Compound 1, Form A of an edisylate salt of Compound 1, Form B of an edisylate salt of Compound 1, and Form C of an edisylate salt of Compound 1 is established by an in vitro assay. An in vitro hepatic microsome stability assay measures the stability of one or more subject compounds when reacting with mouse, rat or human microsomes.

Incubations with liver microsomes are conducted in a final volume of 0.1 mL per incubation time point. 10 µM of the subject compound from a stock solution in DMSO (final DMSO concentration of 0.1%) is incubated at 37° C. from 0-60 min with pooled microsomal protein (1.0 mg/mL), suspended in incubation buffer (0.1 M potassium phosphate, pH 7.4, 5 mM MgCl2, and 0.1 mM EDTA). The microsomal reaction is initiated by the addition of NADPH (3 mM final concentration). Incubations with (a) no protein or (b) no NADPH serve as controls. Reactions are terminated by the addition of 0.2 mL of stop solution (acetonitrile). The samples are vortex-mixed for 30 sec and then centrifuged at 10,000×g for 10 min. The supernatant is dried using a Labconco CentriVap concentrator and the dry residue reconstituted in water, transferred to an HPLC glass vial and analyzed by HPLC-UV. The disappearance of the subject compound is used to evaluate the in vitro metabolism thereof.

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein are in addition to those shown and described herein will become apparent to those skilled in the art and are intended to fall within the scope of the appended claims.

A number of references have been cited, the disclosures of which are incorporated herein by reference in their entirety.

What is claimed is:
1. A solid form comprising a salt of Compound 1:

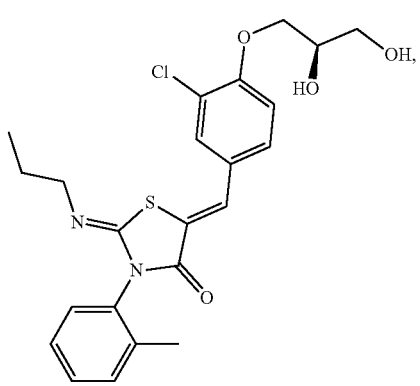

wherein the solid form is Form A of an HCl salt of Compound 1, characterized by an XRPD pattern comprising peaks at 6.6, 9.6, and 16.2° 2θ+0.2° 2θ;

Form B of an HCl salt of Compound 1, characterized by an XRPD pattern comprising peaks at 10.2, 16.9, and 26.0° 2θ+0.2° 2θ;

Form C of an HCl salt of Compound 1, characterized by an XRPD pattern comprising peaks at 10.4, 13.6, and 20.9° 2θ+0.2° 2θ;

Form A of an HBr salt of Compound 1, characterized by an XRPD pattern comprising peaks at 6.6, 16.1, and 20.3° 2θ 0.2° 2θ;

Form B of an HBr salt of Compound 1, characterized by an XRPD pattern comprising peaks at 8.1, 14.9, and 25.2° 2θ 0.2° 2θ;

Form A of a napadisylate salt of Compound 1, characterized by an XRPD pattern comprising peaks at 7.9, 15.8, and 18.5° 2θ±0.2° 2θ;

Form B of a napadisylate salt of Compound 1, characterized by an XRPD pattern comprising peaks at 4.7, 7.4, and 14.0° 2θ+0.2° 2θ;

Form C of a napadisylate salt of Compound 1, characterized by an XRPD pattern comprising peaks at 5.1, 14.0, and 14.9° 2θ 0.2° 2θ;

Form A of a 2-naphthalenesulfonate salt of Compound 1, characterized by an XRPD pattern comprising peaks at 6.3, 19.1, and 20.1° 2θ 0.2° 2θ;

Form A of an edisylate salt of Compound 1, characterized by an XRPD pattern comprising peaks at 4.3, 8.8, and 11.9° 2θ 0.2° 2θ;

Form B of an edisylate salt of Compound 1, characterized by an XRPD pattern comprising peaks at 4.8, 12.4, and 20.7° 2θ+0.2° 2θ; or Form C of an edisylate salt of Compound 1, characterized by an XRPD pattern comprising peaks at 4.5, 15.7, and 20.7° 2θ 0.2° 2θ; wherein the XRPD pattern is obtained using Cu Kα radiation.

2. The solid form of claim 1, which is Form A of an HCl salt of Compound 1, characterized by an XRPD pattern comprising peaks at 6.6, 9.6, and 16.2° 2θ+0.2° 2θ.

3. The solid form of claim 1, which is Form B of an HCl salt of Compound 1, characterized by an XRPD pattern comprising peaks at 10.2, 16.9, and 26.0° 2θ+0.2° 2θ.

4. The solid form of claim 1, which is Form C of an HCl salt of Compound 1, characterized by an XRPD pattern comprising peaks at 10.4, 13.6, and 20.9° 2θ+0.2° 2θ.

5. The solid form of claim 1, which is Form A of an HBr salt of Compound 1, characterized by an XRPD pattern comprising peaks at 6.6, 16.1, and 20.3° 2θ 0.2° 2θ.

6. The solid form of claim 1, which is Form B of an HBr salt of Compound 1, characterized by an XRPD pattern comprising peaks at 8.1, 14.9, and 25.2° 2θ 0.2° 2θ.

7. The solid form of claim 1, is Form A of a napadisylate salt of Compound 1, characterized by an XRPD pattern comprising peaks at 7.9, 15.8, and 18.5° 2θ±0.2° 2θ.

8. The solid form of claim 1, is Form B of a napadisylate salt of Compound 1, characterized by an XRPD pattern comprising peaks at 4.7, 7.4, and 14.0° 2θ±0.2° 2θ.

9. The solid form of claim 1, which is Form C of a napadisylate salt of Compound 1, characterized by an XRPD pattern comprising peaks at 5.1, 14.0, and 14.9° 2θ±0.2° 2θ.

10. The solid form of claim 1, which is Form A of a 2-naphthalenesulfonate salt of Compound 1, characterized by an XRPD pattern comprising peaks at 6.3, 19.1, and 20.1° 2θ±0.2° 2θ.

11. The solid form of claim 1, which is Form A of an edisylate salt of Compound 1, characterized by an XRPD pattern comprising peaks at 4.3, 8.8, and 11.9° 2θ±0.2° 2θ.

12. The solid form of claim 1, which is Form B of an edisylate salt of Compound 1, characterized by an XRPD pattern comprising peaks at 4.8, 12.4, and 20.7° 2θ±0.2° 2θ.

13. The solid form of claim 1, is Form C of an edisylate salt of Compound 1, characterized by an XRPD pattern comprising peaks at 4.5, 15.7, and 20.7° 2θ±0.2° 2θ.

14. A pharmaceutical composition comprising a solid form of claim 1, a pharmaceutically acceptable excipient or carrier.

15. A pharmaceutical composition comprising two or more solid forms of claim 1, and a pharmaceutically acceptable excipient or carrier.

16. The pharmaceutical composition of claim 14, further comprising an amorphous form of Compound 1.

17. The pharmaceutical composition of claim 14, which is a single unit dosage form.

18. The pharmaceutical composition of claim 14, which is a tablet.

19. The pharmaceutical composition of claim 14, which is a capsule.

20. A method of treating multiple sclerosis, comprising administering to a patient in need thereof a therapeutically effective amount of a solid form of claim 1.

21. A method of treating psoriasis, comprising administering to a patient in need thereof a therapeutically effective amount of a solid form of claim 1.

22. A method of treating polymyositis, comprising administering to a patient in need thereof a therapeutically effective amount of a solid form of claim 1.

23. The solid form of claim 2, wherein the XRPD pattern further comprises peaks at 11.1, 20.4, and 24.3° 2θ±0.2° 2θ.

24. The solid form of claim 2, which is characterized by an XRPD pattern that matches the XRPD pattern presented in FIG. 1.

\* \* \* \* \*

UNITED STATES PATENT AND TRADEMARK OFFICE
CERTIFICATE OF CORRECTION

PATENT NO. : 11,186,556 B1
APPLICATION NO. : 16/653629
DATED : November 30, 2021
INVENTOR(S) : Huang et al.

It is certified that error appears in the above-identified patent and that said Letters Patent is hereby corrected as shown below:

In the Claims

In Column 57, Line 67 (Claim 1), replace the "+" before "0.2° 2θ" with "±".

In Column 58, Line 3 (Claim 1), replace the "+" before "0.2° 2θ" with "±".

In Column 58, Line 6 (Claim 1), replace the "+" before "0.2° 2θ" with "±".

In Column 58, Line 9 (Claim 1), insert a -- ± -- before "0.2° 2θ".

In Column 58, Line 12 (Claim 1), insert a -- ± -- before "0.2° 2θ".

In Column 58, Line 19 (Claim 1), replace the "+" before "0.2° 2θ" with "±".

In Column 58, Line 22 (Claim 1), insert a -- ± -- before "0.2° 2θ".

In Column 58, Line 25 (Claim 1), insert a -- ± -- before "0.2° 2θ".

In Column 58, Line 28 (Claim 1), insert a -- ± -- before "0.2° 2θ".

In Column 58, Line 31 (Claim 1), replace the "+" before "0.2° 2θ" with "±".

In Column 58, Line 34 (Claim 1), insert a -- ± -- before "0.2° 2θ".

In Column 58, Line 39 (Claim 2), replace the "+" before "0.2° 2θ" with "±".

In Column 58, Line 42 (Claim 3), replace the "+" before "0.2° 2θ" with "±".

In Column 58, Line 45 (Claim 4), replace the "+" before "0.2° 2θ" with "±".

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,186,556 B1

In Column 58, Line 48 (Claim 5), insert a -- ± -- before "0.2° 2θ".

In Column 58, Line 51 (Claim 6), insert a -- ± -- before "0.2° 2θ".

In Column 59, Line 8 (Claim 14), insert an -- and -- before "a pharmaceutically acceptable excipient or carrier".